United States Patent
Baasov et al.

(10) Patent No.: US 10,159,689 B2
(45) Date of Patent: *Dec. 25, 2018

(54) AMINOGLYCOSIDES AND USES THEREOF IN THE TREATMENT OF GENETIC DISORDERS

(71) Applicant: Technion Research & Development Foundation Limited, Haifa (IL)

(72) Inventors: Timor Baasov, Haifa (IL); Tamar Ben-Yosef, Haifa (IL); Igor Nudelman, Haifa (IL); Annie Rebibo-Sabbah, Haifa (IL); Dalia Shallom-Shezifi, Kibbutz Nasholim (IL); Mariana Hainrichson, Kiryat-Yam (IL)

(73) Assignee: Technion Research & Development Foundation Limited, Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/817,412

(22) Filed: Nov. 20, 2017

(65) Prior Publication Data

US 2018/0064743 A1    Mar. 8, 2018

Related U.S. Application Data

(63) Continuation of application No. 14/738,892, filed on Jun. 14, 2015, now Pat. No. 9,821,001, which is a continuation of application No. 12/285,299, filed on Oct. 1, 2008, now Pat. No. 9,073,958, which is a continuation-in-part of application No. PCT/IL2007/000463, filed on Apr. 10, 2007.

(51) Int. Cl.
| *A61K 31/7036* | (2006.01) |
| *A61K 9/00* | (2006.01) |
| *B65D 25/20* | (2006.01) |
| *C07H 5/06* | (2006.01) |

(52) U.S. Cl.
CPC ........ *A61K 31/7036* (2013.01); *A61K 9/0053* (2013.01); *B65D 25/205* (2013.01); *C07H 5/06* (2013.01)

(58) Field of Classification Search
None
See application file for complete search history.

(56) References Cited

U.S. PATENT DOCUMENTS

| 3,897,412 | A | 7/1975 | Naito et al. |
| 3,996,205 | A | 12/1976 | Magerlein |
| 4,024,332 | A | 5/1977 | Fenner et al. |
| 4,029,882 | A | 6/1977 | Wright |
| 6,462,609 | B2 | 10/2002 | Hashimoto et al. |
| 9,073,958 | B2 * | 7/2015 | Baasov .................... C07H 5/06 |
| 9,821,001 | B2 * | 11/2017 | Baasov .............. A61K 31/7036 |
| 2005/0004052 | A1 | 1/2005 | Baasov et al. |
| 2009/0093418 | A1 | 4/2009 | Bassov et al. |
| 2015/0352136 | A1 | 12/2015 | Baasov et al. |

FOREIGN PATENT DOCUMENTS

| FR | 2427341 | 12/1979 |
| GB | 1494129 | 12/1977 |
| IL | 194370 | 8/2009 |
| JP | 46-29192 | 8/1971 |
| JP | 50-126640 | 10/1975 |
| JP | 04-046189 | 2/1992 |
| JP | 52-33649 | 9/1993 |
| WO | WO 98/30570 | 7/1998 |
| WO | WO 03/044034 | 5/2003 |
| WO | WO 2005/00249 | 1/2005 |
| WO | WO 2005/002498 | 1/2005 |
| WO | WO 2007/113841 | 10/2007 |

OTHER PUBLICATIONS

International Preliminary Report on Patentability dated Oct. 16, 2008 From the International Bureau of WIPO Re. Application No. PCT/IL2007/000463.
Communication Pursuant to Article 94(3) EPC dated Jun. 4, 2013 From the European Patent Office Re. Application No. 07736203.6.
Communication Pursuant to Article 94(3) EPC dated Jul. 9, 2015 From the European Patent Office Re. Application No. 07736203.6.
Communication Pursuant to Article 94(3) EPC dated Jul. 9, 2015 From the European Patent Office Re. Application No. 11173958.7.
Communication Pursuant to Article 94(3) EPC dated May 13, 2016 From the European Patent Office Re. Application No. 07736203.6.
Communication Pursuant to Article 94(3) EPC dated Jul. 15, 2009 From the European Patent Office Re. Application No. 07736203.6.
Communication Pursuant to Article 94(3) EPC dated Nov. 16, 2011 From the European Patent Office Re.: Application No. 07736203.6.
Communication Pursuant to Article 94(3) EPC dated Apr. 18, 2011 From the European Patent Office Re. Application No. 07736203.6.
Communication Pursuant to Article 94(3) EPC dated May 22, 2017 From the European Patent Office Re. Application No. 07736203.6. (3 Pages).
Communication Pursuant to Article 94(3) EPC dated Sep. 25, 2013 From the European Patent Office Re. Application No. 11173958.7.
European Search Report and the European Search Opinion dated Oct. 31, 2011 From the European Patent Office Re. Application No. 11173958.7.
Examination Report dated Feb. 26, 2014 From the Government of India, Patent Office, Intellectual Property Building Re. Application No. 9136/DELNP/2008.
Hearing Notice Dated Sep. 7, 2017 From the Government of India, Patent Office, Intellectual Property Building Re. Application No. 9136/DELNP/2008. (10 Pages).

(Continued)

*Primary Examiner* — Traviss C McIntosh, III

(57) ABSTRACT

A new class of paromomycin-derived aminoglycosides, which exhibit efficient stop-codon mutation suppression activity, low toxicity and high selectivity towards eukaryotic cells are provided. Also provided are chemical and chemo-enzymatic processes of preparing these paromomycin-derived aminoglycosides and intermediates thereof, as well as pharmaceutical compositions containing the same, and uses thereof in the treatment of genetic disorders.

23 Claims, 12 Drawing Sheets
(1 of 12 Drawing Sheet(s) Filed in Color)
Specification includes a Sequence Listing.

(56) References Cited

OTHER PUBLICATIONS

International Search Report dated Oct. 5, 2007 From the International Searching Authority Re. Application No. PCT/IL2007/000463.
Notice of Allowance dated Jul. 7, 2017 From the US Patent and Trademark Office Re. U.S. Appl. No. 14/738,892. (7 Pages).
Office Action dated Apr. 2, 2015 From the Israel Patent Office Re. Application No. 229577.
Office Action dated Aug. 5, 2015 From the Israel Patent Office Re. Application No. 229577.
Office Action dated Jun. 7, 2016 From the Israel Patent Office Re. Application No. 244653 and its Translation Into English.
Office Action dated Apr. 15, 2012 From the Israel Patent Office Re. Application No. 194370 and its Translation Into English.
Office Action dated Mar. 17, 2013 From the Israel Patent Office Re. Application No. 194370 and its Translation Into English.
Office Action dated Aug. 20, 2017 From the Israel Patent Office Re. Application No. 244653 and its Translation Into English. (4 Pages).
Official Action dated Oct. 8, 2010 From the US Patent and Trademark Office Re. U.S. Appl. No. 12/285,299.
Official Action dated Oct. 8, 2014 From the US Patent and Trademark Office Re. U.S. Appl. No. 12/285,299.
Official Action dated Dec. 14, 2010 From the US Patent and Trademark Office Re. U.S. Appl. No. 12/285,299.
Official Action dated Nov. 18, 2016 From the US Patent and Trademark Office Re. U.S. Appl. No. 14/738,892. (23 pages).
Official Action dated Jun. 22, 2011 From the US Patent and Trademark Office Re. U.S. Appl. No. 12/285,299.
Official Action dated Mar. 25, 2014 From the US Patent and Trademark Office Re. U.S. Appl. No. 12/285,299.
Requisition by the Examiner Dated Feb. 27, 2014 From the Canadian Intellectual Property Office Re. Application No. 2,646,407.
Translation Dated Aug. 30, 2015 of Office Action dated Aug. 5, 2015 From the Israel Patent Office Re. Application No. 229577.
Translation of Notice of Reason for Rejection dated Oct. 5, 2012 From the Japanese Patent Office Re. Application No. 2009-503741.
Translation of Notice of Reason for Rejection dated Mar. 8, 2013 From the Japanese Patent Office Re. Application No. 2009-503741.
Written Opinion dated Oct. 5, 2007 From the International Searching Authority Re. Application No. PCT/IL2007/000463.
Alper et al. "Probing the Specificity of Aminoglycoside-Ribosomal RNA Interactions With Designed Synthetic Analogs", Journal of the American Chemical Society, JACS, 120: 1965-1978, 1998.
Burke et al. "Suppression of a Nonsense Mutation in Mammalian Cells in Vivo by the Aminoglycoside Antibiotics G-418 and Paromomycin", Nucleic Acids Research, XP009088534, 13(7): 6265-6272, Sep. 11, 1985.
Carryn et al. "Comparative Intracellular (THP-1 Macrophage) and Extracellular Activities of Beta-Lactams, Azithromycin, Gentamicin, and Fluoroquinolones Against Listeria Monocytogenes at Clinically Relevant Concentrations", Antimicrobial Agents and Chemotherapy, 46(7): 2095-2103, Jul. 2002.
Chang et al. "Pyranmycins, A Novel Class of Aminoglycosides With Improved Acid Stability: The SAR of D-Pyranoses on Ring III of Pyranmycin", Organic Letters, 4(26): 4603-4606, 2002.

Fong et al. "Substrate Promiscuity of an Aminoglycoside Antibiotic Resistance Enzyme Via Target Mimicry", The EMBO Journal, 21(10): 2323-2331, 2002.
Fujisawa et al. "Aminoglycoside Antibiotics. VII. Acute Toxicity of Aminoglycoside Antibiotics", Database CAPLUS [Online], Database Accession No. 1975:92930, 1975.
Greenberg et al. "Design and Synthesis of New Aminoglycoside Antibiotics Containing Neamine as an Optimal Core Structure: Correlation of Antibiotic Activity With in Vitro Inhibition of Translation", Journal of the American Chemical Society, JACS, 121: 6527-6541, 1999.
Haddad et al. "Design of Novel Antibiotics That Bind to the Ribosomal Acyltransfer Site", Journal of the American Chemical Society, JACS, 124: 3229-3237, Mar. 6, 2002.
Hanessian et al. "Probing the Functional Requirements of the L-Haba Side-Chain of Amikacin—Synthesis, 16S A-Site rRNA Binding, and Antibacterial Activity", Tetrahedron, 59: 995-1007, 2003.
Hanessian et al. "Tobramycin Analogues With C-5 Aminoalkyl Ether Chains Intended to Mimic Rings III and IV of Paramomycin", Tetrahedron, 59: 983-993, 2003.
Kotra et al. "Aminoglycosides: Perspectives on Mechanisms of Action and Resistance and Strategies to Counter Resistance", Antimicrobial Agents and Chemotherapy, 44(12): 3249-3256, Dec. 2000.
Lee et al. "Inhibition of the Proteolytic Activity of Anthrax Lethal Factor by Aminoglycosides", Journal of the American Chemical Society, JACS, 126: 4774-4775, Mar. 27, 2004.
Li et al. "Analysis of Unknown Compounds in Gentamicin Bulk Samples With Liquid Chromatography Coupled With Ion Trap Mass Spectrometry", Rapid Communications in Mass Spetrometry, 20(3); 393-402, 2006.
Nudelman et al. "Development of Novel Aminoglycoside (NB54) With Reduced Toxicity and Enhanced Suppression of Disease-Causing Premature Stop Mutations", Journal of Medical Chemistry, XP055042341, 52(9): 2836-2845, Mar. 23, 2009.
Nudelman et al. "Redesign of Aminoglycosides for Treatment of Human Genetic Diseases Caused by Premature Stop Mutations", Bioorganic & Medicinal Chemistry Letters, XP002447819, 16: 6310-6315, 2006.
Nudelman et al. "Repairing Faulty Genes by Aminoglycosides: Development of New Derivatives of Geneticin (G418) With Enhanced Suppression of Diseases—Causing Nonsense Mutations", Bioorganic and Medicinal Chemistry, XP055017979, 18(11): 3735-3746, Jun. 1, 2010.
Simonsen et al. "Novel Paromamine Derivatives Exploring Shallow-Groove Recognition of Ribosomal-Decoding-Site RNA", ChemBioChem, 3(12): 1223-1228, 2002.
Takeda et al. "An Approach to the Biosynthetic Pathway of Butirosins and the Related Antibiotics", The Journal of Antibiotics, 31(3): 250-253, Mar. 1978.
Examination Report Under Sections 12 & 13 of the Patents Act, 1970 and the Patent Rules, 2003 dated Apr. 17, 2018 From the Government of India, Intellectual Property India, Patents, Designs, Trade Marks, Geographical Indications Re. Application No. 4840/DELNP/2015 (3 Pages).

\* cited by examiner

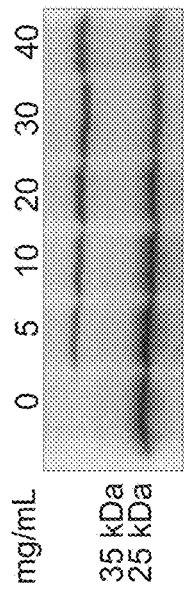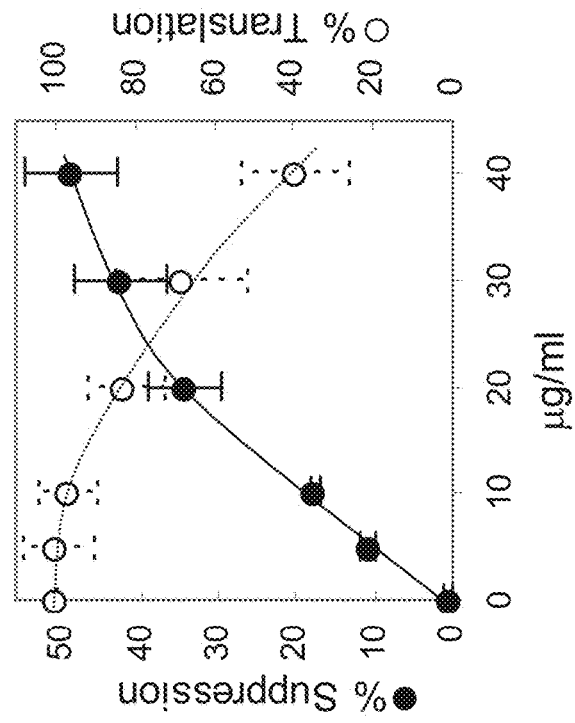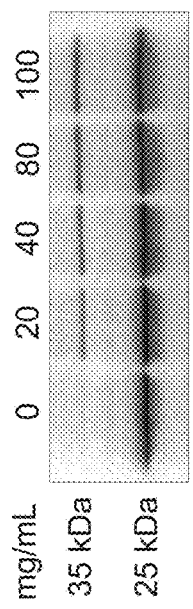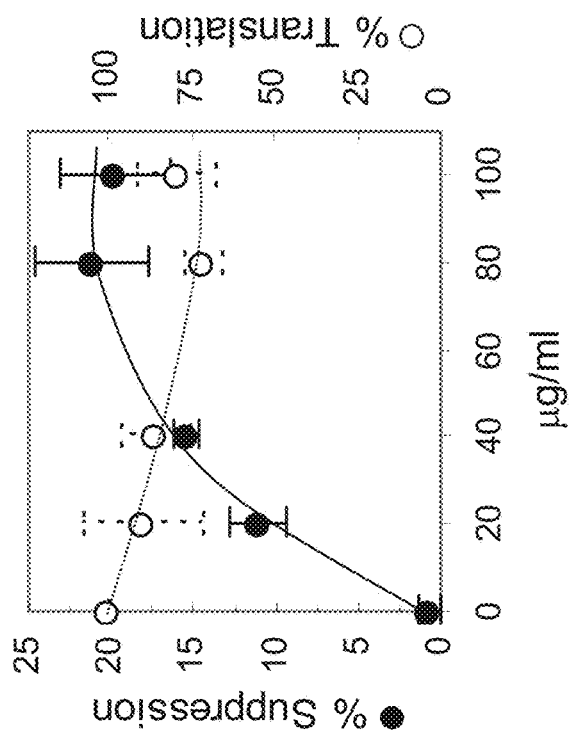
Fig. 3 A  Fig. 3 B  Fig. 3 C  Fig. 3 D

Fig. 9 A) 2D-COSY of Compound 37 prepared chemically
Fig. 9 B) 2D-COSY of Compound 37 prepared chemo-enzymatically
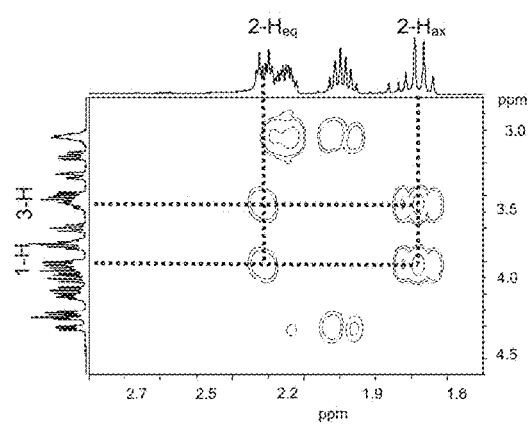
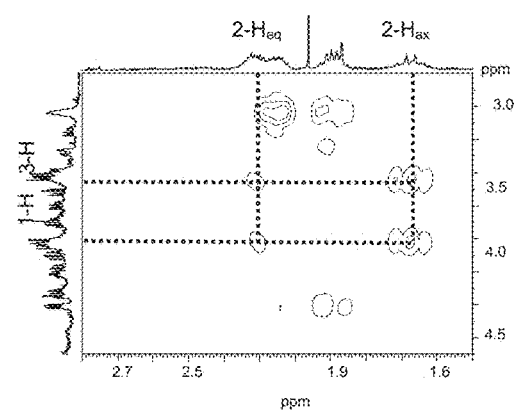
Fig. 9 C) 2D-COSY of Compound 3 (precursor of Compound 37)
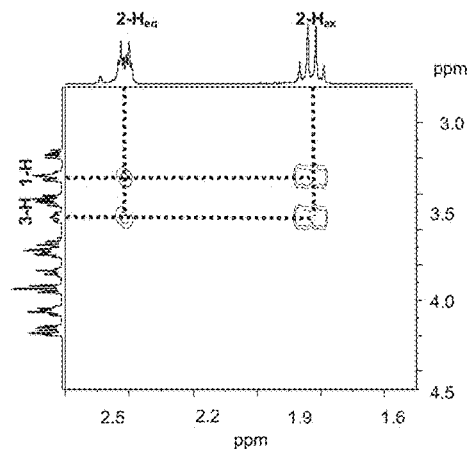

AMINOGLYCOSIDES AND USES THEREOF IN THE TREATMENT OF GENETIC DISORDERS

RELATED APPLICATIONS

This application is a continuation of U.S. patent application Ser. No. 14/738,892 filed on Jun. 14, 2015, which is a continuation of U.S. patent application Ser. No. 12/285,299 filed on Oct. 1, 2008, now U.S. Pat. No. 9,073,958, which is a Continuation-In-Part of PCT Patent Application No. PCT/IL2007/000463 having International Filing Date of Apr. 10, 2007. The contents of the above applications are all incorporated by reference as if fully set forth herein in their entirety.

SEQUENCE LISTING STATEMENT

The ASCII file, entitled 71880SequenceListing.txt, created on Nov. 20, 2017, comprising 5,002 bytes, submitted concurrently with the filing of this application is incorporated herein by reference.

FIELD AND BACKGROUND OF THE INVENTION

The present invention relates to a new class of aminoglycosides and to uses thereof in the treatment of genetic disorders.

Many human genetic disorders result from nonsense mutations, where one of the three stop codons (UAA, UAG or UGA) replaces an amino acid-coding codon, leading to premature termination of the translation and eventually to truncated inactive proteins. Currently, hundreds of such nonsense mutations are known, and several were shown to account for certain cases of fatal diseases, including cystic fibrosis (CF), Duchenne muscular dystrophy (DMD), ataxia-telangiectasia, Hurler syndrome, hemophilia A, hemophilia B, Tay-Sachs, and more [1, 2]. For many of those diseases there is presently no effective treatment, and although gene therapy seems like a potential possible solution for genetic disorders, there are still many critical difficulties to be solved before this technique could be used in humans.

During the last several years, it has been shown that aminoglycosides could have therapeutic value in the treatment of several genetic diseases because of their ability to induce ribosomes to read-through stop codon mutations, generating full-length proteins from part of the mRNA molecules [3-6].

Aminoglycosides are highly potent, broad-spectrum antibiotics commonly used for the treatment of life-threatening infections [7, 8]. The 2-deoxystreptamine (2-DOS) aminoglycosides antibiotics, shown in background art FIG. 1, selectively target the prokaryotic ribosome, and, by binding to the decoding A-site of the 16S ribosomal RNA, lead to protein translation inhibition and interference with the translational fidelity [7, 10-12]. One of the most studied aminoglycosides is paromomycin (its sulfate salt known under its brand name Humatin), which is an antimicrobial drug used against intestinal amebiasis. It was approved by the Drug Controller General of India as an agent against visceral leishmaniasis (kala azar) in India, and was granted "orphan drug" status in 2005 in the US. Paromomycin is known to inhibit protein synthesis by binding to the ribosomal RNA of the 16S subunit.

Several achievements in bacterial ribosome structure determination [13-17], along with crystal and NMR structures of bacterial A-site oligonucleotide models [18-22], have provided useful information for understanding the decoding mechanism in prokaryote cells and understanding how aminoglycosides exert their deleterious misreading of the genetic code. During decoding, a critical step in aminoacyl-tRNA selection is based on the formation of a mini-helix between the codon of the mRNA and the anti-codon of the cognate aminoacyl-tRNA. In this process, the conformation of the A-site is changed from an 'off' state, where the two conserved adenines A1492 and A1493 are folded back within the helix, to an 'on' state, where A1492 and A1493 are flipped out from the A-site and interact with the cognate codon-anticodon mini-helix [11, 15]. This conformational change is a molecular switch that decides on the continuation of translation in an irreversible way. The binding of aminoglycosides such as paromomycin and gentamicin to the bacterial A-site stabilizes the 'on' conformation even in the absence of cognate tRNA-mRNA complex. Thus, the affinity of the A-site for a non-cognate mRNA-tRNA complex is increased upon aminoglycosides binding, preventing the ribosome from efficiently discriminating between non-cognate and cognate complexes.

The termination of protein synthesis is signaled by the presence of a stop codon in the mRNA, and is mediated by release factor proteins. The efficiency of translation termination is usually very high, and in intact cells the misincorporation of an amino acid at a stop codon (suppression) normally occurs at a low frequency of around $10^{-4}$. The enhancement of termination suppression by aminoglycosides in eukaryotes is thought to occur in a similar mechanism to the aminoglycosides' activity in interfering with translational fidelity during protein synthesis, namely the binding of certain aminoglycosides to the ribosomal A-site probably induce conformational changes that stabilize near-cognate mRNA-tRNA complexes, instead of inserting the release factor. Aminoglycosides suppress the various stop codons with notably different efficiencies (UGA>UAG>UAA), and the suppression effectiveness is further dependent upon the identity of the fourth nucleotide immediately downstream from the stop codon (C>U>A≥G) as well as the local sequence context around the stop codon [6, 23].

The fact that aminoglycosides could suppress premature nonsense mutations in mammalian cells was first demonstrated by Burke and Mogg in 1985, who also noted the therapeutic potential of these drugs in the treatment of genetic disorders [3].

The first genetic disease examined was cystic fibrosis (CF), the most prevalent autosomal recessive disorder in the Caucasian population, affecting 1 in 2,500 newborns. CF is caused by mutations in the cystic fibrosis transmembrane conductance regulator (CFTR) protein. Currently, more than 1,000 different CF-causing mutations in the CFTR gene were identified, and 5-10% of the mutations are premature stop codons. In Ashkenazi Jews, the W1282X mutation and other nonsense mutations account for 64% of all CFTR mutant alleles [5].

The first experiments of aminoglycoside-mediated suppression of CFTR stop mutations demonstrated that premature stop mutations found in the CFTR gene could be suppressed by G-418 and gentamicin (see, background art FIG. 1), as measured by the appearance of full-length, functional CFTR in bronchial epithelial cell lines [24, 25]. Suppression experiments of intestinal tissues from CFTR−/− transgenic mice mutants carrying a human CFTR-G542X transgene showed that treatment with gentamicin, and to lesser extent tobramycin, have resulted in the appearance of human CFTR protein at the glands of treated mice [26]. Most importantly, clinical studies using double-blind, placebo-controlled, crossover trails have shown that gentamicin can suppress stop mutations in affected patients, and that gentamicin treatment improved transmembrane conductance across the nasal mucosa in a group of 19 patients carrying CFTR stop mutations [27]. Other genetic disorders for which the therapeutic potential of aminoglycosides was tested in in-vitro systems, cultured cell lines, or animal models include DMD [28], Hurler syndrome [29], nephrogenic diabetes insipidus [30], nephropathic cystinosis [31], retinitis pigmentosa [32], and ataxia-telangiectasia [33].

However, one of the major limitations in using aminoglycosides as pharmaceuticals is their high toxicity towards mammals, typically expressed in kidney (nephrotoxicity) and ear-associated (ototoxicity) illnesses. The origin of this toxicity is assumed to result from a combination of different factors and mechanisms such as interactions with phospholipids, inhibition of phospholipases and the formation of free radicals [34, 35]. Although considered selective to bacterial ribosomes, most aminoglycosides bind also to the eukaryotic A-site but with lower affinities than to the bacterial A-site [36]. The inhibition of translation in mammalian cells is also one of the possible causes for the high toxicity of these agents. Another factor adding to their cytotoxicity is their binding to the mitochondrial 12S rRNA A-site, whose sequence is very close to the bacterial A-site [37].

Many studies have been attempted to understand and offer ways to alleviate the toxicity associated with aminoglycosides [38], including the use of antioxidants to reduce free radical levels [39, 40], as well as the use of poly-L-aspartate [41, 42] and daptomycin [43, 44] to reduce the ability of aminoglycosides to interact with phospholipids. The role of megalin (a multiligand endocytic receptor which is especially abundant in the kidney proximal tubules and the inner ear) in the uptake of aminoglycosides has recently been demonstrated [35]. The administration of agonists that compete for aminoglycoside binding to megalin also resulted in a reduction in aminoglycoside uptake and toxicity [45]. In addition, altering the administration schedule and/or the manner in which aminoglycosides are administered has been investigated as means to reduce toxicity [46, 47].

Despite extensive efforts to reduce aminoglycoside toxicity, few results have matured into standard clinical practices and procedures for the administration of aminoglycosides to suppress stop mutations, other than changes in the administration schedule. For example, the use of sub-toxic doses of gentamicin in the clinical trails probably caused the reduced read-through efficiency obtained in the in-vivo experiments compared to the in-vitro systems [48]. The aminoglycoside Geneticin® (G-418 sulfate, see, background art FIG. 1) showed the best termination suppression activity in in-vitro translation-transcription systems [6], however, its use as a therapeutic agent is not possible since it is lethal even at very low concentrations. For example, the $LD_{50}$ of G-418 against human fibroblast cells is 0.04 mg/ml, compared to 2.5-5.0 mg/ml for gentamicin, neomycin and kanamycin [49].

The increased sensitivity of eukaryotic ribosomes to some aminoglycoside drugs, such as G-418 and gentamicin, is intriguing but up to date could not be rationally explained because of the lack of sufficient structural data on their interaction with eukaryotic ribosomes. Since G-418 is extremely toxic even at very low concentrations, presently gentamicin is the only aminoglycoside tested in various animal models and clinical trials. Although some studies have shown that due to their relatively lower toxicity in cultured cells, amikacin [50] and paromomycin [51] can represent alternatives to gentamicin for stop mutation suppression therapy, no clinical trials with these aminoglycosides have been reported yet.

To date, nearly all suppression experiments have been performed with clinical, commercially available aminoglycosides [6], and no efforts have been made to optimize their activity as stop codon read-through inducers. Currently, only a limited number of aminoglycosides, including gentamicin, amikacin, and tobramycin, are in clinical use as antibiotics for internal administration in humans. Among these, tobramycin do not have stop mutations suppression activity, and gentamicin is the only aminoglycoside tested for stop mutations suppression activity in animal models and clinical trials. Recently, a set of neamine derivatives were shown to promote read-through of the SMN protein in fibroblasts derived from spinal muscular atrophy (SPA) patients; however, these compounds were originally designed as antibiotics and no conclusions were derived for further improvement of the read-through activity of these derivatives [52].

U.S. patent application Ser. No. 11/073,649, by the present assignee, which is incorporated by reference as if fully set forth herein, teaches a family of aminoglycosides, which have common structural backbone features which enables these aminoglycosides to be highly potent and effective antibiotics, while reducing or blocking antibiotic resistance thereto. The aminoglycoside derivatives taught in U.S. patent application Ser. No. 11/073,649, are presented as effective antibiotics against bacterial infections such as anthrax, and also as therapeutic agents for the treatment of genetic disorder, such as cystic fibrosis.

More specifically, the compounds taught in U.S. patent application Ser. No. 11/073,649 were designed based upon known aminoglycosides antibiotics which exert their anti-bacterial activity by selectively recognizing and binding to the decoding A site on the 16S subunit of the bacterial rRNA. Thus, these compounds are semi-synthetic analogs of currently available aminoglycosides, in which a pre-determined position of the aminoglycoside has been modified so as to enhance the recognition of the phosphodiester bond of rRNA and in parallel the Asp/Glu and Asn/Gln clusters in the active site of the lethal factor (LF) and thereby exhibit enhanced anti-bacterial performance. These modifications further provide the compounds with resistance to enzymatic catalysis and thus improve their bioavailability and hence anti-bacterial performance. Furthermore, the steric hindrance introduced into the designed structures via the chemical modification of the aminoglycoside, renders these compounds inferior substrates for the most widely represented resistance-causing enzyme, APH(3')-IIIa, thus preventing the development of resistance thereto.

The design and bifunctional activity of these structures is also described by Mariana Hainrichson et al, in *Bioorganic and Medicinal Chemistry* 13 (2005) 5797-5807.

The compounds taught in the compounds taught in U.S. patent application Ser. No. 11/073,649 were further found to block a premature stop codon and hence effective in treating genetic disorders. However, as detailed hereinbelow, the enhanced antibacterial activity of these compounds may be undesirable when used to treat genetic disorders. Other modified aminoglycosides and structurally related antibiotics have been proposed and prepared [53-61] yet the stop-codon read-through therapeutic activity thereof was neither described nor suggested or tested.

The desired characteristics of an effective read-through drug would be oral administration and little or no effect on bacteria. Antimicrobial activity of read-through drug is undesirable as any unnecessary use of antibiotics, particularly with respect to the gastrointestinal (GI) biota, due to the adverse effects caused by upsetting the GI biota equilibrium and the emergence of resistance. In this respect, in addition to the abovementioned limitations, the majority of clinical aminoglycosides are greatly selective against bacterial ribosomes, and do not exert a significant effect on cytoplasmic ribosomes of human cells.

In an effort to circumvent the abovementioned limitations, the biopharmaceutical company PTC Therapeutics (NY, USA) is trying currently to discover new stop mutations suppression drugs by screening large chemical libraries for nonsense read-through activity. Using this approach, a new non-aminoglycoside compound, PTC124, was discovered [62].

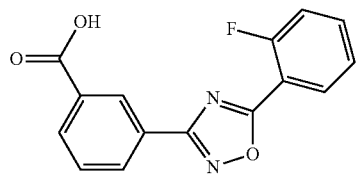

3-[5-(2-fluorophenyl)-1,2,4-oxadiazol-3-yl]benzoic acid

The facts that PTC124 is reported to have no antibacterial activity and no reported toxicity, suggest that its mechanism of action on the ribosome is different than that of the aminoglycosides. The FDA has granted fast track and orphan drug designations to PTC124 for the treatment of both CF and DMD caused by nonsense mutations, and the preliminary results of phase II clinical trails in CF and DMD patients seem promising [63-67].

SUMMARY OF THE INVENTION

In summary, the collective data presented above suggest that systematic search for new aminoglycoside derivatives with improved termination mutation suppression activity, lower toxicity to mammalian cells, and limited or no antimicrobial activity is required to exploit the avenue of aminoglycoside derivative research to the point where they can be used clinically.

The present invention relates to a new class of paromomycin derived aminoglycosides, which can be beneficially used in the treatment of genetic diseases, such as cystic fibrosis, by exhibiting high premature stop-codon mutations read-through activity while exerting low toxicity in mammalian cells and low antimicrobial activity.

Thus, according to one aspect of the present invention there is provided a compound having a general Formula I:

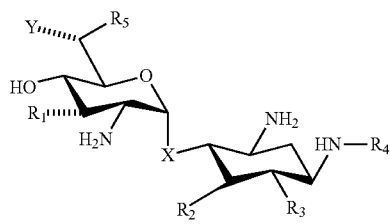

or a pharmaceutically acceptable salt thereof,
wherein:
each of $R_1$, $R_2$ and $R_3$ is independently a monosaccharide moiety, halide, hydroxyl, amine or an oligosaccharide moiety, X is oxygen or sulfur;
$R_4$ is hydrogen or (S)-4-amino-2-hydroxybutyryl (AHB);
$R_5$ is hydroxyl or amine;
Y is hydrogen, alkyl or aryl;
the dashed line indicates an R configuration or an S configuration;
with the proviso that the compound is not selected from the group consisting of

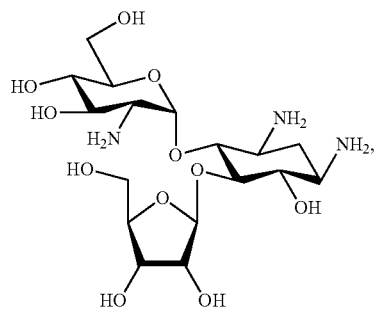

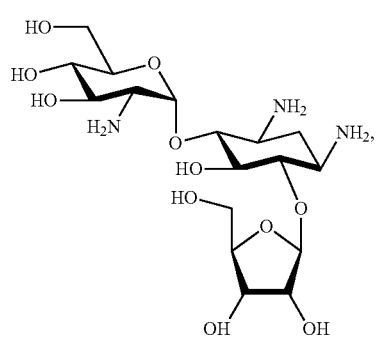

amikacin, apramycin, arbekacin, butirosin, dibekacin, fortimycin, G-418, gentamicin, hygromycin, habekacin, dibekacin, netlmicin, istamycin, isepamycin, kanamycin, lividomycin, neamine, neomycin, paromomycin, ribostamycin, sisomycin, spectinomycin, streptomycin and tobramycin.

According to some embodiments, the compound having a general Formula I is selected from the group consisting of:

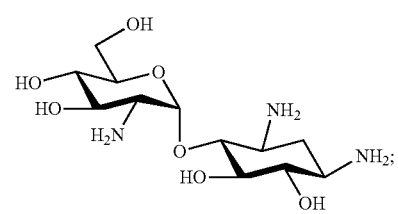

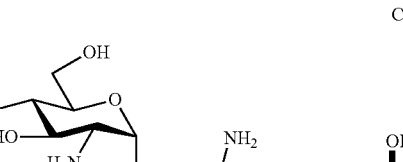

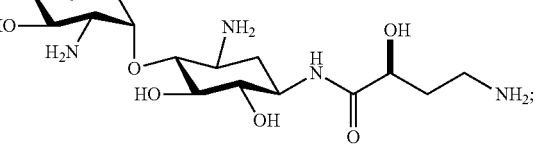

-continued

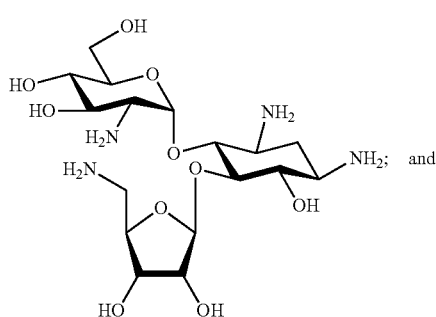

Compound 3

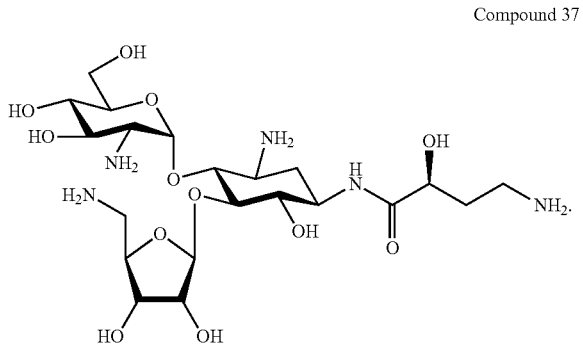

Compound 37

According to another aspect of the present invention there is provided a pharmaceutical composition comprising a compound as described herein and a pharmaceutically acceptable carrier.

According to some embodiments, the pharmaceutical composition is packaged in a packaging material and identified in print, in or on the packaging material, for use in the treatment of a genetic disorder.

According to some embodiments, the pharmaceutical composition is formulated for oral administration.

According to yet another aspect of the present invention there is provided a method of treating a genetic disorder, the method comprising administering to a subject in need thereof a therapeutically effective amount of a compound having a general Formula I, with the proviso that the compound is not selected from the group consisting of amikacin, apramycin, arbekacin, butirosin, dibekacin, fortimycin, G-418, gentamicin, hygromycin, habekacin, dibekacin, netlmicin, istamycin, isepamycin, kanamycin, lividomycin, neamine, neomycin, paromomycin, ribostamycin, sisomycin, spectinomycin, streptomycin and tobramycin.

According to some embodiments, the compound is administered orally.

According to still another aspect of the present invention there is provided a use of a compound having a general Formula I in the manufacture of a medicament for treating a genetic disorder, with the proviso that the compound is not selected from the group consisting of amikacin, apramycin, arbekacin, butirosin, dibekacin, fortimycin, G-418, gentamicin, hygromycin, habekacin, dibekacin, netlmicin, istamycin, isepamycin, kanamycin, lividomycin, neamine, neomycin, paromomycin, ribostamycin, sisomycin, spectinomycin, streptomycin and tobramycin.

According to some embodiments, the genetic disorder comprises a protein having a truncation mutation.

According to some embodiments, the genetic disorder is selected from the group consisting of cystic fibrosis (CF), Duchenne muscular dystrophy (DMD), ataxia-telangiectasia, Hurler syndrome, hemophilia A, hemophilia B, Usher syndrome and Tay-Sachs. Preferably, the genetic disorder is selected from the group consisting of cystic fibrosis (CF), Duchenne muscular dystrophy (DMD) and Hurler syndrome.

According to features in preferred embodiments of the invention described below, X in Formula I is oxygen.

According to some embodiments, $R_5$ in Formula I is hydroxyl.

According to some embodiments, Y in Formula I is hydrogen.

According to some embodiments, at least one of $R_1$, $R_2$ and $R_3$ in Formula I is a monosaccharide moiety.

According to some embodiments, $R_1$ is the monosaccharide moiety.

According to some embodiments, $R_2$ and $R_3$ are each hydroxyl.

According to some embodiments, $R_2$ is the monosaccharide moiety.

According to some embodiments, $R_1$ and $R_3$ are each hydroxyl.

According to some embodiments, $R_3$ is the monosaccharide moiety.

According to some embodiments, $R_1$ and $R_2$ are each hydroxyl.

According to some embodiments, the monosaccharide moiety has the general Formula II:

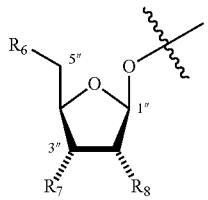

Formula II wherein:

the dashed line indicates an R configuration or an S configuration; and each of $R_6$, $R_7$ and $R_8$ is independently selected from the group consisting of hydroxyl and amine.

According to some embodiments, $R_7$ and $R_8$ in Formula II are each hydroxyl.

According to some embodiments, $R_6$ in Formula II is amine.

According to some embodiments, $R_6$ in Formula II is hydroxyl.

According to some embodiments, $R_1$ is amine and $R_2$ and $R_3$ are each hydroxyl.

According to some embodiments, at least of $R_1$, $R_2$ and $R_3$ is an oligosaccharide moiety.

According to some embodiments, $R_1$ is an oligosaccharide moiety. Preferably, $R_2$ and $R_3$ are each hydroxyl.

According to some embodiments, $R_2$ is an oligosaccharide moiety. Preferably, $R_1$ and $R_3$ are each hydroxyl.

According to some embodiments, $R_3$ is an oligosaccharide moiety. Preferably, $R_1$ and $R_2$ are each hydroxyl.

According to some embodiments, the oligosaccharide moiety is a disaccharide moiety.

According to some embodiments, the disaccharide moiety has the general Formula I*:

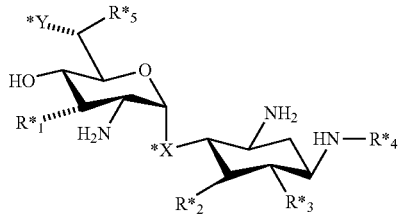

Formula I* wherein:
the dashed line indicates an R configuration or an S configuration;
each of $R^*_1$, $R^*_2$ and $R^*_3$ is independently a halide, hydroxyl, amine or is linked to the compound having general Formula I, whereas at least one of $R^*_1$, $R^*_2$ and $R^*_3$ is linked to the compound having the general Formula I above;
$X^*$ is oxygen or sulfur;
$R^*_4$ is hydrogen or an (S)-4-amino-2-hydroxybutyryl (AHB) moiety;
$R^*_5$ is hydroxyl or amine; and
$Y^*$ is hydrogen, alkyl or aryl.

According to some embodiments, the oligosaccharide moiety further comprises a linker.

According to some embodiments, $R_4$ and Y are each hydrogen.

According to some embodiments, $R_4$ is AHB.

According to still further some embodiments $R_5$ is selected from the group consisting of hydroxyl and amine and Y is alkyl.

According to some embodiments, each of the compounds presented herein has selective activity towards eukaryotic cells over prokaryotic cells.

According to some embodiments, each of the compounds presented herein has no antibacterial activity.

According to yet another aspect of the present invention there is provided a process of preparing a compound having the general Formula I as described herein, wherein $R_1$ in Formula I is a monosaccharide moiety and $R_2$ and $R_3$ are each hydroxyl, the process comprising:
(a) coupling a compound having the general Formula III:

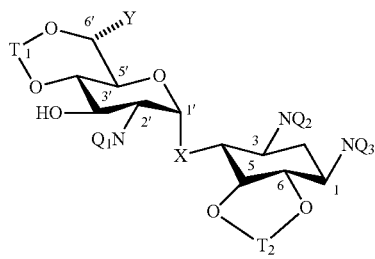

Formula III wherein:
the dashed line indicates an R configuration or an S configuration;
Y is hydrogen, alkyl or aryl;
each of $T_1$-$T_2$ is independently a hydroxyl protecting group;

each of $Q_1$ and $Q_2$ is independently an amine protecting group;
$Q_3$ is selected from the group consisting of an amine protecting group and an AHB moiety, the AHB moiety comprises at least one of a hydroxyl protecting group and an amine protecting group; and
X is oxygen or sulfur,
with a derivative of a monosaccharide having a leaving group attached at position 1″ thereof and at least one of a hydroxyl protecting group and an amino protecting group; and
(b) removing each of the hydroxyl protecting groups and the amine protecting groups, thereby obtaining the compound.

According some embodiments, each of $T_1$-$T_2$ is cyclohexanone dimethyl ketal.

According to yet another aspect of the present invention there is provided a process of preparing a compound having the general Formula I as described herein, wherein $R_2$ in Formula I is a monosaccharide moiety and $R_1$ and $R_3$ are each hydroxyl, the process comprising:
(a) coupling a compound having the general Formula IV:

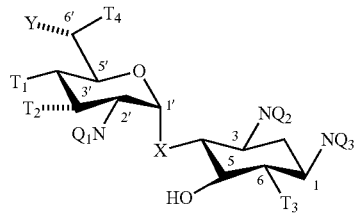

Formula IV wherein:
the dashed line indicates an R configuration or an S configuration;
Y is hydrogen, alkyl or aryl;
each of $T_1$-$T_4$ is independently a hydroxyl protecting group;
each of $Q_1$ and $Q_2$ is independently an amine protecting group;
$Q_3$ is selected from the group consisting of an amine protecting group and an AHB moiety, the AHB moiety comprises at least one of a hydroxyl protecting group and an amine protecting group; and
X is oxygen or sulfur,
with a derivative of a monosaccharide having a leaving group attached at position 1″ thereof and at least one of a hydroxyl protecting group and an amino protecting group; and
(b) removing each of the hydroxyl protecting groups and the amine protecting groups, thereby obtaining the compound.

According to some embodiments, each of $T_1$-$T_4$ is O-acetyl.

According to yet another aspect of the present invention there is provided a process of preparing a compound having the general Formula I as described herein, wherein $R_3$ in Formula I is a monosaccharide moiety and $R_1$ and $R_2$ are each hydroxyl, the process comprising:

(a) coupling a compound having the general Formula V:

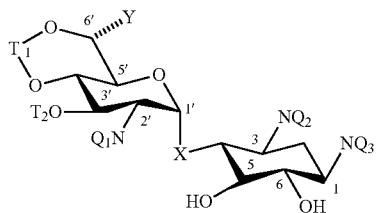

Formula V wherein:
the dashed line indicates an R configuration or an S configuration;
Y is hydrogen, alkyl or aryl;
each of $T_1$-$T_2$ is independently a hydroxyl protecting group;
each of $Q_1$ and $Q_2$ is independently an amine protecting group;
$Q_3$ is selected from the group consisting of an amine protecting group and an AHB moiety, the AHB moiety comprises at least one of a hydroxyl protecting group and an amine protecting group; and
X is oxygen or sulfur,
with a derivative of a monosaccharide having a leaving group attached at position 1" thereof and at least one of a hydroxyl protecting group and an amino protecting group; and
(b) removing each of the hydroxyl protecting groups and the amine protecting groups, thereby obtaining the compound.

According to some embodiments, $T_1$ is 4-methoxy-1-methylbenzene and $T_2$ is O-benzoyl.

According to some embodiments, the protected monosaccharide has the general Formula VI:

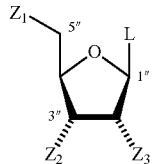

Formula VI wherein:
the dashed line indicates an R configuration or an S configuration;
each of $Z_1$, $Z_2$ and $Z_3$ is independently selected from the group consisting of the hydroxyl protecting group and the amine protecting group; and
L is the leaving group.

According to some embodiments, L in Formula VI is selected from the group consisting of p-tolylsulfide (p-thiotoluene), thioethyl and trichloroacetimidate.

According to some embodiments, each of $Z_1$-$Z_3$ in Formula VI is a hydroxyl protecting group.

According to yet another aspect of the present invention there is provided a process of preparing a compound having the general Formula I as described herein, wherein $R_1$ is amine and $R_2$ and $R_3$ are each hydroxyl, the process comprising:
(a) reacting a compound having the general Formula III with triflic anhydride to thereby obtain a trifluoro-methanesulfonate group at position 3' thereof;

(b) reacting the compound having the trifluoro-methanesulfonate group at position 3' thereof with sodium azide; and
(c) removing each of the hydroxyl protecting groups and the amine protecting groups, thereby obtaining the compound.

According to yet another aspect of the present invention there is provided a process of preparing a compound having the general Formula I as described herein, wherein $R_1$ is the disaccharide moiety having the general Formula I*, and $R_2$ and $R_3$ are each hydroxyl, the process comprising:
(a) coupling a compound having the general Formula III with a compound having the general Formula III*:

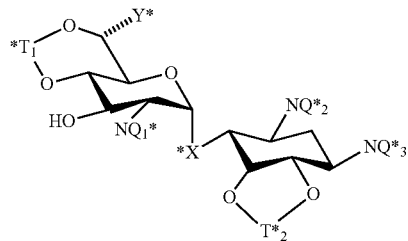

Formula III* wherein:
the dashed line indicates an R configuration or an S configuration;
Y* is hydrogen, alkyl or aryl;
each of $T^*_1$-$T^*_2$ is independently a hydroxyl protecting group;
each of $Q^*_1$ and $Q^*_2$ is independently an amine protecting group;
$Q^*_3$ is selected from the group consisting of an amine protecting group and an AHB moiety, the AHB moiety comprises at least one of a hydroxyl protecting group and an amine protecting group; and
X* is oxygen or sulfur; and
(b) removing each of the hydroxyl protecting groups and the amine protecting groups, thereby obtaining the compound.

According to some embodiments, the coupling is effected via a linker, and preferably the linker is an alkyl.

According to some embodiments, each of the amine protecting group is selected from the group consisting of an azido group and a N-phthalimide group.

According to some embodiments, the hydroxyl-protecting group is selected from the group consisting of O-acetyl, O-chloroacetyl and O-benzoyl.

According to yet another aspect of the present invention there is provided a process of preparing a compound having a general Formula I:

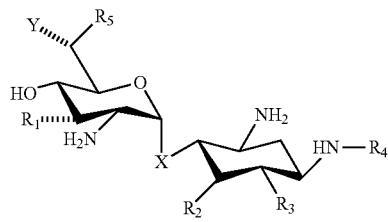

Formula I wherein:
each of $R_1$, $R_2$ and $R_3$ is independently a monosaccharide moiety, halide, hydroxyl, amine or an oligosaccharide moiety, X is oxygen or sulfur;
R$_4$ is (S)-4-amino-2-hydroxybutyryl (AHB);
R$_5$ is hydroxyl or amine;
Y is hydrogen, alkyl or aryl;
the dashed line indicates an R configuration or an S configuration;
the process is effected by:
reacting a compound having the general Formula I wherein R$_4$ is hydrogen with γ-L-Glu-AHB-SNAC in the presence of enzyme BtrH to thereby obtain a compound having the general Formula I wherein R$_4$ is a γ-L-Glu-AHB; and reacting the compound having the general Formula I wherein R$_4$ is a γ-L-Glu-AHB with enzyme BtrG to thereby obtain the compound having the general Formula I wherein R$_4$ is (S)-4-amino-2-hydroxybutyryl (AHB).

As used herein the term "about" refers to ±10%.

The terms "comprises", "comprising", "includes", "including", "having" and their conjugates mean "including but not limited to". The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a biomolecule" or "at least one biomolecule" may include a plurality of biomolecules, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
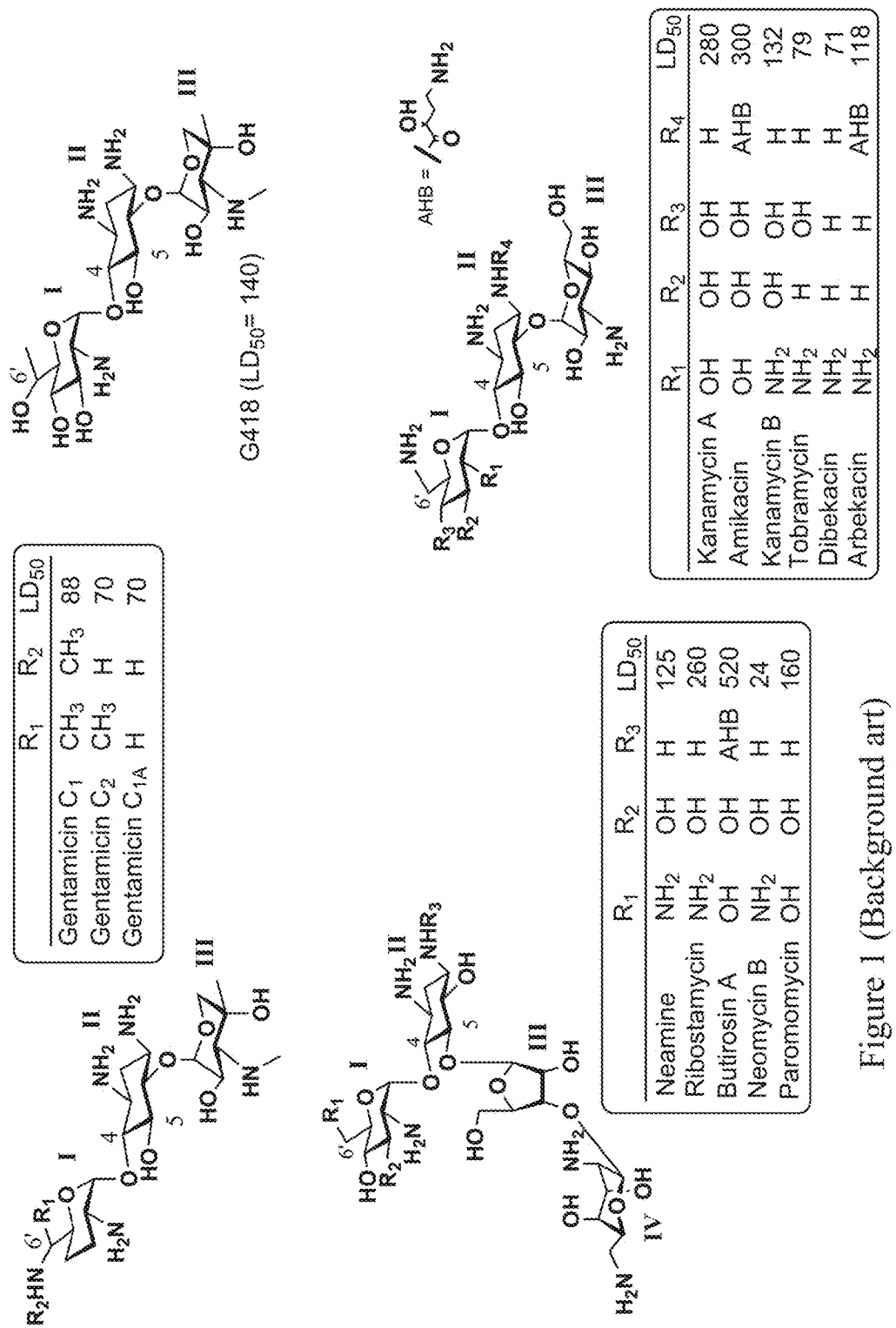
Figure 2:
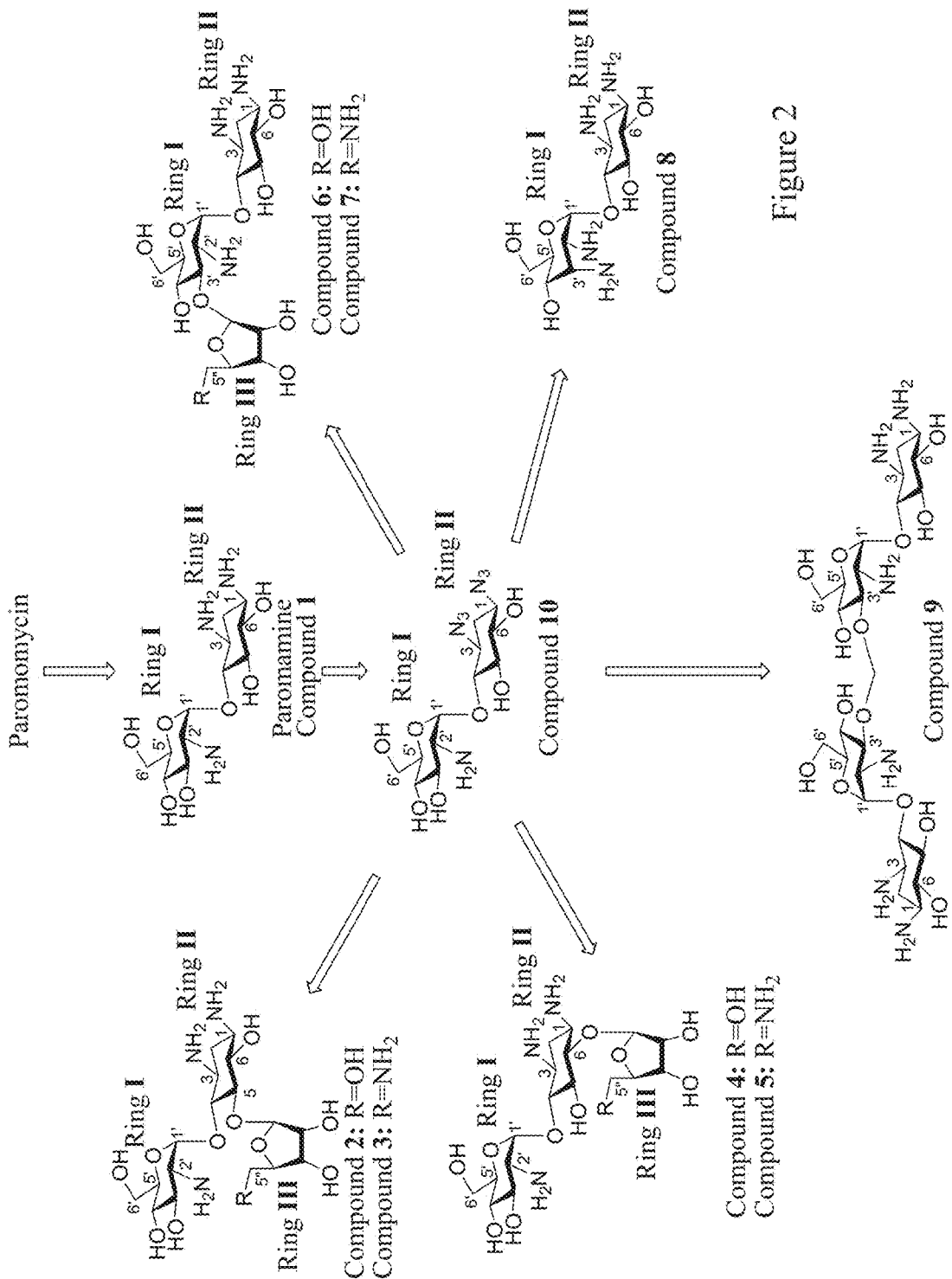
Figure 4:
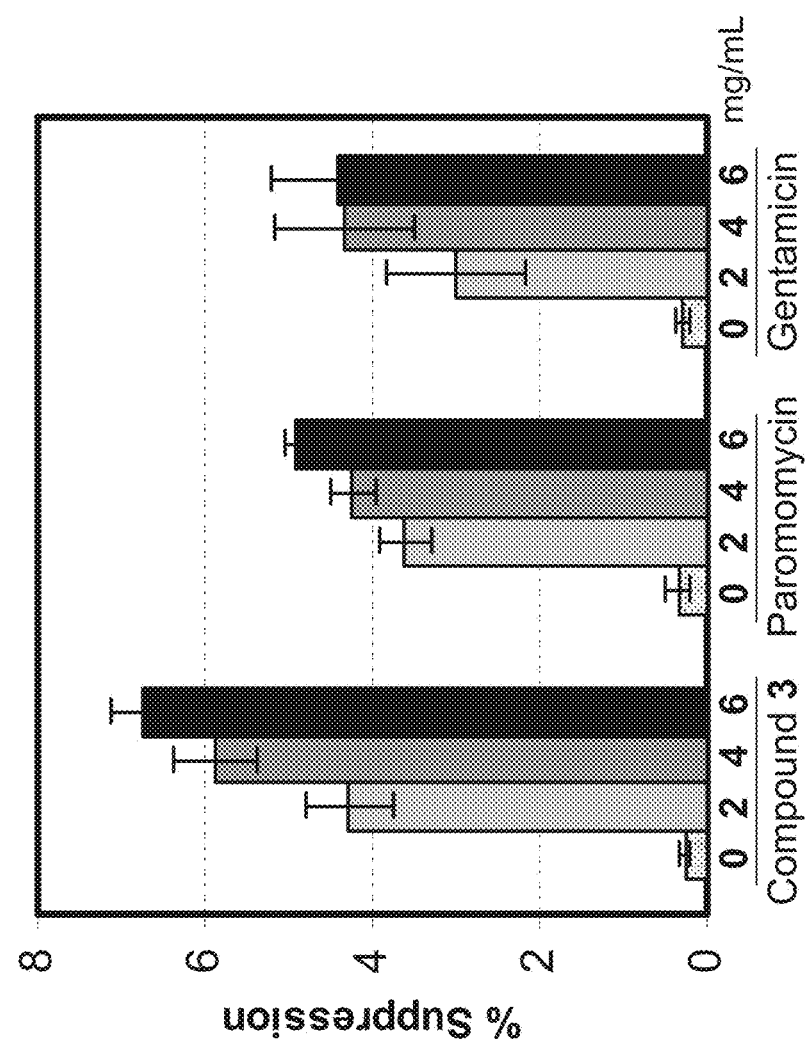
Figure 5A:
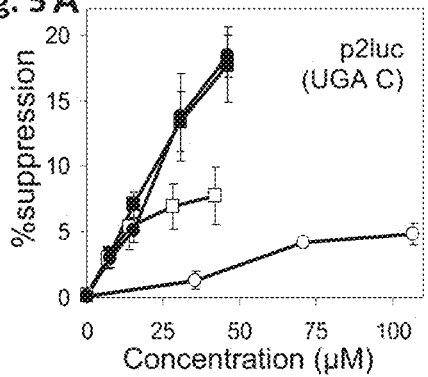
Figure 5B:
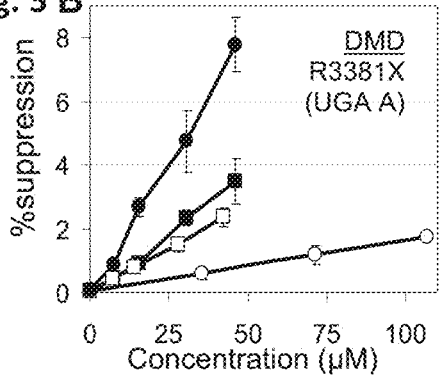
Figure 5C:
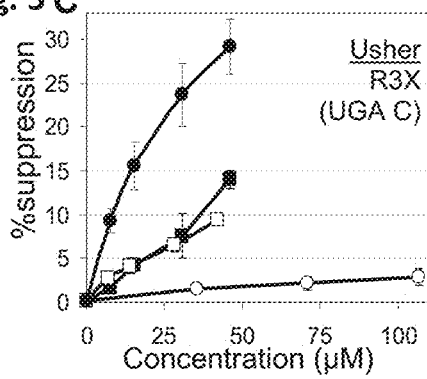
Figure 5D:
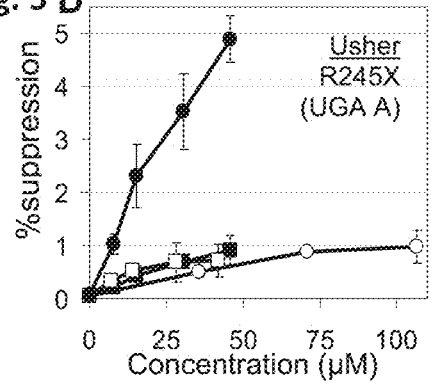
Figure 5E:
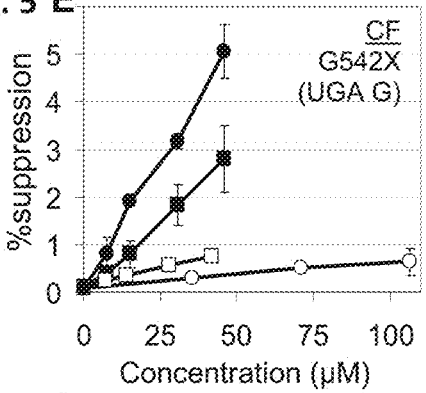
Figure 5F:
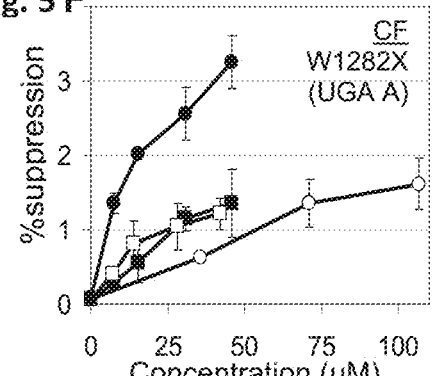
Figure 5G:
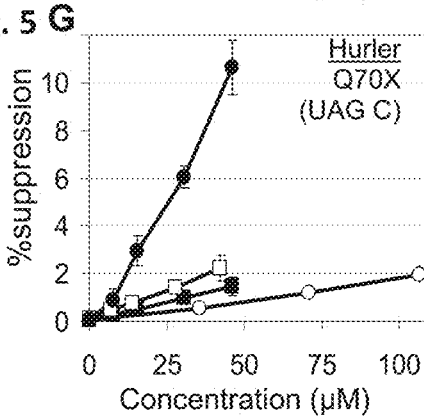
Figure 5H:
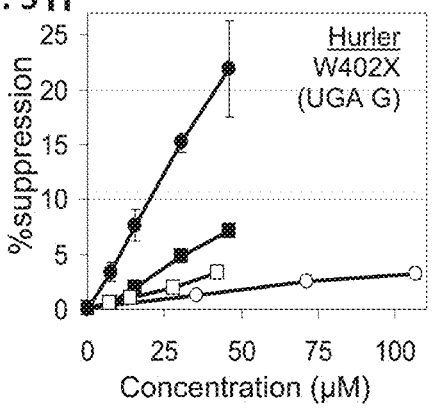
Figure 6:
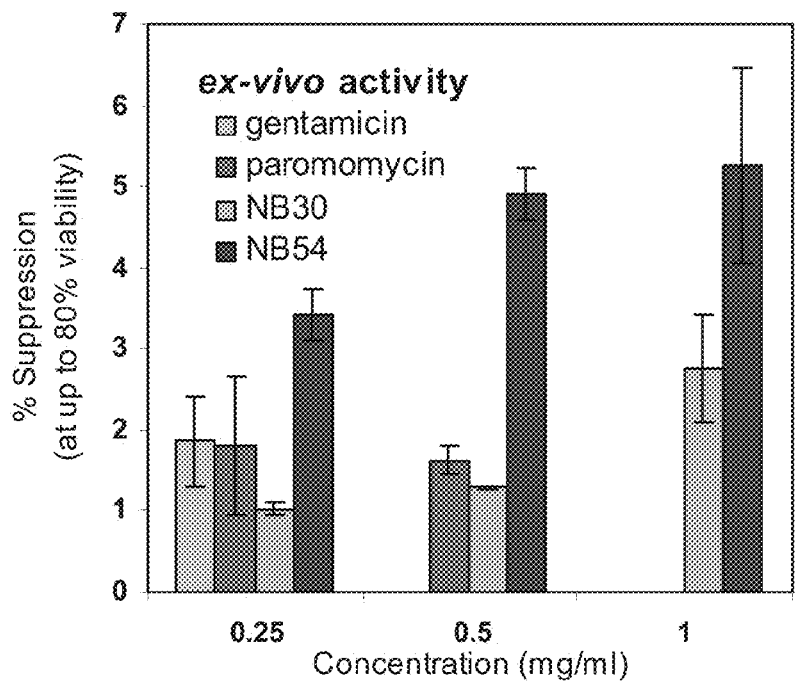
Figure 7:
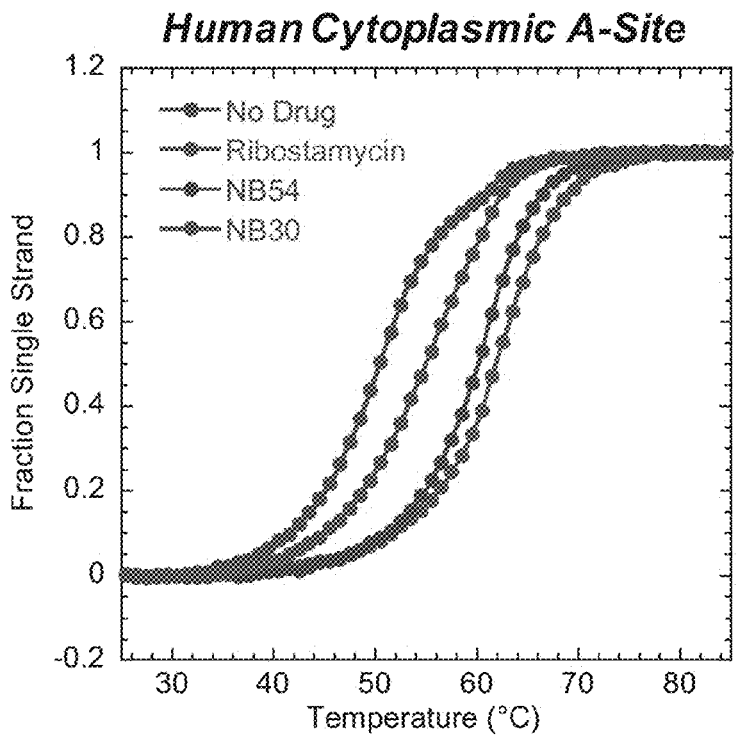
Figure 10:
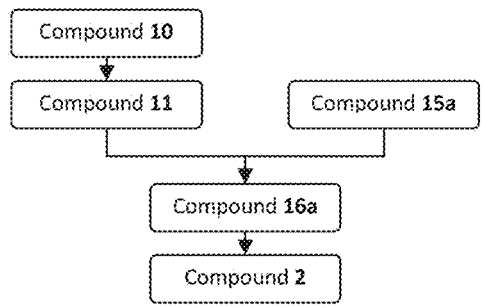
Figure 11:
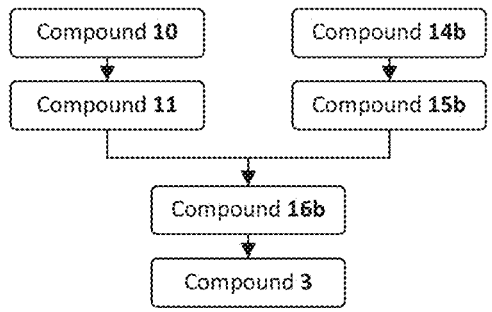
Figure 12:
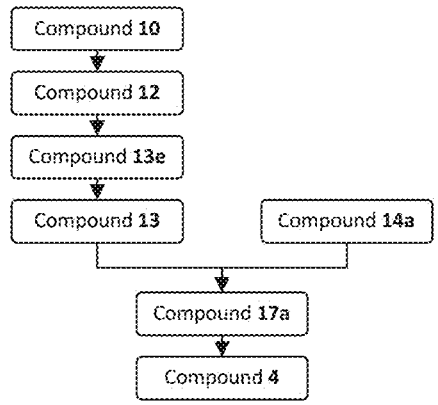
Figure 13:
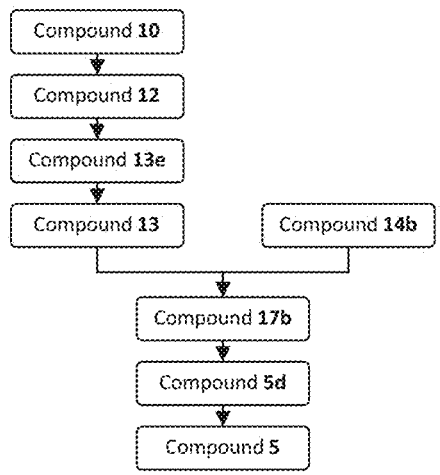
Figure 14:
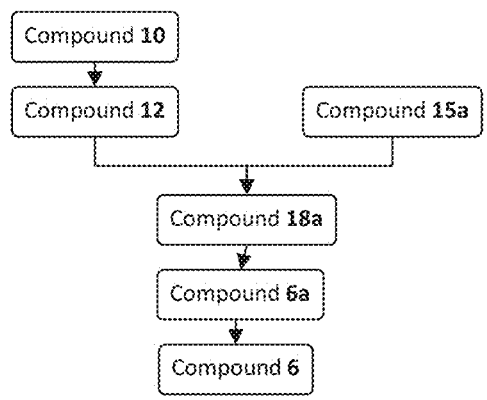
Figure 15:
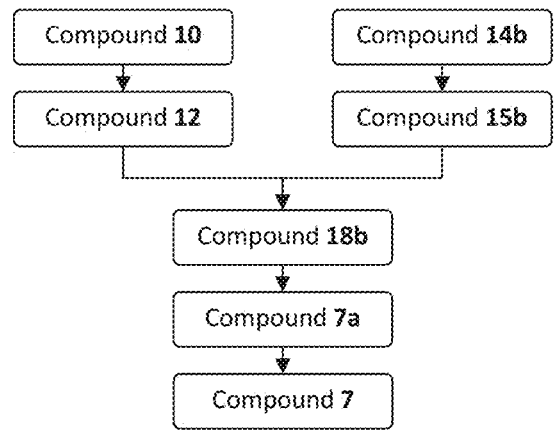
Figure 16:
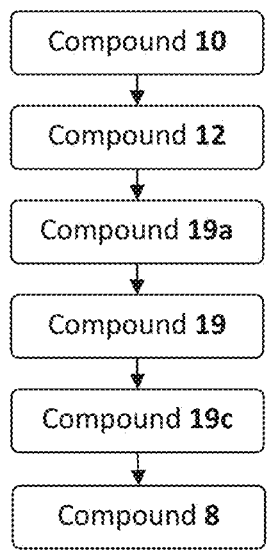

FIG. 1 presents the chemical structures of antibacterial aminoglycosides described in the background art;

FIG. 2 presents the chemical structures and general synthetic pathways for obtaining exemplary compounds according to the present embodiments, which are based on the skeleton of paromamine and were designed to exert stop-codon mutation read-trough activity and reduced toxicity as compared to other known aminoglycosides;

FIGS. 3A-3D present the results of the in vitro mutation suppression and translation comparative assays measured for an exemplary Compound 3 and paromomycin, by expression of a plasmid-based reporter construct containing a TGA C nonsense stop mutation between a 25-kDa polypeptide encoding open reading frame (ORF) and a 10-kDa polypeptide encoding ORF, in the presence of the tested compounds and [$^{35}$S]-methionine, showing the reaction products separated by SDS-PAGE and quantified using a phosphor-imager for Compound 3 (FIG. 3A) and paromomycin (FIG. 3C), and showing comparative plots where the mutation suppression values (shown in black dots) and the translation values (shown in white dots), calculated as the relative proportion of the total protein at each concentration of the tested compounds out of the total protein expressed in the absence thereof, as measured in triplicates for Compound 3 (FIG. 3B) and for paromomycin (FIG. 3D);

FIG. 4 presents the ex-vivo suppression of a nonsense mutation exhibited by an exemplary compound according to the present embodiments, Compound 3, compared with paromomycin and gentamicin, using the p2Luc plasmid containing a TGA C nonsense mutation in a polylinker between the renilla luciferase and firefly luciferase genes expressed in COS-7 cells, showing the calculated suppression levels as averages of three independent experiments or more for each tested compound at different concentrations;

FIGS. 5A-5H present the results of the in vitro stop codon suppression levels assays, induced by gentamicin (marked by black squares), paromomycin (marked by white squares), Compound 37 (marked by black circles) and Compound 3 (marked by white circles) in various nonsense mutation context constructs, p2luc (FIG. 5A), R3381X (Duchenne Muscular Dystrophy) (FIG. 5B), R3X (FIG. 5C), R245X (Usher Syndrome) (FIG. 5D), G542X (FIG. 5E), W1282X (Cystic Fibrosis) (FIG. 5F), Q70X (FIG. 5G) and W402X (Hurler Syndrome) (FIG. 5H), and the suppression level was calculated as the relation between the firefly and the renilla luciferases luminescence of the mutant and of the wild type vectors;

FIG. 6 is a comparative bar-graph, presenting the averages results of at least three independent experiments of the ex-vivo suppression assays of R3X nonsense mutation by two exemplary compounds according to the present embodiments, Compound 37 and Compound 3, as compared to paromomycin and gentamicin;

FIG. 7 presents the UV melting profiles observed for the human cytoplasmic A site olygonucleotide model duplexes in the absence of any drug (red curve in FIG. 7) and in complex with ribostamycin (blue curve in FIG. 7), Compound 3 (pink curve in FIG. 7) and Compound 37 (green curve in FIG. 7) complexes at a drug/duplex ratio of 5:1;

FIGS. 8A-8D present a comparison of $^1$H NMR spectra (FIGS. 8A and 8B) and $^{13}$C NMR spectra (FIGS. 8C and 8D) of Compound 37 prepared by the chemo-enzymatic procedure presented herein (FIGS. 8A and 8C) and by the chemical procedure presented herein (FIGS. 8B and 8D), whereas the "*" denotes unidentified impurities;

FIGS. 9A-9C present a comparison of 2D-COSY spectra of Compound 37 prepared by chemical (FIG. 9A) and chemoenzymatic (FIG. 9B) procedures presented herein, with that of the Compound 3 (FIG. 9C), whereas the dashed lines show correlations between 2-Hax and 2-Heq protons with 1-H and 3-H protons of the 2-DOS ring, highlighting strong downfield shift of the 1-H proton in Compound 37 versus 1-H proton in the parent compound Compound 3;

FIG. 10 is a flow chart depicting the preparation of Compound 2;

FIG. 11 is a flow chart depicting the preparation of Compound 3;

FIG. 12 is a flow chart depicting the preparation of Compound 4;

FIG. 13 is a flow chart depicting the preparation of Compound 5;

FIG. 14 is a flow chart depicting the preparation of Compound 6;

FIG. 15 is a flow chart depicting the preparation of Compound 7;

FIG. 16 is a flow chart depicting the preparation of Compound 8; and

Figure 17:
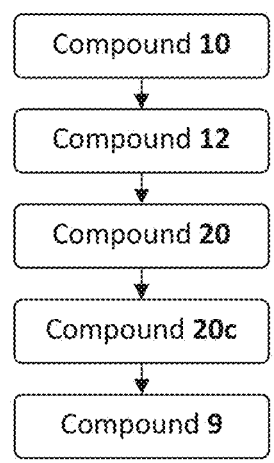

FIG. 17 is a flow chart depicting the preparation of Compound 9.

DESCRIPTION OF SPECIFIC EMBODIMENTS OF THE INVENTION

The present invention relates to a new class of aminoglycosides, which can be beneficially used in, for example, the treatment of genetic diseases. Specifically, the present invention is of a new class of compounds, derived from paromomycin, which exhibit high premature stop-codon mutations read-through activity while exerting low toxicity in mammalian cells. The present invention is thus further of pharmaceutical compositions containing these compounds, and of uses thereof in the treatment of genetic disorders, such as cystic fibrosis. The present invention is further of processes of preparing these compounds.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed above, over the past decade, many analogs of natural aminoglycosides have been designed and synthesized to overcome the rapid spread of antibiotic resistance to these drugs in pathogenic bacteria, whereby some of the antibiotic aminoglycosides have been shown to posses stop codon mutation suppression activity. However, nearly all stop codon mutation suppression experiments for the potential use of these aminoglycosides in the treatment of human genetic diseases have been performed with commercially available aminoglycosides, and almost no efforts were made to optimize the activity of these aminoglycosides as stop codon read-through inducers.

To date, there is still no clear answer to the question why some aminoglycosides induce termination suppression, while others do not. Comparison of the in-vitro suppression activity of several commercial aminoglycosides in mammalian system have shown that generally aminoglycosides with a C6' hydroxyl group on "Ring I", such as in G-418 and paromomycin (see, FIG. 1) are more effective than those with amine at the same position [6, 51].

While further exploring the effect of aminoglycosides on stop-codon mutation suppression, with the aim of finding aminoglycoside analogs that would exhibit improved stop-codon read-through activity as well as reduced toxicity, the present inventors have envisioned that separating elements of the aminoglycoside structure that induce toxicity from those that are required for an antibacterial and/or stop-codon mutation suppression activity would be beneficial to this effect. From the available toxicity data on clinically used aminoglycosides and some designed structures (see, FIG. 1), it was hypothesized that the two main factors that significantly influence the toxicity of aminoglycoside are the reduction in the number of amino groups (deamination), and/or deletion of ring hydroxyl groups (deoxygenation).

Reduced toxicity of aminoglycoside as a result of deamination (removal of amino groups) was observes in, for example, paromomycin, which differs from neomycin in that it has one less amino group, and is much less toxic than neomycin ($LD_{50}$ of neomycin=24, paromomycin=160). Thus, this difference of one charge (in terms of a positively charged amine group at physiological pH) makes a great difference in the toxicity of the two compounds. Similarly, one charge difference of kanamycin B ($LD_{50}$=132) from kanamycin A ($LD_{50}$=280) and kanamycin C ($LD_{50}$=225) rendered the latter two less toxic than kanamycin B. Without being bound by any particular theory, it has been assumed that such reduction in the toxicity of aminoglycosides upon decrease in charged amino groups can be explained by decrease of nonspecific interaction with other cell components, and by the reduced production of free radicals. An additional factor that has been noted to affect the toxicity of aminoglycosides is acylation of N1-amine of the 2-DOS ring with (S)-4-amino-2-hydroxybutyryl (AHB) group, although the extent of this effect has been shown to depend on the aminoglycoside structure (for example, neamine $LD_{50}$=125 vs N1-AHB-neamine $LD_{50}$=260; and kanamycin A $LD_{50}$=280 vs amikacin $LD_{50}$=300).

Increased toxicity of aminoglycosides as a result of a deoxygenation (removal of hydroxyl groups) was observed in, for example, the removal of 3'-OH in kanamycin B ($LD_{50}$=132) to afford tobramycin ($LD_{50}$=79), which is much more toxic than the parent kanamycin B. Without being bound by any particular theory, this phenomenon can be explained by reduction in the basicity of the 2'-NH$_2$ adjacent to the 3'-OH. Corroborating results have been provided by displacement of the 5-OH with 5-fluorine in kanamycin B and its several clinical derivatives [68-70]. Thus, significantly high toxicity of the clinical drugs such as tobramycin (3'-deoxy), gentamicin (3',4'-dideoxy), dibekacin (3',4'-dideoxy) and arbekacin (3',4'-dideoxy) could be ascribed to the increased basicity of 2-NH$_2$ group ("Ring I") in these drugs caused mainly because the lack of C3'-oxygen or C3',C4'-oxygen atoms.

The structural manipulations which were introduced into the aminoglycoside analogs presented in U.S. patent application Ser. No. 11/073,649 include, inter alia, the addition of a rigid sugar ring. The addition of a rigid sugar ring to the aminoglycoside scaffold affected the interaction thereof with resistance-causing enzymes, and therefore contributed to the inhibition of the formation of a ternary complex required for enzymatic catalysis and the subsequent emergence of resistance.

While reducing the present invention to practice, the present inventors designed and successfully prepared and practiced novel compounds which exhibit efficient mutation suppression activity and reduced toxicity. These compounds are based on a paromamine scaffold, obtained from paromomycin by removing two monosaccharide moieties therefrom, to which new structural features were introduced. The manipulations of the structural features of paromomycin were carefully selected in order to reduce potential toxicity and improve mutation read-through activity.

Hence, according to one aspect of the present invention there is provided a compound having a general Formula I:

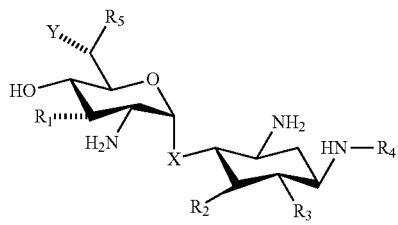

Formula I wherein:
the dashed line indicates an R configuration or an S configuration;
each of $R_1$, $R_2$ and $R_3$ is independently a monosaccharide moiety, halide, hydroxyl, amine or an oligosaccharide moiety,
X is oxygen or sulfur;
$R_4$ is hydrogen or an (S)-4-amino-2-hydroxybutyryl (AHB) moiety;
$R_5$ is hydroxyl or amine; and
Y is hydrogen, alkyl or aryl.

The term "monosaccharide", as used herein and is well known in the art, refers to a simple form of a sugar that consists of a single saccharide molecule which cannot be further decomposed by hydrolysis. Most common examples of monosaccharides include glucose (dextrose), fructose, galactose, and ribose. Monosaccharides can be classified according to the number of carbon atoms of the carbohydrate, i.e., triose, having 3 carbon atoms such as glyceraldehyde and dihydroxyacetone; tetrose, having 4 carbon atoms such as erythrose, threose and erythrulose; pentose, having 5 carbon atoms such as arabinose, lyxose, ribose, xylose, ribulose and xylulose; hexose, having 6 carbon atoms such as allose, altrose, galactose, glucose, gulose, idose, mannose, talose, fructose, psicose, sorbose and tagatose; heptose, having 7 carbon atoms such as mannoheptulose, sedoheptulose; octose, having 8 carbon atoms such as 2-keto-3-deoxy-manno-octonate; nonose, having 9 carbon atoms such as sialose; and decose, having 10 carbon atoms. Monosaccharides are the building blocks of oligosaccharides like sucrose (common sugar) and other polysaccharides (such as cellulose and starch).

As used herein, the phrase "moiety" describes a part, and preferably a major part, of a chemical entity, such as a molecule or a group, which has underwent a chemical reaction and is now covalently linked to another molecular entity.

As used herein, the term "halide" (also referred to herein as "halo"), describes an atom of fluorine, chlorine, bromine or iodine, also referred to herein as fluoride, chloride, bromide and iodide.

The term "hydroxyl", as used herein, refers to an —OH group.

As used herein, the term "amine" describes a —NR'R" group where each of R' and R" is independently hydrogen, alkyl, cycloalkyl, heteroalicyclic, aryl or heteroaryl, as these terms are defined herein.

As used herein, the term "alkyl" describes an aliphatic hydrocarbon including straight chain and branched chain groups. Preferably, the alkyl group has 1 to 20 carbon atoms, and more preferably 1-10 carbon atoms. Whenever a numerical range; e.g., "1-10", is stated herein, it implies that the group, in this case the alkyl group, may contain 1 carbon atom, 2 carbon atoms, 3 carbon atoms, etc., up to and including 10 carbon atoms. The alkyl can be substituted or unsubstituted. When substituted, the substituent can be, for example, an alkyl, an alkenyl, an alkynyl, a cycloalkyl, an aryl, a heteroaryl, a halide, a hydroxy, an alkoxy and a hydroxyalkyl as these terms are defined hereinbelow. The term "alkyl", as used herein, also encompasses saturated or unsaturated hydrocarbon, hence this term further encompasses alkenyl and alkynyl.

The term "alkenyl" describes an unsaturated alkyl, as defined herein, having at least two carbon atoms and at least one carbon-carbon double bond. The alkenyl may be substituted or unsubstituted by one or more substituents, as described hereinabove.

The term "alkynyl", as defined herein, is an unsaturated alkyl having at least two carbon atoms and at least one carbon-carbon triple bond. The alkynyl may be substituted or unsubstituted by one or more substituents, as described hereinabove.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted by one or more substituents, as described hereinabove.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted by one or more substituents, as described hereinabove. Representative examples are thiadiazole, pyridine, pyrrole, oxazole, indole, purine and the like.

The two-ring structure presented in Formula I above is referred to herein as a paromamine scaffold.

According to some embodiments of the present invention, X is oxygen.

In some embodiments, $R_5$ is hydroxyl.

In some embodiments, Y is hydrogen or alkyl, and more preferably Y is methyl.

In one embodiment of the present invention, the paromamine scaffold presented in Formula I above comprises one or more additional monosaccharide moiety or moieties attached thereto.

As can be seen in Formula I hereinabove, there are several positions onto which a monosaccharide moiety can be attached to the paromamine scaffold. According to some embodiments, there are three positions, denoted as $R_1$, $R_2$ and $R_3$, which are preferred for introducing a monosaccharide moiety to the paromamine scaffold.

In one embodiment, at least one of $R_1$, $R_2$ and $R_3$ is a monosaccharide moiety.

In some embodiments, only one monosaccharide is introduced to any one of $R_1$, $R_2$ or $R_3$. In such cases, preferably, the other positions are hydroxyls.

In some embodiments, the monosaccharide moiety is introduced at the $R_1$ position, and $R_2$ and $R_3$ are preferably each hydroxyl.

Similarly, when a monosaccharide moiety is introduced at the $R_2$ position, $R_1$ and $R_3$ are preferably each hydroxyl, and when a monosaccharide moiety is introduced at the $R_3$ position, $R_1$ and $R_2$ are preferably each hydroxyl.

According to some embodiments, at least one of $R_1$, $R_2$ and $R_3$ is a monosaccharide moiety. Preferably the monosaccharide is a pentose, such as a furanose, or a hexose, such as a pyranose. Preferred monosaccharide moieties according to the present embodiments can be collectively represented by the general Formula II:

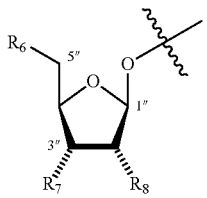

Formula II wherein each of $R_6$, $R_7$ and $R_8$ is independently selected from the group consisting of hydroxyl and amine, and the dashed line indicates an R configuration or an S configuration. The curved line indicates the position of the monosaccharide moiety that is coupled to the paromamine scaffold.

In some embodiments, $R_7$ and $R_8$ are each hydroxyl.

As presented and demonstrated in the Examples section that follows (see, Table 18), the substituent at the $R_6$ position was found to affect both the truncation mutation read-though activity and the antimicrobial activity of the resulting compound. Preferred compounds having a monosaccharide moiety represented by Formula II above therefore have an amine or hydroxyl group at the $R_6$ position, and more preferably, an amine.

In one embodiment of the present invention, the paromamine scaffold presented in Formula I above comprises one or more additional oligosaccharide moiety or moieties attached thereto, preferably at positions $R_1$, $R_2$ and $R_3$.

Hence, according to preferred embodiments, at least one of $R_1$, $R_2$ and $R_3$ is an oligosaccharide moiety. Preferably, only one oligosaccharide moiety is introduced to any one of $R_1$, $R_2$ or $R_3$. In such cases, preferably, the other positions are hydroxyls.

Preferably, the oligosaccharide moiety is attached to the $R_1$ position while the other two positions, $R_2$ and $R_3$, are preferably each hydroxyl. Alternatively, the oligosaccharide moiety is coupled to the $R_2$ position, and preferably, $R_1$ and $R_3$ are each hydroxyl, or the oligosaccharide moiety is coupled to the $R_3$ position, and preferably, $R_1$ and $R_2$ are each hydroxyl.

The term "oligosaccharide" as used herein refers to a compound that comprises two or more monosaccharide units, as these are defined herein. Preferably, the oligosaccharide comprises 2-6 monosaccharides, more preferably the oligosaccharide comprises 2-4 monosaccharides and most preferably the oligosaccharide is a disaccharide moiety, having two monosaccharide units.

According to some embodiments, the disaccharide coupled to the compound having general Formula I, has general Formula I* as follows:

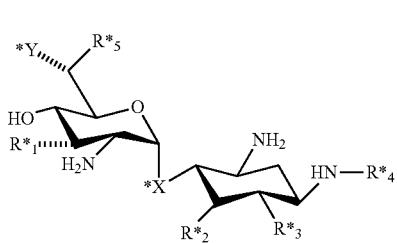

Formula I* wherein:

the dashed line indicates an R configuration or an S configuration;

each of $R^*_1$, $R^*_2$ and $R^*_3$ is independently a halide, hydroxyl, amine or is linked to the compound having general Formula I, whereas at least one of $R^*_1$, $R^*_2$ and $R^*_3$ is linked to the compound having the general Formula I.

$X^*$ is oxygen or sulfur;

$R^*_4$ is hydrogen or an (S)-4-amino-2-hydroxybutyryl (AHB) moiety;

$R^*_5$ is hydroxyl or amine; and $Y^*$ is hydrogen, alkyl or aryl.

Such a "dimer" therefore includes two compounds attached to one another at their corresponding $R_1$,$R^*_1$, $R_2$, $R^*_2$, $R_3$ or $R^*_3$ positions in any combination thereof, for example, an $R_1$-$R^*_2$ or $R_2$-$R^*_1$ linked dimer, an $R_1$-$R^*_3$ or $R_3$-$R^*_1$ linked dimer, an $R_3$-$R^*_2$ or $R_2$-$R^*_3$ linked dimer, an $R_1$-$R^*_1$ linked dimer, an $R_2$-$R^*_2$ linked dimer or an $R_3$-$R^*_3$ linked dimer. Preferably it is an $R_1$-$R^*_1$ linked dimer.

The link between the two moieties can be via a linker, or a linking moiety.

The term "linker", as used herein refers to a chemical moiety which is attached to at least two other chemical moieties, hence linking therebetween. In the context of the present embodiments the linker is preferably a low alkyl having 1-6 carbon atoms and more preferably a methylene.

As discussed hereinabove, although increasing the number of amine groups on the paromamine scaffold may have a negative effect in terms of toxicity, a paromamine analog, having an amine group at the $R_1$ position in an inversed stereochemistry as compared to the original displaced hydroxyl group, was prepared as presented in the Examples section that follows, in an attempt to investigate the effect of an additional amine in an inverted configuration.

As demonstrated in the Examples section that follows, Compound 8, an exemplary compound according to the present embodiments, having an amine at the $R_1$ position which replaces a hydroxyl and possesses an inverted configuration was prepared and exhibited 6-16 fold lower antimicrobial activity (see, Table 18 hereinbelow) as compared to paromomycin.

Hence, in another embodiment of the present invention, $R_1$ is amine. Preferably, $R_2$ and $R_3$ are each hydroxyl.

The compounds described hereinabove can be further grouped into several subsets, according to the substituents at the $R_4$, $R_5$ and Y positions. As defined hereinabove, $R_4$ can be hydrogen or an (S)-4-amino-2-hydroxybutyryl (AHB) moiety, $R_5$ can be hydroxyl or amine, and Y can be hydrogen or alkyl (preferably methyl) giving together six preferred subsets of compounds with respect to $R_4$ $R_5$ and Y.

Considering $R_4$, $R_5$ and Y, in one subset each of $R_4$ and Y is hydrogen, and $R_5$ is hydroxyl, giving the compounds shown in FIG. 2. In the other two subsets in this respect $R_4$ is either hydrogen or AHB and there is an amine at the $R_5$ position and a methyl at the Y position, and in each of these compounds the $R_5$ position can assume either the R or the S stereo-configuration.

Each of the above subsets can be further divided by its $R_4$ substituent, being either hydrogen, or an AHB moiety. Alternatively the AHB moiety can be replaced by an α-hydroxy-β-aminopropionyl (AHP) moiety.

In some embodiments of the present invention, the compound has general Formula I above and a monosaccharide moiety (e.g., a ribofuranose) as one of $R_1$, $R_2$ or $R_3$.

Compounds having general Formula I above, in which Y is hydrogen, $R_4$ is hydrogen or an AHB moiety and one of $R_1$-$R_3$ is a ribofuranose or pyranose moiety, are also referred to herein as Compounds 3 and 37-41 (see, Scheme 7 hereinbelow); Compounds having general Formula I above, in which $R_5$ is hydroxyl, $R_4$ is hydrogen or an AHB moiety, one of $R_1$-$R_3$ is a ribofuranose or pyranose moiety, and Y is methyl, are also referred to herein as Compounds 42-47 (see, Scheme 8 hereinbelow); and Compounds having general Formula I above, in which $R_5$ is amine, $R_4$ is hydrogen or an AHB moiety, Y is methyl and one of $R_1$-$R_3$ is a ribofuranose or pyranose moiety, are also referred to herein as Compounds 48-53 (see, Scheme 8 hereinbelow).

According to some of the present embodiments, (3S,4R,5S,6S)-5-amino-6-((1R,2R,3R,4R)-4,6-diamino-2-((2S,4R,5R)-3,4-dihydroxy-5-(hydroxymethyl)-tetrahydrofuran-2-yloxy)-3-hydroxycyclohexyloxy)-2-(hydroxymethyl)-tetrahydro-2H-pyran-3,4-diol (referred to hereinbelow as Compound 2), (3S,4R,5S,6S)-5-amino-6-((1R,2S,3R,4R)-4,6-diamino-3-((2R,4R,5R)-3,4-dihydroxy-5-(hydroxymethyl)-tetrahydrofuran-2-yloxy)-2-hydroxycyclohexyloxy)-2-(hydroxymethyl)-tetrahydro-2H-pyran-3,4-diol (referred to hereinbelow as Compound 4), amikacin, apramycin, arbekacin, butirosin, dibekacin, fortimycin, G-418, gentamicin, hygromycin, habekacin, dibekacin, netlmicin, istamycin, isepamycin, kanamycin, lividomycin, neamine, neomycin, paromomycin, ribostamycin, sisomycin, spectinomycin, streptomycin, tobramycin and any variants thereof having a suffix added their name, such as, for example, gentamicin C1, gentamicin C1A, gentamicin C2, gentamicin D, kanamycin A, kanamycin B, butirosin A, hygromycin B, neomycin B, etc., have been previously described and are therefore excluded from the scope of this aspect of the present invention. These also include any other aminoglycoside analogs having two or more monosaccharide units, which have been previously described.

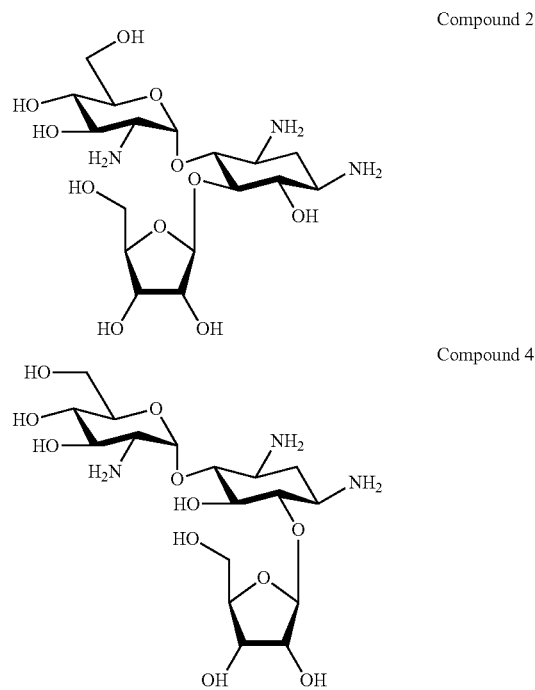

Nonetheless, Compound 2 and Compound 4, were neither described nor tested in the context of their therapeutic activity in general, let alone in the context of treatment of genetic disorders, and in the context of stop-codon mutation suppression in particular, and are therefore not excluded from the scope of other aspects of the present invention.

The present embodiments further encompass any enantiomers, prodrugs, solvates, hydrates and/or pharmaceutically acceptable salts of the compounds described herein.

As used herein, the term "enantiomer" refers to a stereoisomer of a compound that is superposable with respect to its counterpart only by a complete inversion/reflection (mirror image) of each other. Enantiomers are said to have "handedness" since they refer to each other like the right and left hand. Enantiomers have identical chemical and physical properties except when present in an environment which by itself has handedness, such as all living systems.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. A prodrug may also have improved solubility as compared with the parent drug in pharmaceutical compositions. Prodrugs are also often used to achieve a sustained release of the active compound in vivo. An example, without limitation, of a prodrug would be a compound of the present invention, having one or more carboxylic acid moieties, which is administered as an ester (the "prodrug"). Such a prodrug is hydrolyzed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the compound of the present invention) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. An example, without limitation, of a pharmaceutically acceptable salt would be a carboxylate anion and a cation such as, but not limited to, ammonium, sodium, potassium and the like.

Further according to the present invention, there are provided processes of preparing the compounds described herein.

The synthetic pathways described herein include a reaction between an acceptor and a donor, whereby the term "acceptor" is used herein to describe the skeletal structure derived from paromamine which has at least one and preferably selectively selected available (unprotected) hydroxyl group at positions such as C5, C6 and C3', which is reactive during a glycosidation reaction, and can accept a glycosyl, and the term "donor" is used herein to describe the glycosyl.

The term "glycosyl", as used herein, refers to a chemical group which is obtained by removing the hydroxyl group from the hemiacetal function of a monosaccharide and, by extension, of a lower oligosaccharide.

The donors and acceptors are designed so as to form the desired compounds. The following describes some embodiments of this aspect of the present invention, presenting exemplary processes of preparing exemplary subsets of the compounds described herein.

The syntheses of the compounds of the present embodiments generally include (i) preparing an acceptor compound by selective protection of one or more hydroxyls and amines at selected positions present on the paromamine scaffold, leaving one or two positions unprotected and therefore free to accept a donor (glycosyl) compound as defined hereinabove; (ii) manipulating a structural feature of the acceptor at the desired position, by e.g., a coupling reaction with a suitably protected donor compound to the unprotected position on the acceptor, or by replacing a hydroxyl group with an amine group and optionally inversing the configuration of the amine; and (iii) removing of all protecting groups.

The phrase "protecting group", as used herein, refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include azide (azido), N-phthalimido, N-acetyl, N-trifluoroacetyl, N-t-butoxycarbonyl (BOC), N-benzyloxycarbonyl (CBz) and N-9-fluorenylmethylenoxycarbonyl (Fmoc). Similarly, a "hydroxyl-protecting group" refers to a substituent of a hydroxyl group that blocks or protects the hydroxyl functionality. Suitable protecting groups include cyclohexanone dimethyl ketal (forming a 1,3-dioxane with two adjacent hydroxyl groups), 4-methoxy-1-methylbenzene (forming a 1,3-dioxane with two adjacent hydroxyl groups), O-acetyl, O-chloroacetyl, O-benzoyl and O-silyl. For a general description of protecting groups and their use, see T. W. Greene, Protective Groups in Organic Synthesis, John Wiley & Sons, New York, 1991.

According to the embodiments presented hereinbelow, the amine protecting groups include an azide group and/or an N-phthalimide group, and the hydroxyl-protecting groups include O-acetyl, O-chloroacetyl and/or O-benzoyl.

In one embodiment, there is provided a process of preparing an exemplary subset of the compounds having the general Formula I as presented herein, wherein a monosaccharide is attached to the $R_1$ position and $R_2$ and $R_3$ are each hydroxyl. The process, according to this embodiment, is effected by preparing a suitably protected acceptor compound and a suitably protected donor compound, coupling these two compounds to one another, and subsequently removing all the protecting groups from the resulting compound.

The acceptor, according to this embodiment, has the general Formula III:

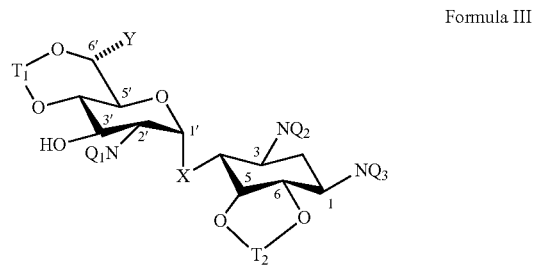

Formula III which is a version of paromamine having protecting groups at specific positions, wherein:

the dashed line indicates an R configuration or an S configuration;

Y is hydrogen, alkyl or aryl;

each of $T_1$-$T_2$ is independently a hydroxyl protecting group;

each of $Q_1$ and $Q_2$ is independently an amine protecting group;

$Q_3$ is selected from the group consisting of an amine protecting group and an AHB moiety, in which the amine and hydroxyl groups are protected; and X is oxygen or sulfur, preferably oxygen.

The protecting groups are selected such that they are easily attached and removed under suitable conditions, and according to the differential reactivity of the various amine and hydroxyl groups of paromamine, such that the hydroxyl group at the $R_1$ position thereof is left unprotected and free for the coupling reaction.

According to some embodiments, each of $T_1$-$T_2$ is a cyclohexanone dimethyl ketal protecting group, forming a 1,3-dioxane with two adjacent hydroxyl groups in the case of $T_1$, and forming a 1,3-dioxolane in the case of $T_2$.

The donor compound is a protected monosaccharide having a leaving group at position 1" thereof. Such protected monosaccharides can be collectively represented by the general Formula VI:

Formula VI

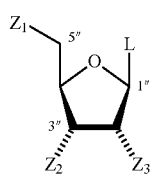

wherein each of $Z_1$, $Z_2$ and $Z_3$ is independently selected from the group consisting of a hydroxyl protecting group and a amine protecting group, L is the leaving group, and the dashed line indicates an R configuration or an S configuration.

As used herein, the phrase "leaving group" describes a labile atom, group or chemical moiety that readily undergoes detachment from an organic molecule during a chemical reaction, while the detachment is facilitated by the relative stability of the leaving atom, group or moiety thereupon. Typically, any group that is the conjugate base of a strong acid can act as a leaving group. Representative examples of suitable leaving groups according to the present embodiments therefore include, without limitation, halide, acetate, tosylate, triflate, sulfonate, azide, hydroxy, thiohydroxy, alkoxy, cyanate, thiocyanate, nitro and cyano.

The term "acetate" refers to acetic acid anion.

The term "tosylate" refers to toluene-4-sulfonic acid anion.

The term "triflate" refers to trifluoro-methanesulfonic acid anion.

The term "azide" refers to an $N_3^-$.

The terms "hydroxy" and "thiohydroxy" refer to the OH$^-$ and SH$^-$ anions respectively.

The term "cyanate" and "thiocyanate" refer to [O=C=N]$^-$ and [S=C=N]$^-$ anions respectively.

The term "nitro" refers to $NO_2^-$.

The term "cyano" refers to [C≡N]$^-$.

Preferably L is p-tolylsulfide (p-thiotoluene), thioethyl and trichloroacetimidate, and further preferably each of $Z_1$-$Z_3$ is a hydroxyl protecting group.

The process is therefore effected by:

(a) coupling the abovementioned acceptor compound to the abovementioned donor compound; and (b) subsequently removing each of the protecting groups.

Exemplary compounds which were prepared according to this embodiment include Compound 6 and Compound 7, as presented in the Examples section that follows.

This rudimentary process is used to prepare other exemplary subsets of the compounds according to the present embodiments, upon utilizing an acceptor that is designed to interact with a donor at a desired position.

Hence, according to another embodiment, there is provided a process of preparing an exemplary subset of the compounds having the general Formula I as presented herein, wherein a monosaccharide is attached to the $R_2$ position and $R_1$ and $R_3$ are each hydroxyl. Such a process is effected by:

(a) coupling a compound having the general Formula IV:

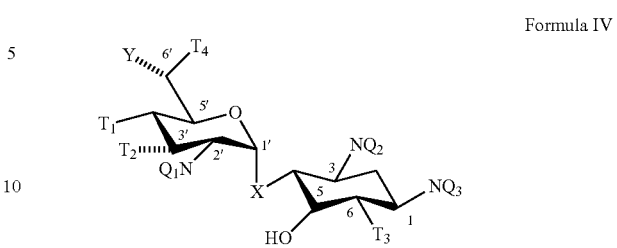

Formula IV wherein:
the dashed line indicates an R configuration or an S configuration;
Y is hydrogen, alkyl or aryl;
each of $T_1$-$T_4$ is independently a hydroxyl protecting group;
each of $Q_1$ and $Q_2$ is independently an amine protecting group;
$Q_3$ is selected from the group consisting of an amine protecting group and an AHB moiety, the AHB moiety comprises at least one of a hydroxyl protecting group and an amine protecting group; and
X is oxygen or sulfur,
with a derivative of a monosaccharide having a leaving group attached at position 1" thereof and at least one of a hydroxyl protecting group and an amino protecting group; and (b) removing each of the hydroxyl protecting groups and the amine protecting groups, to thereby obtain the compound.

Preferably, each of $T_1$-$T_4$ is O-acetyl.

As in the previously presented embodiment, the derivative of a monosaccharide is a protected monosaccharide that has the general Formula VI, as presented hereinabove.

Exemplary compounds which were prepared according to this embodiment include Compound 2, Compound 3 and Compound 37, as presented in the Examples section that follows.

According to yet another embodiment there is provided a process of preparing an exemplary subset of the compounds having the general Formula I as presented herein, wherein a monosaccharide is attached to the $R_3$ position and $R_1$ and $R_2$ are each hydroxyl. Such a process is effected by:

(a) coupling a compound having the general Formula V:

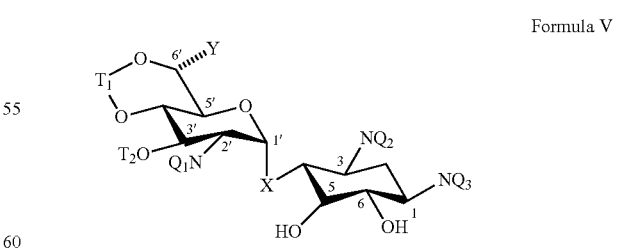

Formula V wherein:
the dashed line indicates an R configuration or an S configuration;
Y is hydrogen, alkyl or aryl;
each of $T_1$-$T_2$ is independently a hydroxyl protecting group;

each of $Q_1$ and $Q_2$ is independently an amine protecting group;

$Q_3$ is selected from the group consisting of an amine protecting group and an AHB moiety, the AHB moiety comprises at least one of a hydroxyl protecting group and an amine protecting group; and X is oxygen or sulfur, with a derivative of a monosaccharide having a leaving group attached at position 1" thereof and at least one of a hydroxyl protecting group and an amino protecting group; and (b) removing each of the hydroxyl protecting groups and the amine protecting groups, to thereby obtain the compound.

Preferably, $T_1$ is 4-methoxy-1-methylbenzene and $T_2$ is O-benzoyl.

Exemplary compounds which were prepared according to this embodiment include Compound 4 and Compound 5, as presented in the Examples section that follows.

In other embodiments, the acceptors presented hereinabove are utilized in the preparation of other subsets of compounds having general Formula I.

Thus, in still another embodiment, there is provided a process of preparing a compound having the general Formula I as presented hereinabove, wherein $R_1$ is amine which exhibits an inverted stereo configuration as compared to the corresponding hydroxyl group in the parent paromamine compound, and $R_2$ and $R_3$ are each hydroxyl. Such a process is effected by:

(a) reacting a compound having the general Formula III:

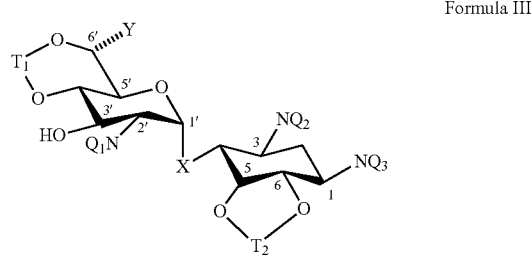

Formula III wherein:

the dashed line indicates an R configuration or an S configuration;

Y is hydrogen, alkyl or aryl;

each of $T_1$-$T_2$ is independently a hydroxyl protecting group;

each of $Q_1$ and $Q_2$ is independently an amine protecting group;

$Q_3$ is selected from the group consisting of an amine protecting group and an AHB moiety, the AHB moiety comprises at least one of a hydroxyl protecting group and an amine protecting group; and X is oxygen or sulfur, with triflic anhydride to thereby obtain a trifluoro-methanesulfonate group at position 3' thereof;

(b) reacting the compound having the trifluoro-methanesulfonate group at position 3' thereof with sodium azide; and (c) removing each of the hydroxyl protecting groups and the amine protecting groups, thereby obtaining the compound having an amine at the $R_1$ position.

An exemplary compound which was prepared according to this embodiment includes Compound 8, as presented in the Examples section that follows.

According to an additional embodiment, there is provided a process of preparing a dimer compound having the general Formula I as presented hereinabove, wherein $R_1$ is the disaccharide moiety having the general Formula I* described hereinabove, and $R_2$ and $R_3$ are each hydroxyl. Such a process is effected by:

(a) coupling a compound having the general Formula III with another compound having the general Formula III*:

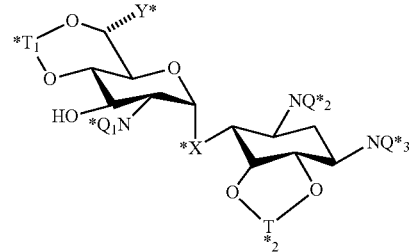

Formula III* wherein:

the dashed line indicates an R configuration or an S configuration;

Y* is hydrogen, alkyl or aryl;

each of $T^*_1$-$T^*_2$ is independently a hydroxyl protecting group;

each of $Q^*_1$ and $Q^*_2$ is independently an amine protecting group;

$Q^*_3$ is selected from the group consisting of an amine protecting group and an AHB moiety, the AHB moiety comprises at least one of a hydroxyl protecting group and an amine protecting group; and X* is oxygen or sulfur; and (b) removing each of the hydroxyl protecting groups and the amine protecting groups, thereby obtaining the dimer compound.

The dimer compound can be a homodimer compound, wherein the two disaccharides are identical to one another (namely, Y, X, $Q_1$, $Q_2$, $Q_3$, $T_1$ and $T_2$ and Y*, X*, $Q^*_1$, $Q^*_2$, $Q^*_3$, $T^*_1$ and $T^*_2$, respectively, are identical, or a heterodimer wherein the two disaccharides are different in one or more features therein.

According to other preferred embodiments of this aspect, the coupling is effected via a linker, as this term is defined hereinabove. Preferably the linker is an alkyl, more preferably a low alkyl and most preferably the linker is a methylene group.

Thus, the coupling is effected in the presence of a bifunctional compound, preferably a bifunctional alkyl (e.g., methylene), which reacts with the two free (unprotected) hydroxyl groups to thereby affect the coupling therebetween. Such a bifunctional compound preferably has two leaving groups, as defined herein.

An exemplary compound which was prepared according to this embodiment includes Compound 9, as presented in the Examples section that follows.

According to another aspect of the present invention, there is provided a process of preparing a compound having a general Formula I:

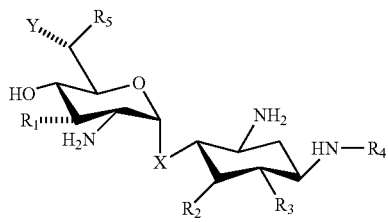

Formula I wherein:

each of $R_1$, $R_2$ and $R_3$ is independently a monosaccharide moiety, halide, hydroxyl, amine or an oligosaccharide moiety, X is oxygen or sulfur;

$R_4$ is (S)-4-amino-2-hydroxybutyryl (AHB);

$R_5$ is hydroxyl or amine;

Y is hydrogen, alkyl or aryl;

the dashed line indicates an R configuration or an S configuration;

using a chemo-enzymatic reaction.

The process, according to this aspect of the present invention, is effected by reacting a precursor compound having the general Formula I wherein $R_4$ is hydrogen, with γ-L-Glu-AHB-SNAC in the presence of the purified enzyme BtrH, to thereby obtain an intermediate compound having the general Formula I wherein $R_4$ is a γ-L-Glu-AHB. This intermediate compound is used, preferably without further purification, in the next enzymatic reaction with the purified enzyme BtrG, to thereby obtain the compound having the general Formula I wherein $R_4$ is (S)-4-amino-2-hydroxybutyryl (AHB).

This process was used as a alternative process for preparing exemplary Compound 37, as presented in the Examples section that follows.

As demonstrated in the Examples section that follows, the compounds presented herein were designed so as to, and were indeed shown to, possess a truncation mutation suppression activity, namely the ability to induce read-through of a stop-codon mutation. Such an activity renders these compounds suitable for use as therapeutically active agents for the treatment of genetic disorders, and particularly such disorders which are characterized by a truncation mutation.

Thus, according to another aspect of the present invention there is provided a method of treating a genetic disorder. The method, according to this aspect of the present invention, is effected by administering to a subject in need thereof a therapeutically effective amount of one or more of the compounds presented herein having a general Formula I.

Excluded from the scope of this aspect of the present invention are amikacin, apramycin, arbekacin, butirosin, dibekacin, fortimycin, G-418, gentamicin, hygromycin, habekacin, dibekacin, netlmicin, istamycin, isepamycin, kanamycin, lividomycin, neamine, neomycin, paromomycin, ribostamycin, sisomycin, spectinomycin, streptomycin and tobramycin, and any analogs or variants thereof that have been previously described, as described hereinabove.

As used herein, the terms "treating" and "treatment" include abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "therapeutically effective amount" describes an amount of the polymer being administered which will relieve to some extent one or more of the symptoms of the condition being treated.

The phrase "genetic disorder", as used herein, refers to a chronic disorder which is caused by one or more defective genes that are often inherited from the parents, and which can occur unexpectedly when two healthy carriers of a defective recessive gene reproduce, or when the defective gene is dominant. Genetic disorders can occur in different inheritance patterns which include the autosomal dominant pattern wherein only one mutated copy of the gene is needed for an offspring to be affected, and the autosomal recessive pattern wherein two copies of the gene must be mutated for an offspring to be affected.

According to preferred embodiments the genetic disorder involves a gene having a truncation mutation which leads to improper translation thereof. The improper translation causes a reduction or abolishment of synthesis of an essential protein.

Exemplary such genetic disorders include, but are not limited to, cystic fibrosis (CF), Duchenne muscular dystrophy (DMD), ataxia-telangiectasia, Hurler syndrome, hemophilia A, hemophilia B, Usher syndrome and Tay-Sachs.

Accordingly, there is provided a use of a compound having the general Formula I as presented herein in the manufacture of a medicament for treating a genetic disorder.

In any of the methods and uses described herein, the compounds described herein can be utilized either per se or form a part of a pharmaceutical composition, which further comprises a pharmaceutically acceptable carrier.

Thus, further according to the present invention, there is provided a pharmaceutical composition which comprises, as an active ingredient, any of the novel compounds described herein and a pharmaceutically acceptable carrier.

Being primarily directed at treating genetic disorders, which are chronic by definition, the compounds presented herein or pharmaceutical compositions containing the same are expected to be administered throughout the lifetime of the subject being treated. Therefore, the mode of administration of pharmaceutical compositions containing the compounds should be such that will be easy and comfortable for administration, preferably by self-administration, and such that will take the smallest toll on the patient's wellbeing and course of life.

The repetitive and periodic administration of the compounds presented herein or the pharmaceutical compositions containing the same can be effected, for example, on a daily basis, i.e. once a day, more preferably the administration is effected on a weekly basis, i.e. once a week, more preferably the administration is effected on a monthly basis, i.e. once a month, and most preferably the administration is effected once every several months (e.g., every 1.5 months, 2 months, 3 months, 4 months, 5 months, or even 6 months).

As discussed hereinabove, some of the limitations for using presently known aminoglycosides as truncation mutation read-through drugs are associated with the fact that they are primarily antibacterial (used as antibiotic agents). Chronic use of any antibacterial agents is highly unwarranted and even life threatening as it alters intestinal microbial flora which may cause or worsen other medical conditions such as flaring of inflammatory bowel disease [71], and may cause the emergence of resistance in some pathological strains of microorganisms [72-75].

The compounds presented herein preferably have no anti-bacterial activity. By "no anti-bacterial activity" it is meant that the minimal inhibition concentration (MIC) thereof for a particular strain is much higher than the concentration of a compound that is considered an antibiotic with respect to this strain. Further, preferably, the MIC of these compounds is much higher than the concentration required for exerting truncation mutation suppression activity.

Being preferably non-bactericidal, the compounds presented herein do not suffer from the aforementioned limitation and hence can be administered via absorption paths that may contain benign and/or beneficial microorganisms that are not targeted and thus their preservation may even be required. This important trait of the compounds presented herein renders these compounds particularly effective drugs against chronic conditions since they can be administered repetitively and during life time, without causing any adverse, accumulating effects, and can further be administered orally or rectally, i.e. via the GI tract, which is a very helpful and important characteristic for a drug directed at treating chronic disorders.

According to some embodiments, the compounds presented herein are selective towards eukaryotic cells versus prokaryotic cells, namely the compounds exhibit higher activity in eukaryotic cells, such as those of mammalian (humans) as compared to their activity in prokaryotic cells, such as those of bacteria. Without being bound by any particular theory, it is assumed that the compounds presented herein, which are known to act by binding to the A-site of the 16S ribosomal RNA while the robosime is involved in translating a gene, have a higher affinity to the eukaryotic ribosomal A-site, or otherwise are selective towards the eukaryotic A-site, versus the prokaryotic ribosomal A-site.

As used herein a "pharmaceutical composition" refers to a preparation of the compounds presented herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the compounds presented herein into preparations which, can be used pharmaceutically. Proper formulation is dependent upon the route of administration chosen.

According to some embodiments, the most preferred route of administration is effected orally. For oral administration, the compounds presented herein can be formulated readily by combining the compounds with pharmaceutically acceptable carriers well known in the art. Such carriers enable the compounds presented herein to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the compounds presented herein may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For injection, the compounds presented herein may be formulated in aqueous solutions, preferably in physiologically compatible buffers such as Hank's solution, Ringer's solution, or physiological saline buffer with or without organic solvents such as propylene glycol, polyethylene glycol.

For transmucosal administration, penetrants are used in the formulation. Such penetrants are generally known in the art.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active aminoglicoside compounds doses.

For buccal administration, the compositions may take the form of tablets or lozenges formulated in conventional manner.

For administration by inhalation, the compounds presented herein are conveniently delivered in the form of an aerosol spray presentation (which typically includes powdered, liquified and/or gaseous carriers) from a pressurized pack or a nebulizer, with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compounds presented herein and a suitable powder base such as, but not limited to, lactose or starch.

The compounds presented herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the compounds preparation in water-soluble form. Additionally, suspensions of the compounds presented herein may be prepared as appropriate oily injection suspensions and emulsions (e.g., water-in-oil, oil-in-water or water-in-oil in oil emulsions). Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds presented herein to allow for the preparation of highly concentrated solutions.

Alternatively, the compounds presented herein may be in powder form for constitution with a suitable vehicle, e.g., sterile, pyrogen-free water, before use.

The compounds presented herein may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of compounds presented herein effective to prevent, alleviate or ameliorate symptoms of the disorder, or prolong the survival of the subject being treated.

Determination of a therapeutically effective amount is well within the capability of those skilled in the art, especially in light of the detailed disclosure provided herein.

For any compounds presented herein used in the methods of the present embodiments, the therapeutically effective amount or dose can be estimated initially from activity assays in animals. For example, a dose can be formulated in animal models to achieve a circulating concentration range that includes the mutation suppression levels as determined by activity assays (e.g., the concentration of the test compounds which achieves a substantial read-through of the truncation mutation). Such information can be used to more accurately determine useful doses in humans.

Toxicity and therapeutic efficacy of the compounds presented herein can be determined by standard pharmaceutical procedures in experimental animals, e.g., by determining the $EC_{50}$ (the concentration of a compound where 50% of its maximal effect is observed) and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the compounds presented herein which are sufficient to maintain the desired effects, termed the minimal effective concentration (MEC). The MEC will vary for each preparation, but can be estimated from in vitro data; e.g., the concentration of the compounds necessary to achieve 50-90% expression of the whole gene having a truncation mutation, i.e. read-through of the mutation codon. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the chronic condition to be treated, dosing can also be a single periodic administration of a slow release composition described hereinabove, with course of periodic treatment lasting from several days to several weeks or until sufficient amelioration is effected during the periodic treatment or substantial diminution of the disorder state is achieved for the periodic treatment.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a compound according to the present embodiments, formulated in a compatible pharmaceutical carrier may also be prepared, placed in an appropriate container, and labeled for treatment of an indicated condition or diagnosis, as is detailed hereinabove.

Thus, in one embodiment, the pharmaceutical composition is packaged in a packaging material and identified in print, in or on the packaging material, for use in the treatment of a genetic disorder, as defined herein.

In any of the composition, methods and uses described herein, the compounds can be utilized in combination with other agents useful in the treatment of the genetic disorder.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Chemical Syntheses

Materials and Methods:

$^1$H NMR, $^{13}$C NMR, Distortionless Enhancement by Polarisation Transfer (1D DEPT), Total Correlation Spectroscopy (TOCSY), Heteronuclear Multiple-Quantum Correlation (HMQC), and Heteronuclear Multiple-Bond Correlation (HMBC) spectra were recorded on a Bruker Avance™ 500 spectrometer. Chemical shifts, reported in ppm, are relative to internal Me4Si ($\delta$=0.0) with CDCl$_3$ as the solvent, and to HOD (hydrogen on demand, $\delta$=4.63) with D$_2$O as the solvent.

Mass spectroscopy analyses were performed on a Bruker Daltonix Apex 3 mass spectrometer for Electrospray Ionization Mass Spectrometry (ESIMS) conditions, or on a TSQ-70B mass spectrometer (Finnigan Mat) MALDI Micromass spectrometer under MALDI-TOF conditions using α-cyano-4-hydroxycinnamic acid matrix.

Reactions were monitored by TLC on Silica gel (Gel 60 F$_{254}$, 0.25 mm, Merck), and spots were visualized by charring with a yellow solution containing (NH$_4$)$_6$Mo$_7$O$_{24}$.4H$_2$O (120 grams) and (NH$_4$)$_2$Ce(NO$_3$)$_6$ (5 grams) in 10% H$_2$SO$_4$ (800 ml).

Flash column chromatography was performed on Silica gel "Gel 60" (70-230 mesh).

All reactions were carried out under an argon atmosphere and using anhydrous solvents, unless otherwise indicated.

All chemicals, unless otherwise stated, were obtained from common vendors.

General Synthetic Overview:

A series of new compounds were designed according to the present embodiments for the treatment of human genetic diseases caused by premature stop mutations. All compounds were derived from paromamine which is derived from paromomycin.

Compounds 2-9 were synthesized following the paths presented in FIG. 2. As can be seen in FIG. 2, the basic syntheses involves direct Lewis acid promoted cleavage of paromomycin into the disaccharide paromamine, referred to herein as Compound 1, which is then used as a common starting material for the preparation of the designed Compounds. The protecting groups used in the below syntheses were chosen based on their ease of attachment and removal, and their stability under the reaction conditions. The glycosidation method of thioglycoside using N-iodosuccinimide (NIS) [76] and the glycosidation method of the trichloroacetimidate using BF$_3$ [77] proved to be both rapid and efficient. The benzoate ester protections at the C-2 position of the ribofuranoside donors, Compounds 14a, 14b, 15a and 15b, (see, Scheme 1 below) were specially designed to allow selective β-glycoside bond formation between "Ring III" and the paromamine moiety through neighboring group participation in Compounds 2-7.

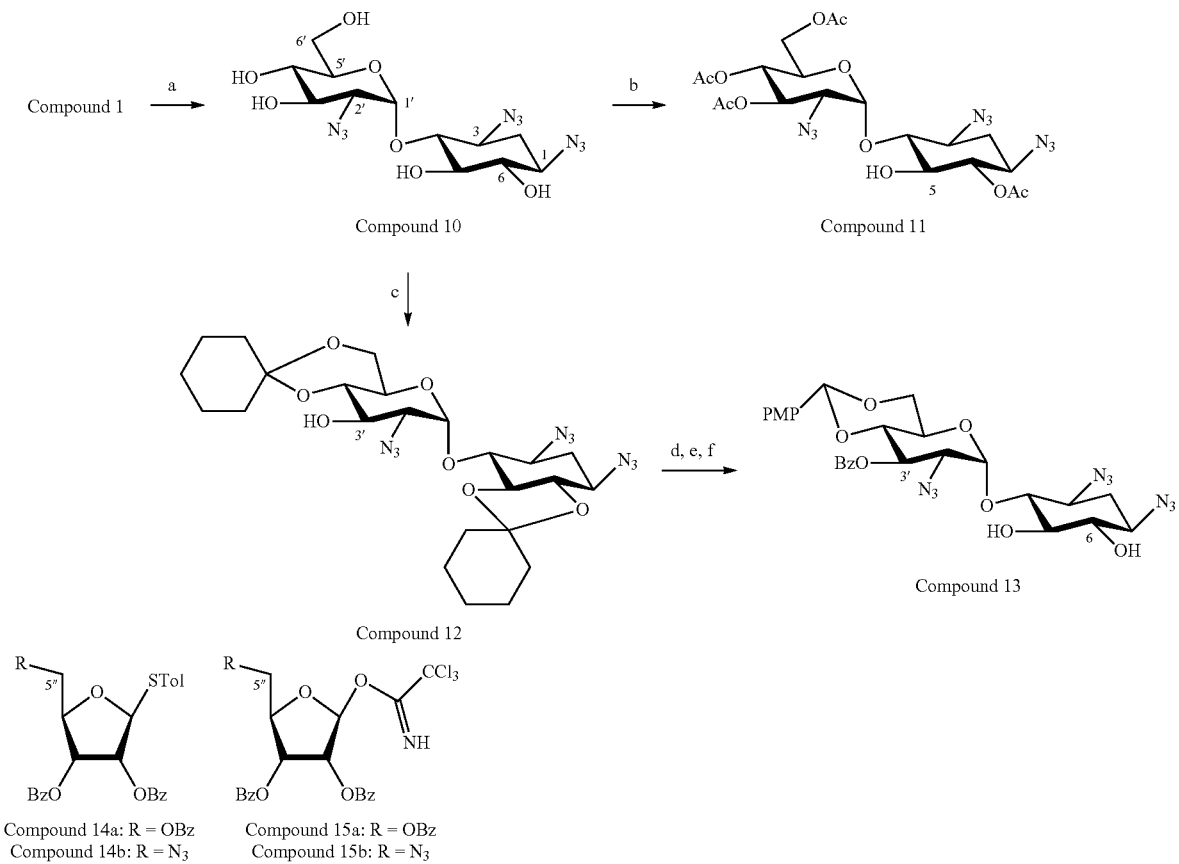

Scheme 1

The reagents and conditions seen in Scheme 1 above include: (a) TfN$_3$, Et$_3$N, CuSO$_4$, in CH$_2$Cl$_2$/MeOH/H$_2$O 3:10:3; (b) Ac$_2$O (4.2 equivalents), pyridine, −6° C.; (c) cyclohexanone dimethyl ketal, CSA, DMF, 110° C.; (d) BzCl, pyridine; (e) TFA/H$_2$O 5:3, THF, 40° C.; (f) anisaldehyde-dimethylacetal, CSA, DMF, 50° C.; and the abbreviations are: Tf=trifluoromethanesulfonyl, CSA=camphor sulfonic acid, DMF=dimethylformamide, Bz=benzoyl, TFA=trifluoroacetic acid, PMP=p-methoxyphenyl.

Preparation of Compounds 2-7 employed the appropriately protected three different paromamine acceptors, i.e. Compounds 11-13, which selectively expose the hydroxyl groups of the paromamine moiety at positions C5, C6 and C3', to glycosidation reactions, making C5 hydroxyl most susceptible for reaction and C3' hydroxyl least susceptible. These acceptor molecules were readily accessible from the paromamine (Compound 1) as illustrated in Scheme 1 above.

Regioselective acetylation of Compound 10 with acetic anhydride at low temperature gave the acceptor Compound 11 at 65% yield [78]. In another pathway, treatment of Compound 10 with cyclohexanone dimethyl ketal gave the second acceptor, Compound 12, in which all functional groups, except the hydroxyl group at position C3', were protected. Benzoylation of Compound 12 was followed by acid hydrolysis and benzylidene acetal formation steps to afford the third acceptor Compound 13 at isolated yield of 86% for all three steps.

The paromamine acceptors Compounds 11-13 were then separately subjected to glycosidation reactions with two sets of glycosyl donors, i.e., Compounds 14a-14b and Compounds 15a-b, to furnish the designed protected derivatives Compounds 16-18 at an overall yield of 68-95%, as illustrated in Scheme 2 below. As presented hereinbelow, the structures of Compounds 16-18 were confirmed by combination of various spectroscopic techniques, including HMQC, HMBC, 2D-COSY, and 1D TOCSY NMR spectroscopy. These protected compounds were then subjected to either two-steps or three-steps deprotection: removal of all the ester groups by treatment with methylamine (33% solution in EtOH), reduction of all the azide groups by the Staudinger reaction, and hydrolysis of O-benzylidine acetal and cyclohexylidene ketal with aqueous trifluoroacetic acid, to furnish the final Compounds 2-7, as seen in Scheme 2 below, with excellent purity and isolated yields.

Scheme 2

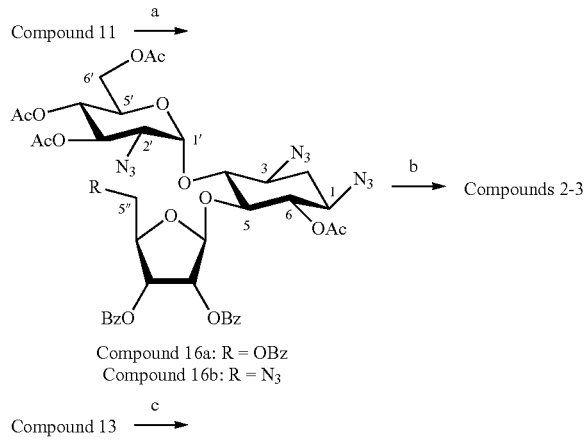

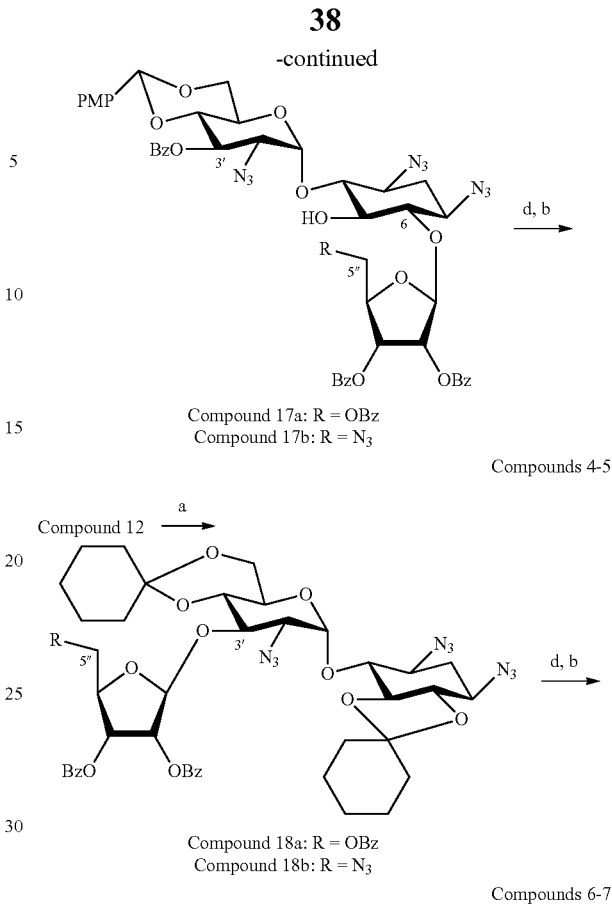

The reagents and conditions seen in Scheme 2 above include: (a) Compound 15a or Compound 15b, BF$_3$-Et$_2$O (catalytic amount), CH$_2$Cl$_2$, 4 Å molecular sieves, Compound 11→Compound 16a (85%), Compound 11→Compound 16b (71%), Compound 12→Compound 18a (95%), Compound 12→Compound 18b (93%); (b) (i) MeNH$_2$ (33% solution in EtOH), (ii) PMe$_3$ (1 M in THF), NaOH 0.1 M, THF, room temperature; Compound 16a→Compound 2 (84%), Compound 16b→Compound 3 (91%), Compound 17a→Compound 4 (for 2 steps 75%), Compound 17b→Compound 5 (44%), Compound 18a→Compound 6 (84%), Compound 18b→Compound 7 (75%); (c) Compound 14a or Compound 14b NIS, TfOH (catalytic amount), CH$_2$Cl$_2$, 4 Å molecular sieves, Compound 13→Compound 17a (68%), Compound 13→Compound 17b (76%); (d) AcOH/H$_2$O 6:1, THF 50° C. for Compound 17a, TFA/H$_2$O 3:2, THF, 60° C. for Compound 17b (52%), AcOH/H$_2$O 10:3, 1,4-dioxane, 70° C. for Compound 18a (75%), TFA/H$_2$O 5:1, THF, 50° C. for Compound 18b (82%); and the abbreviations are: PMP=p-methoxyphenyl, NIS=N-iodosuccinimide, Tf=trifluoromethanesulfonyl, CSA=camphor sulfonic acid, DMF=dimethylformamide, Bz=benzoyl, TFA=trifluoroacetic acid.

Scheme 3 below illustrates the preparation of Compounds 8-9. Ring I in Compound 8 having D-allo configuration was prepared from Compound 1 by selectively inverting the configuration at the C3' position. Triflation of the hydroxyl group at the C3' position in Compound 12 was followed by nucleophilic displacement with azide to afford the corresponding cis-diazide Compound 19 at a yield of 82% for the two steps. Hydrolysis of the cyclohexylidene ketals with aqueous acetic acid, followed by a two-step deprotection as described above provided the designed Compound 8 at 68% yield. Treatment of the same acceptor Compound 12 with CH$_2$Br$_2$ in the presence of NaH gave the protected dimmer Compound 20 at a yield of 82%, which after the similar three-step deprotection as in the case of Compound 19 afforded the desired dimmer Compound 9 at 86% yield.

tamicin C2. In attempts to further modify "Ring II" in Compounds 21 and 23 for structure-activity studies, intermediate Compounds 22 and 24, which combine the functional groups of either G-418 and amikacin (corresponding to Compound 22) or gentamicin and amikacin (corresponding to Compound 24) in one molecule.

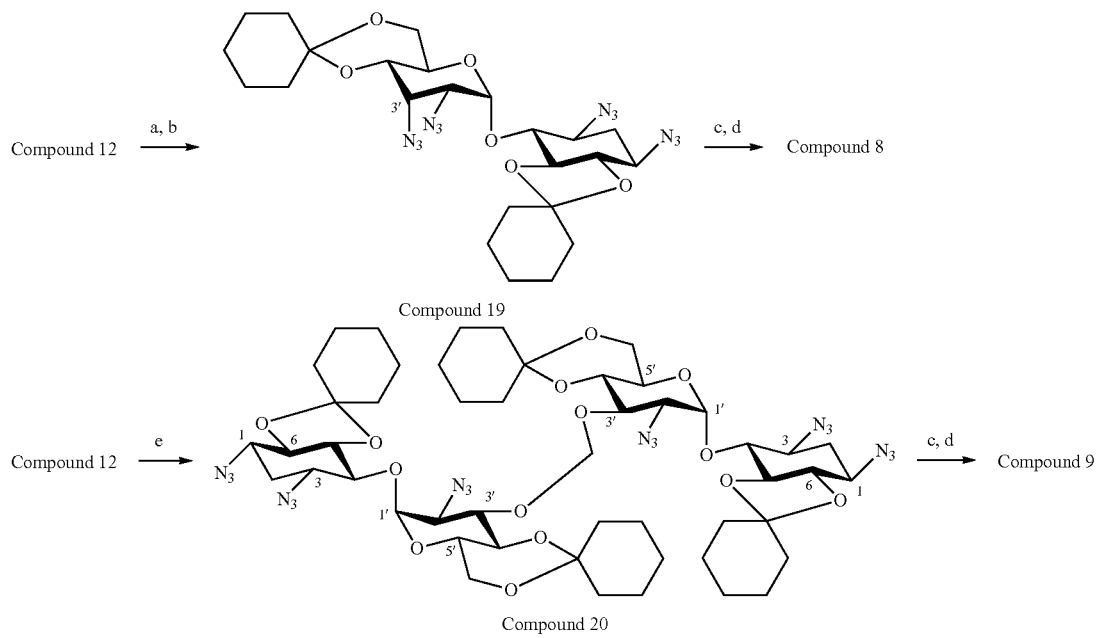

Scheme 3

The reagents and conditions seen in Scheme 2 above include: (a) Tf$_2$O, pyridine, (92%); (b) NaN$_3$, DMF, HMPA, (72%) (c) for Compound 19 AcOH/H$_2$O 8:1, 1,4-dioxane, 75° C., (60%), for Compound 20 TFA/H$_2$O 5:6, THF, 60° C., (90%); (d) (i) MeNH$_2$ (33% solution in EtOH), (ii) PMe$_3$ (1 M in THF), NaOH 0.1 M, THF, room temperature; Compound 19→Compound 8 (76%), Compound 20→Compound 9 (81%), (e) CH$_2$Br$_2$, NaH, DMF/HMPA 2:1, 4 Å molecular sieves, (82%), and the abbreviations are: HMPA=hexamethylphosphoramide.

Being based on Compound 10, intermediate Compound 10-AHB (see, Scheme 4 below) has the paromamine core but in addition it contains (S)-4-amino-2-hydroxybutyryl (AHB) substitution at the N1 position. The N1-AHB substitution is expected to further improve both the read-through activity and toxicity. This expectation is supported by the recent observation that amikacin functions better than gentamicin for restoration of the CFTR protein [79]. Kanamycin A, which differs from amikacin by only the absence of AHB substitution at N-1 position, does not show any read-through activity [6].

Intermediate Compounds 21 and 23 (see, Scheme 4 below) correspond to G-418 and gentamicin respectively. Compounds 21 and 23 are used to prepare C6'-diastereomeric-mixed and separated C6'-diastereomers so as to achieve better nephrotoxicity and cytotoxicity. While this stereochemical issue was tested on the gentamicin C2 [68], no C6'-diastereomer of G-418 appears in the literature. 3'-OH and 4'—OH groups are added to Compound 23 in an attempt to further reduce the toxicity as observed for gen-

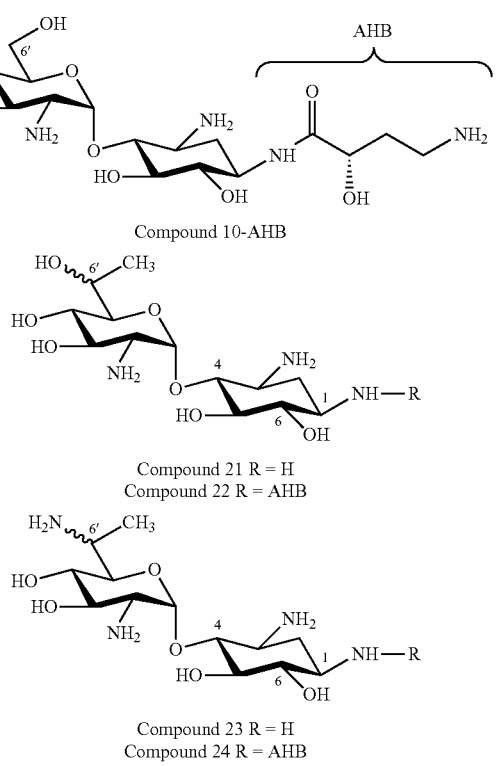

Scheme 4

The preparation of all five Compounds 10-AHB, 21, 22, 23 and 24 starts with paromamine (Compound 1) as a common starting material, readily accessible from paromomycin [80]: selective protection of Compound 1 at N2' and N3 with Cbz is followed by treatment with activated ester of AHB (NOS-AHB-Cbz) according to published procedures [81-84], so as to afford the corresponding N1-AHB derivative of Compound 1, and treatment of this intermediate with Pd/H$_2$ affords Compound 10-AHB.

Similar steps for the introduction of AHB to paromamine 1 followed by selective acetylation gives C5-acceptor Compound 25, and Coupling of Compound 25 with the trichloroacetamidate donor of 5-azidoribose [80] followed by deprotection steps, afford the designed pseudo-trisaccharide Compound 37 (also referred to herein interchangeably as NB54), as illustrates Scheme 5 below. Similar steps for the introduction of AHB to G-418 produce the intermediate Compound 26 which, after subsequent deprotection steps, afford its N1-AHB analog Compound 27 (see, Scheme 5).

The reagents and conditions seen in Scheme 5 above include: (a) (i) Cu(OAc)$_2$, Ni(OAc)$_2$, Cbz-NOS; (ii) NOS-AHB-Cbz, DCC, HOBT; (iii) 4.2 equiv. Ac$_2$O, Py, −7° C.; (b) (i) BF$_3$-OEt$_2$, DCM/MeCN; (ii) MeNH$_2$ (33% sol in EtOH); (iii) Pd/C, H$_2$, dioxane, AcOH; (c) (i) Zn(OAc)$_2$, Cbz-NOS; (ii) NOS-AHB-Cbz, DCC, HOBT; and (d) Pd/C, H$_2$, dioxane, AcOH.

For the preparation of Compound 21, paromamine is subjected to a sequence of seven steps to afford Compound 28 as a mixture of C6'-diastereomers, as illustrated in Scheme 6 below. To determine the absolute stereochemistry of these diastereomers, each is treated with benzaldehyde dimethyl acetal to afford the corresponding benzylidene acetals, Compound 29 with either an equatorial or an axial C6'-methyl group. The NOE spectra of these methyl groups with the C5'-proton along with the coupling constant of the C6'-proton in each diastereomer allow the determination of the absolute configuration at C6'-center. Similarly, the absolute configuration at C6' of the gentamicin derivative Com- Scheme 5

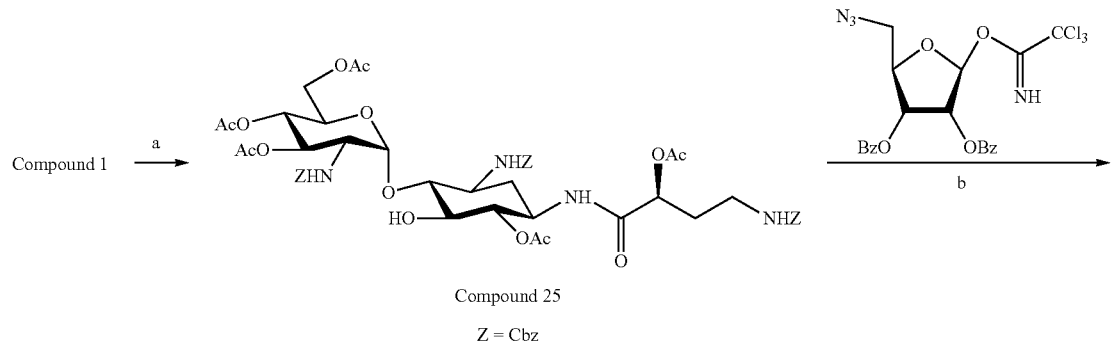

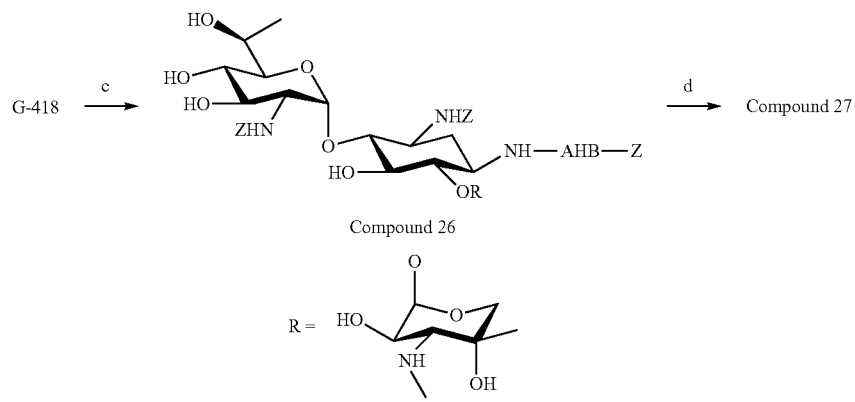

pound 23 is determined. To this effect, Compound 28 is first converted to the corresponding amine Compound 30, which, after protection with Troc and treatment with NaH, affords the corresponding cyclic oxazolidinone Compound 31. Each diastereomer of Compound 28 and Compound 30 is thereafter subjected to Staudinger reaction followed by a similar set of reactions as is shown in Scheme 5 hereinabove, to afford the corresponding N1-AHB derivatives Compound 22 and Compound 24.

Using similar synthetic routes, three series of compounds, presented in Scheme 7 and Scheme 8 below, are prepared using corresponding acceptor compounds for each series of Compounds, namely the intermediate Compound 32 (Scheme 7) for the first series, intermediate Compound 33 for the second series and intermediate Compound 34 for the third series (Scheme 8) and three different donor Compounds 14b, 35 and 36. Donor Compounds 35 and 36 are especially designed with ether protections at C2-OH position (p-methoxy benzyl in Compound 35 and benzyl in Compound 36) in order to allow the desired 1,2-cis glycosidic linkage formation.

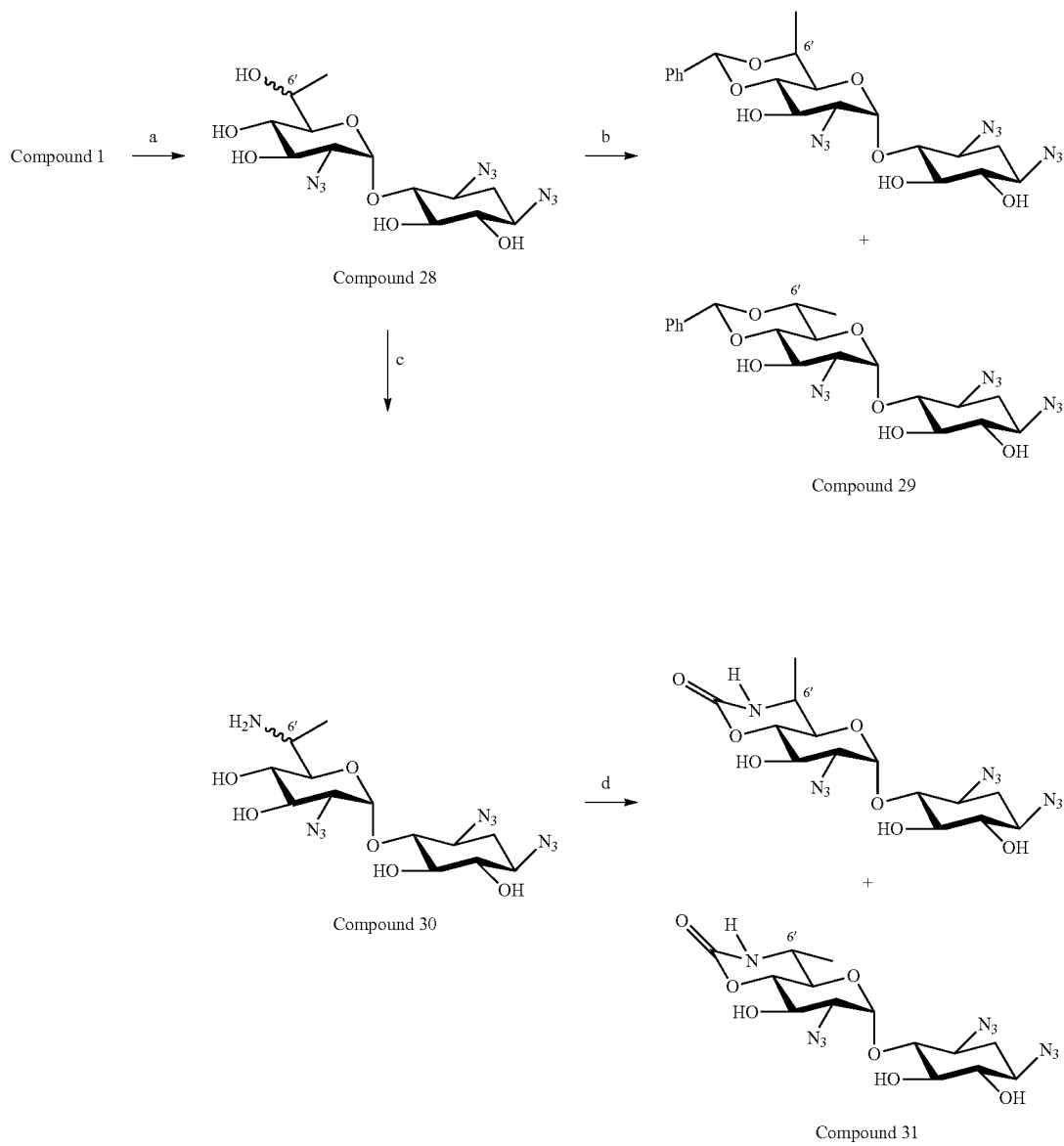

Scheme 6

The reagents and conditions seen in Scheme 6 above include: (a) (i) TfN$_3$, Cu(II); (ii) TIPSCl, Py; (iii) PMBCl, NaH, DMF; (iv) HF/Py; (v) Swern oxydation; (vi) MeMgBr, Et$_2$O; (vii) TFA; (b) Ph(OMe)$_2$, CSA; (c) (i) cyclohexanone dimethyl ketal, CSA; (ii) Swern oxydation; (iii) NH$_3$, NaBCNH$_3$, MeOH; (iv) AcOH, MeOH/H$_2$O; and (d) (i) TrocCl, DCM, Et$_3$N; (ii) NaH, DMF.

Scheme 7

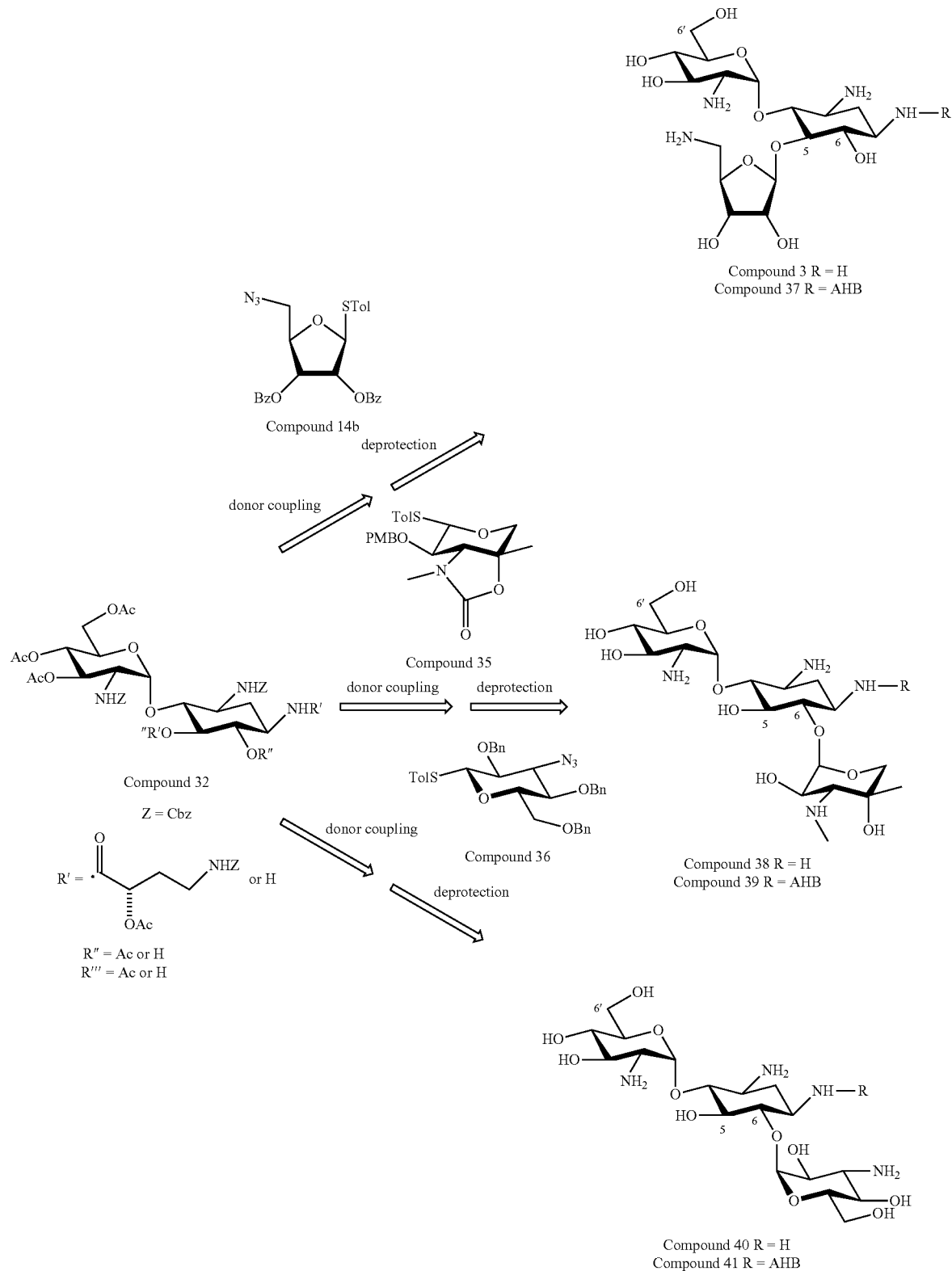

Donor Compound 35 was obtained in a good isolated yield from gentamicin in the following steps: MeOH, AcCl, reflux (90% yield); TrocCl, NaHCO$_3$, CHCl$_3$/H$_2$O (93% yield); BzCl, Py (70% yield); TolSH, BF$_3$-Et$_2$O (53% yield); MeNH$_2$ in EtOH (90% yield); NaH, PMBCl, TBAI (82% yield). The oxazolidinone protection in Compound 35 proved to be very efficient under standard glycosylation reactions. This oxazolidinone ring undergoes spontaneous opening under basic (NaOH) Staudinger condition with heating. Thus, as it generally illustrated in Scheme 7 above, coupling of the acceptor 32 with either of the donors, 14b, 35 or 36 followed by the deprotection steps afforded the desired Compounds 3, 37-41.

Donor Compound 35 was obtained in a good isolated yield from gentamicin in the following steps: MeOH, AcCl, reflux (90% yield); TrocCl, NaHCO$_3$, CHCl$_3$/H$_2$O (93% yield); BzCl, Py (70% yield); TolSH, BF$_3$-Et$_2$O (53% yield); MeNH$_2$ in EtOH (90% yield); NaH, PMBCl, TBAI (82% yield). The oxazolidinone protection in Compound 35 proved to be very efficient under standard glycosylation reactions. This oxazolidinone ring undergoes spontaneous opening under basic (NaOH) Staudinger condition with heating. Thus, as illustrated in Scheme 7 above, coupling of the acceptor Compound 32 with either of the donors, i.e., Compounds 14b, 35 or 36 followed by deprotection steps affords the desired Compounds 3, 37-41.

Similarly, coupling of these donors, Compounds 14b, 35 and 36, with appropriate acceptors, i.e., Compounds 33 or 34 (NIS, AgOTf, Et$_2$O/CH$_2$Cl$_2$) provides the corresponding protected compounds which after standard deprotection steps affords the desired C5- and C6-linked derivatives of Compounds 42-53 as illustrated in Scheme 8 below.

Scheme 8

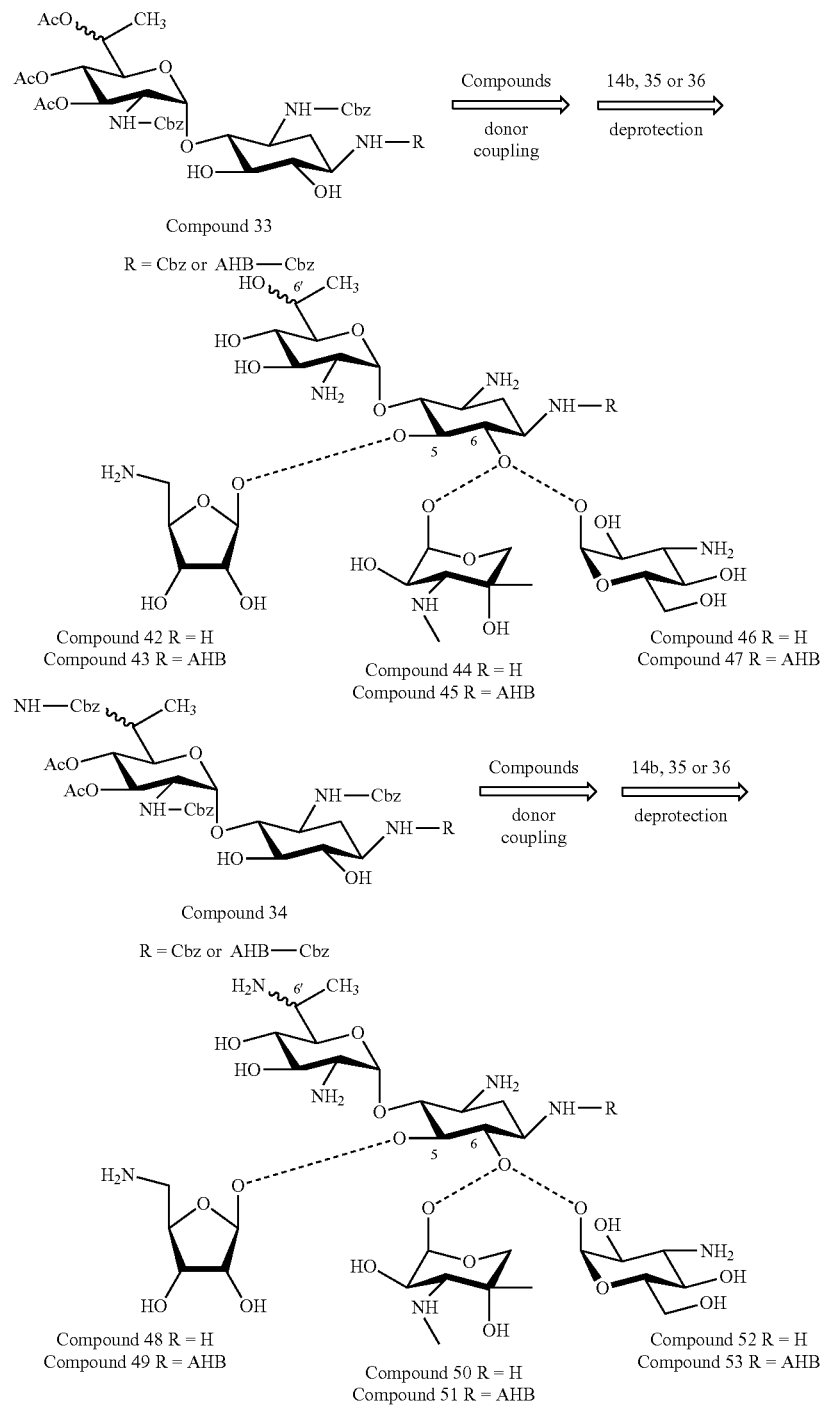

The following examples present detailed synthetic procedures for preparing compounds leading to Compounds 2-9, as outlined in Schemes 1-3 above.

Preparation of Paromamine (Compound 1):

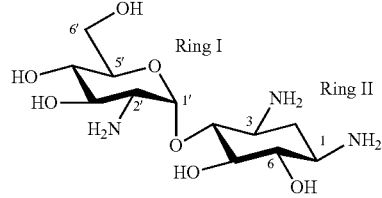

Compound 1

Compound 1 was prepared by direct Lewis acid promoted cleavage of paromomycin according to the published procedure of Ding and co-workers [78] with some modifications.

Acetyl chloride (35 ml) was added to a stirred solution of anhydrous methanol (215 ml) over 10 minutes at 0° C. After stirring for about 15 additional minutes, a commercially available paromomycin sulfate sample (25 grams, 31.0 mmol) was added and the reaction was heated to 70° C. under reflux. Propagation of the reaction was monitored by TLC, using a mixture of $CH_2Cl_2$/MeOH/$H_2O$/Me$NH_2$ at a relative ratio of 10:15:6:15 diluted to 33% solution in ethanol as eluent, which indicated completion after 4 hours. The reaction mixture was cooled for about 2 hours in a freezer, filtered, and the residue was dissolved in a minimal amount of water. This concentrated aqueous solution was added dropwise to cold ethanol (500 ml, 0° C.) and the resulting emulsion was placed in a freezer for about 2 hours. The mixture was filtered and the residue was dried under vacuum to yield Compound 1 as a white solid (12.5 grams, 94% yield).

$^1$H NMR (500 MHz, $D_2O$, pH=3.5) data of Compound 1 are summarized in the Table 1 below.

TABLE 1

| Ring | H1 | H2 | H3 | H4 | H5 | H5' | H6 | H6' |
|---|---|---|---|---|---|---|---|---|
| I | 5.54 d J = 4.0 | 3.28 dd J = 4.0, 11.0 | 3.80 t J = 10.0 | 3.70-3.74 m | 3.35 t J = 9.0 | | 3.78-3.82 m | 3.62 dd J = 4.0, 12.0 |
| | H1 | H2eq | H2ax | | H3 | H4 | H5 | H6 |
| II | 3.16-3.22 m | 2.51 dt J = 4.5, 12.5 | 1.72 ddd $J_1 = J_2 = J_3$ = 12.5 | | 3.33-3.39 m | 3.47 t J = 9.5 | 3.54 t J = 9.0 | 3.72 t J = 9.5 |

$^{13}$C (NMR 125 MHz, $D_2O$): δ=□□30.6 (C-2), 50.6, 51.6, 55.9, 62.1 (C-6'), 71.0, 71.2, 74.3, 75.2, 76.6, 82.7, 98.8 (C-1');

MALDI TOFMS calculated for $C_{12}H_{25}N_3O_7Na$ ([M+Na]$^+$) m/e: 347.2; measured m/e: 347.2.

Preparation of Compound 10:

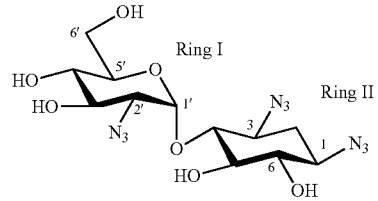

Compound 10

Compound 10 was prepared from Compound 1 (paromamine) according to a published procedure [85] which effected simultaneous conversion of all the amine groups of Compound 1 into corresponding azide groups by treatment with Tf$N_3$ to afford Compound 10 at a 90% yield.

Preparation of Compound 11:

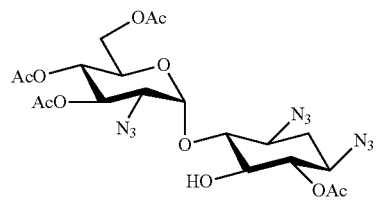

Compound 11

Compound 11 was prepared from the perazido derivative, Compound 10, by regioselective acetylation with acetic anhydride at low temperature according to the published procedure of Swayze and co-workers [78] with the following modifications.

Compound 10 (2 grams, 5 mmol), prepared according to a published procedure [85], was dissolved in dry pyridine (5 ml) and the resulted mixture was cooled down to –6° C. and acetic anhydride (4.2 equivalents, 2.65 ml) was thereafter added thereto. Propagation of the reaction was monitored by TLC (EtOAc/Hexane, 2:3), which indicated completion after 8 hours. The reaction was diluted with EtOAc and extracted with HCl (2%), saturated aqueous NaHCO$_3$, and brine. The combined organic layer was dried over MgSO$_4$ and concentrated under reduced pressure. The crude product was purified by flash chromatography (silica gel, EtOAc/Hexane) to yield Compound 11 (1.84 grams, 65% yield).

MALDI TOFMS calculated for $C_{20}H_{27}N_9O_{11}Na$ ([M+Na]$^+$) m/e: 592.2; measured m/e: 592.2.

Preparation of Compound 12:

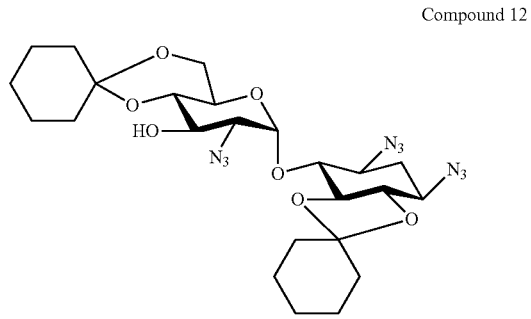

Compound 12

Cyclohexanone dimethyl ketal (30 ml, 200 mmol) and a catalytic amount of camphor sulfonic acid (CSA) were added to a solution of Compound 10 (8.9 grams, 22.2 mmol) in dry DMF (30 ml). The reaction was stirred for 1 hour at 50° C. and propagation was monitored by TLC (100% EtOAc), which indicated complete consumption of the starting material. Thereafter the reaction was heated to 110° C. in an oil bath and the propagation of the reaction was monitored by TLC (EtOAc/Hexane, 2:3), which indicated the completion of the reaction after 4 hours. The reaction mixture was diluted with EtOAc and extracted with saturated aqueous NaHCO$_3$, brine, dried over MgSO$_4$ and concentrated under reduced pressure. The crude product was purified by flash chromatography to yield Compound 12 (8.5 grams, 67% yield).

$^1$H NMR (500 MHz, CDCl$_3$): δ=1.25-1.95 (m, 20H, cyclohexanones), 1.47 (ddd, 1H, $J_1=J_2=J_3=12.5$ Hz, H-2 axial), 2.33 (dt, 1H, $J_1=5$, $J_2=14.5$H-2 equatorial), 3.26 (dd, 1H, $J_1=3.5$ $J_2=13.5$ Hz, H-2'), 3.39 (t, J=9.5 Hz, 1H, H-4), 3.47-3.55 (m, 2H, H-3, H-5), 3.55 (t, J=9.5 Hz, 1H, H-5'), 3.62-3.68 (m, 1H, H-1), 3.75-3.82 (m, 1H, H-6'), 3.80 (t, J=9.0 Hz 1H, H-6), 3.85-3.92 (m, 2H, H-4', H-6'), 4.07 (t, 1H, J=9.5 Hz, H-3'), 5.50 (d, 1H, J=4.0 Hz, H-1').

$^{13}$C NMR (125 MHz, CDCl$_3$): δ=(the range 22.4-37.8 relates to cyclohexanone carbon atoms if not indicated otherwise) 22.5, 22.8, 23.7 (2C), 24.9, 25.5, 27.8, 33.9, 36.0, 36.3, 37.8, 57.2, 60.4, 61.5 (C-6'), 61.9, 64.0, 68.7, 73.7, 76.8, 79.3, 79.4, 97.0 (C-1'), 99.1(OCO cyclohexanone ketal), 113.7 (OCO cyclohexanone ketal).

ESIMS calculated for $C_{24}H_{35}N_9O_7Na$ ([M+Na]$^+$) m/e: 584.3; measured m/e: 584.3.

Preparation of Compound 13e:

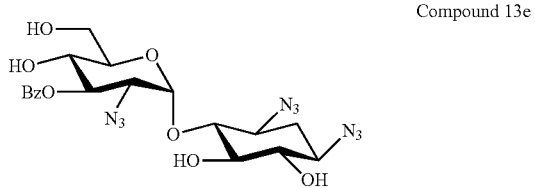

Compound 13e

Compound 12 (2.5 grams, 4.45 mmol) was dissolved in dry pyridine (20 ml) followed by the addition of 4-dimethylamonpyridine (0.5 gram, 4.6 mmol). The reaction mixture was stirred for 5 minutes at room temperature, and thereafter benzoylchloride (1.3 ml, 0.9 mmol) was added. Propagation of the reaction was monitored by TLC (EtOAc/Hexane, 1:4), which indicated completion after about 8 hours. The reaction mixture was diluted with EtOAc, extracted with HCl (2%), H$_2$O and brine, dried over MgSO$_4$ and concentrated under reduced pressure.

The crude residue was dissolved in THF (20 ml) added with TFA (5 ml) and water (3 ml). The reaction mixture was stirred at 40° C. for 8 hours during which the propagation of the reaction was monitored by TLC (EtOAc/Hexane, 7:3). The reaction mixture was purified directly by flash chromatography (silica, EtOAc/Hexane) without any further work up to yield Compound 13e (2 grams, 89% overall yield).

$^1$H NMR (500 MHz, CDCl$_3$): δ=☐☐1.49-1.53 (m, 1H, H-2 axial), 2.32-2.35 (m, 1H, H-2 equatorial), 3.34-3.44 (m, 4H, H-1, H-3, H-4 and H-5), 3.55-3.57 (m, 1H, H-6), 3.74-3.77 (m, 1H, H-2'), 3.86-3.93 (m, 3H, H-5' and 2H-6'), 4.10-4.14 (m, 1H, H-4'), 5.49 (d, 1H, J=3 Hz, H-1') 5.59 (t, 1H, J=10 Hz, H-3'), 7.48 (t, 2H, J=7.5 Hz), 7.62 (t, 1H, J=7 Hz), 8.08 (d, 2H, J=7.5 Hz).

$^{13}$C NMR (125 MHz, CDCl$_3$): δ=32.0 (C-2), 58.8, 59.6, 61.7 (C-6'), 62.3, 69.6, 72.6, 75.1, 75.5, 75.9, 83.2, 99.0 (C-1'), 128.6 (2C), 130.0 (2C), 133.9, 167.3.

MALDI TOFMS calculated for $C_{19}H_{23}N_9O_8Na$ ([M+Na]$^+$) m/e: 528.2; measured m/e: 528.2.

Preparation of Compound 13:

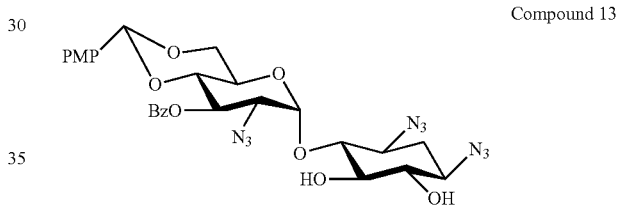

Compound 13

1-(Dimethoxymethyl)-4-methoxybenzene (1.3 ml, 7.6 mmol) and a catalytic amount of CSA were added to a solution of Compound 13e (1.93 grams, 3.82 mmol) dissolved in dry DMF (10 ml). The reaction mixture was stirred at 50° C. and propagation was monitored by TLC (EtOAc/Hexane, 1:1), which indicated the completion after 8 hours. The reaction was diluted with EtOAc and extracted with saturated NaHCO$_3$, brine, dried over MgSO$_4$ and concentrated under reduced pressure. The crude product was purified by flash chromatography to yield Compound 13 (2 grams, 84% yield).

$^1$H NMR (500 MHz, CDCl$_3$): δ=1.47-1.53 (m, 1H, H-2 axial), 2.32-2.35 (m, 1H, H-2 equatorial), 3.33-3.45 (m, 4H, H-1, H-3, H-4 and H-5), 3.58-3.61 (m, 1H, H-6), 3.74-3.77 (m, 1H, H-2'), 3.75-3.81 (m, 2H, H-5' and H-6'), 3.76 (s, 3H, OCH$_3$), 4.30-4.35 (m, 2H, H-4' and H-6'), 5.36 (d, 1H, J=3.5 Hz, H-1'), 5.48 (s, 1H), 5.88 (t, 1H, J=10 Hz, H-3'), 6.83 (d, 2H, J=8.5 Hz), 7.33 (d, 2H, J=9 Hz), 7.46 (t, 2H, J=7.5 Hz), 7.59 (t, 1H, J=7.5 Hz), 8.07 (d, 2H, J=7.5 Hz).

$^{13}$C NMR (125 MHz, CDCl$_3$): δ=31.9 (C-2), 55.2, 58.5, 59.7, 62.9 (C-5'), 63.6 (C-4'), 68.6 (C-6'), 70.5 (C-3'), 75.5, 75.8, 79.2, 83.2, 99.9 (C-1'), 101.5, 127.4 (4C), 128.4 (2C), 129.2 (2C), 129.9 (2C), 133.4, 160.0, 165.5.

MALDI TOFMS calculated for $C_{27}H_{29}N_9O_9Na$ ([M+Na]$^+$) m/e: 623.2; measured m/e: 623.2.

Preparation of p-Methylphenyl-2,3,5-tri-O-benzoyl-1-thio-D-ribofuranose (Compound 14a)

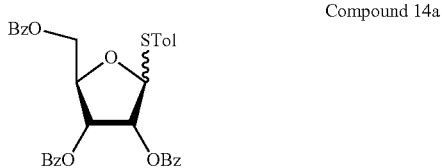

Compound 14a

4-Methylbenzenethiol (0.6 grams, 4.83 mmol) and BF$_3$-Et$_2$O (1.5 ml) were added to a solution of 1-O-Acetyl-2,3,5-tri-O-benzoyl-β-D-ribofuranose (2.0 grams, 3.96 mmol) dissolved in CH$_2$Cl$_2$ (25 ml). The resulting mixture was stirred at room temperature under argon. Propagation of the reaction was monitored by TLC (EtOAc/Hexane, 1:4), which indicated completion after 8 hours. The reaction mixture was diluted with EtOAc (200 ml), neutralized with saturated NaHCO$_3$, and washed with brine. The combined organic layer was dried over MgSO$_4$ and evaporated under reduced pressure. The residue was purified by flash chromatography (silica gel, EtOAc/Hexane) to yield Compound 14a (2.0 grams, 89% yield) as a mixture of anomers (α/β 3:5).

Spectral analysis of the α-anomer:
$^1$H NMR (500 MHz, CDCl$_3$)□: δ=2.23 (s, 3H, Me-STol), 4.50 (dd, 1H, J$_1$=3.5, J$_2$=9.0 Hz, H-5'), 4.64 (m, 2H, H-4 and H-5), 5.56 (d, 1H, J=5.0 Hz, H-1), 5.66 (t, 1H, J=5.0 Hz, H-2), 5.73 (t, 1H, J=5.0 Hz, H-3), 7.06-8.11 (19H);
$^{13}$C NMR (125 MHz, CDCl$_3$): δ=21.1 (Me-STol), 64.3 (C-5), 72.4 (C-3), 74.3 C-2), 80.4 (C-4), 88.0 (C-1), 128.4-166.2 (27C).

Spectral analysis of the β-anomer:
$^1$H NMR (500 MHz, CDCl$_3$): δ=2.33 (s, 3H, Me-STol), 4.63 (dd, 1H, J$_1$=3.5, J$_2$=14.0 Hz, H-5), 4.74 (dd, 1H, J$_1$=3.0 J$_2$=12.0 Hz, H-5'), 4.88 (dd, 1H, J$_1$=4.5, J$_2$=8.0 Hz, H-4), 5.80-5.83 (m, 2H, H-2, H-3), 6.05 (d, 1H, J=5.0 Hz, H-1), 7.06-8.11 (19H);
$^{13}$C NMR (125 MHz, CDCl$_3$): δ=21.1 (Me-STol), 63.8 (C-5), 71.6 (C-3), 72.2 (C-2), 79.0 (C-4), 90.8 (C-1), 128.4-166.2 (27C).

MALDI TOFMS calculated for C$_{33}$H$_{28}$O$_7$S Na ([M+Na]$^+$) m/e: 591.2; measured m/e: 591.3.

Preparation of 5-deoxy-5-azido-2,3-di-O-benzoyl-1-O-tricloroacetymido-D-ribofuranose (Compound 15b)

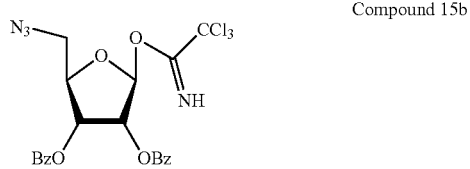

Compound 15b

N-Bromosuccinimide (NBS, 0.8 grams, 4.41 mmol) was added to a solution of Compound 14b (1.8 grams, 3.67 mmol), prepared according to a published procedure [86], in acetone (30 ml) cooled to −10° C., and the propagation of the reaction was monitored by TLC (EtOAc/Hexane, 3:7), which indicated completion after 2 hours. The reaction mixture was diluted with EtOAc (200 ml) and washed with NH$_4$Cl and brine. The combined organic layer was dried over MgSO$_4$ and evaporated under reduced pressure. The residue was purified by flash chromatography (silica gel, EtOAc/Hexane) to afford the desired anomeric alcohol.

The intermediate alcohol was dissolved in dry CH$_2$Cl$_2$ (10 ml) and CCl$_3$CN (1.7 ml, 11.8 mmol) and K$_2$CO$_3$ (200 mg, 1.4 mmol) were added thereto. The mixture was stirred at room temperature and the propagation of the reaction was monitored by TLC (EtOAc/Hexane, 3:7), which indicated completion after 8 hours. The reaction mixture was diluted with CH$_2$Cl$_2$, and filtered through celite. The celite was washed thoroughly with CH$_2$Cl$_2$, and evaporated to dryness to yield Compound 15b (1.89 grams, 97% overall yield) as a mixture of anomers (α/β 1:9).

Spectral analysis of the α-anomer:
$^1$H NMR (500 MHz, CDCl$_3$): δ=3.63 (dd, 1H, J$_1$=5.0, J$_2$=13.5 Hz, H-5), 3.73 (dd, 1H, 1H, J$_1$=3.5, J$_2$=13.5 Hz, H-5'), 4.64-4.68 (m, 1H, H-4), 5.76 (dd, 1H, J$_1$=5.0, J$_2$=6.5 Hz, H-3), 5.94 (d, 1H, J=5.0 Hz, H-2), 6.57 (s, 1H, H-1), 7.31-8.15 (10H), 8.72 (s, 1H);
$^{13}$C NMR (125 MHz, CDCl$_3$): δ=52.9 (C-5), 71.9 (C-3), 74.8 C-2), 81.9 (C-4), 102.6 (C-1), 128.4-133.6 (10C), 160.4, 165.0, 165.4.

ESIMS calculated for C$_{19}$H$_{17}$N$_3$O$_6$Na ([M-C$_2$NCl$_3$+Na]$^+$) m/e: 406.1; measured m/e: 406.1.

Preparation of Compound 16a:

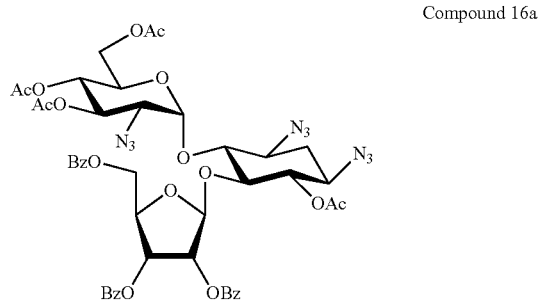

Compound 16a

Anhydrous CH$_2$Cl$_2$ (5 ml) was added to powdered, flame-dried 4 Å molecular sieves (500 mg), followed by the addition of the acceptor Compound 11 (300 mg, 0.527 mmol), prepared as presented hereinabove, and the donor Compound 15a (1.15 grams, 1.896 mmol), prepared according to a published procedure [86]. The reaction mixture was stirred for 10 minutes at room temperature, and then cooled to −40° C. Thereafter a catalytic amount of BF$_3$-Et$_2$O (10 μl) was added to the reaction mixture and stirring continues at −15° C. Propagation of the reaction was monitored by TLC (EtOAc/Hexane, 3:7), which indicated completion after 1.5 hours. The reaction mixture was diluted with CH$_2$Cl$_2$, and filtered through celite. After thorough washing of the celite with CH$_2$Cl$_2$, the washes were combined and extracted with saturated aqueous NaHCO$_3$, brine, dried over MgSO$_4$ and concentrated. The crude product was purified by flash chromatography to yield Compound 16a (452 mg, yield of 85%).

$^1$H NMR (500 MHz, CDCl$_3$) data of Compound 16a are summarized in Table 2 below.

TABLE 2

| Ring | H1 | H2 | H3 | H4 | H5 | H5' | H6 | H6' |
|---|---|---|---|---|---|---|---|---|
| I | 5.69 d J = 4.0 | 3.44 dd J = 4.0, 10.5 | 5.33 t J = 9.5, 10.5 | 5.01 t J = 10.0 | 4.42-4.45 m | | 4.12 dd J = 4.5, 12.0 | 4.20 dd J = 4.5, 12.5 |
| III | 5.56 S | 5.63 d J = 4.5 | 5.71-5.74 m | 4.67-4.70 m | 4.36 dd J = 3.5, 12.0 | 5.04 dd J = 3.0, 12.0 | | |

| | H1 | H2eq | H2ax | H3 | H4 | H5 | H6 |
|---|---|---|---|---|---|---|---|
| II | 3.32-3.39 m | 2.31 dt $J = 5.0, 13.0$ | 1.37 ddd $J_1 = J_2 = 12.0$ $J_3 = 13.0$ | 3.32-3.39 m | 3.16 t J = 9.0 | 3.74 t J = 10.0 | 4.74 t J = 10.0 |

Additional $^1$H NMR (500 MHz, CDCl$_3$) data for Compound 16a included: δ=2.03 (s, 3H, Ac), 2.06 (s, 3H, Ac), 2.12 (s, 3H, Ac), 2.33 (s, 3H, Ac), 7.35 (t, 2H, J=8, 7.5 Hz, Bz), 7.41 (t, 2H, J=7.5, 8 Hz, Bz), 7.49-7.62 (m, 5H, Bz), 7.89 (d, 2H, J=7.5, Bz), 7.95 (d, 2H, J=7, Bz), 8.14 (d, 2H, J=7, Bz).

$^{13}$C NMR (125 MHz, CDCl$_3$): δ=20.6, 20.7, 20.8, 21.0, 31.4 (C-2), 58.2, 58.4, 61.8, 62.0 (C-6'), 62.6 (C-5"), 67.9, 68.2, 70.8, 71.2, 73.8, 74.7, 77.9, 79.5, 80.4, 96.4 (C-1'), 107.6 (C-1"), 128.4 (2C), 128.6 (3C), 128.7, 128.9, 129.7 (3C), 129.8 (3C), 130.3 (2C), 133.3, 133.5, 133.7, 165.2, 165.4, 166.2, 169.7, 170.1 (2C), 170.7.

MALDI TOFMS calculated for $C_{46}H_{47}N_9O_{18}K$ ([M+K]$^+$) m/e: 1052.3; measured m/e: 1052.4.

Preparation of Compound 16b:

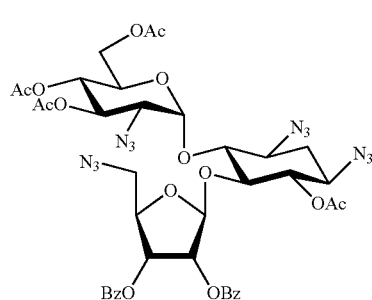

Compound 16b

Anhydrous CH$_2$Cl$_2$ (5 ml) was added to powdered, flame-dried 4 Å molecular sieves (500 mg), followed by the addition of the acceptor Compound 11 (300 mg, 0.527 mmol) and the donor Compound 15b (1 gram, 1.896 mmol), both of which were prepared as presented hereinabove. The reaction mixture was stirred for 10 minutes at room temperature, and then cooled to −40° C. Thereafter a catalytic amount of BF$_3$-Et$_2$O (10 μl) was added to the reaction mixture and stirring continued at −15° C. Propagation of the reaction was monitored by TLC (EtOAc/Hexane, 3:7), which indicated completion after 1.5 hours. The reaction mixture was diluted with CH$_2$Cl$_2$, and filtered through celite. After thorough washing of the celite with CH$_2$Cl$_2$, the washes were combined and extracted with saturated aqueous NaHCO$_3$, brine, dried over MgSO$_4$ and concentrated. The crude product was purified by flash chromatography to yield Compound 16b (350 mg, yield of 71%).

$^1$H NMR (500 MHz, CDCl$_3$) data of Compound 16b are summarized in Table 3 below.

TABLE 3

| Ring | H1 | H2 | H3 | H4 | H5 | H5' | H6 | H6' |
|---|---|---|---|---|---|---|---|---|
| I | 5.84 d J = 4.0 | 3.56-3.59 m | 5.41 t J = 9.5 | 5.07 t J = 9.5 | 4.52-4.55 m | | 4.15-4.18 m | 4.25-4.29 m |
| III | 5.66 s | 5.58 d J = 4.5 | 5.39-5.46 m | 4.49-4.55 m | 3.56-3.61 m | 3.56-3.61 m | | |

| | H1 | H2eq | H2ax | H3 | H4 | H5 | H6 |
|---|---|---|---|---|---|---|---|
| II | 3.49-3.55 m | 2.41 dt $J = 5.0, 12.5$ | 1.61 ddd $J_1 = J_2 = J_3 = 12.5$ | 3.49-3.55 m | 3.73 t J = 9.5 | 3.88 t J = 9.5 | 5.02 t J = 10.0 |

Additional $^1$H NMR (500 MHz, CDCl$_3$) data for Compound 16b included: δ=2.05 (s, 3H, Ac), 2.09 (s, 3H, Ac), 2.10 (s, 3H, Ac), 2.31 (s, 3H, Ac), 7.34-7.39 (m, 2H, Bz), 7.40-7.43 (m, 2H, Bz), 7.52-7.61 (m, 2H, Bz), 7.88 (d, 2H, J=8, Bz), 7.95 (d, 2H, J=8.5, Bz).

$^{13}$C NMR (125 MHz, CDCl$_3$): δ=20.6, 20.7, 20.8, 20.9, 31.7 (C-2), 52.1 (C-5"), 58.3, 58.6, 61.7, 61.8 (C-6'), 68.1, 68.2, 70.8, 71.0, 73.9, 74.6, 77.8, 79.8, 80.8, 96.7 (C-1'), 107.6 (C-1"), 128.5 (3C), 128.6 (2C), 128.8, 129.6 (4C), 133.6, 133.7, 165.2, 165.4, 169.8, 170.0 (2C), 170.7.

MALDI TOFMS calculated for $C_{39}H_{42}N_{12}O_{16}Na$ ([M+Na]$^+$) m/e 957.3; measured m/e 957.5.

Preparation of Compound 17a:

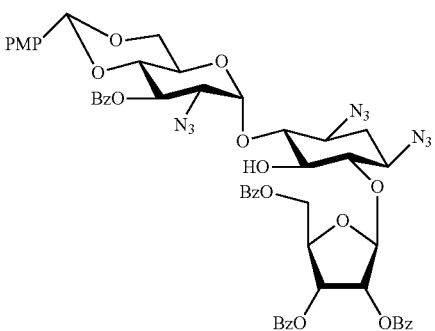

Compound 17a

Anhydrous CH$_2$Cl$_2$ (5 ml) was added to powdered, flame-dried 4 Å molecular sieves (800 mg), followed by the addition of the acceptor Compound 13 (420 mg, 0.674 mmol) and the donor Compound 14a (334 mg, 0.808 mmol), both of which were prepared as presented hereinabove. The reaction mixture was stirred for 10 minutes at room temperature, and then N-iodosuccinimide (NIS, 290 mg, 0.129 mmol) was added to the reaction mixture and stirring continued at room temperature for 5 minutes. Thereafter the reaction mixture was cooled to −40° C. and a catalytic amount of TfOH (10 μl) was added thereto. Propagation of the reaction was monitored by TLC (EtOAc/Hexane, 2:3), which indicated completion after 2 hours. The reaction mixture was diluted with $CH_2Cl_2$, and filtered through celite. After thorough washing of the celite with EtOAc, the washes were combined and extracted with $Na_2S_2O_3$ (10%), saturated aqueous $NaHCO_3$, brine, dried over $MgSO_4$ and concentrated under reduced pressure. The crude product was purified by flash chromatography to yield Compound 17a (490 mg, yield of 68%).

$^1$H NMR (500 MHz, $CDCl_3$) data of Compound 17a are summarized in Table 4 below.

TABLE 4

| Ring | H1 | H2 | H3 | H4 | H5 | H5' | H6 | H6' |
|---|---|---|---|---|---|---|---|---|
| I | 5.42 d<br>J = 4.0 | 3.72-3.75 m | 5.89 t<br>J = 10.0 | 4.31-4.36 m | 3.79 m<br>J = 9.5 | | 3.76-3.79 m | 4.31-4.36 m |
| III | 5.78 s | 5.78 s | 5.84 t<br>J = 5.5 | 4.77-4.80 m | 4.77-4.80 m | 4.69 dd<br>J = 7.0, 12.5 | | |

| | H1 | H2eq | H2ax | H3 | H4 | H5 | H6 |
|---|---|---|---|---|---|---|---|
| II | 3.31-3.43 m | 2.33-2.37 m | 1.46-1.54 m | 3.31-3.43 m | 3.31-3.43 m | 3.71-3.75 m | 3.59 t<br>J = 9.5 |

Additional $^1$H NMR (500 MHz, $CDCl_3$) data for Compound 17a included: δ=5.49 (s, 1H), 7.32-7.61 (m, 14H), 7.89 (d, 2H, J=7.5 Hz), 7.92 (d, 2H, J=7.0 Hz), 7.99 (d, 2H, J=7.0 Hz), 8.07-8.09 (m, 4H).

$^{13}$C NMR (125 MHz, $CDCl_3$): δ=32.0 (C-2), 55.2 ($CH_3$), 58.2, 58.8, 62.7, 63.5, 65.1 (C-6'), 68.6 (C-5"), 70.4, 72.3, 75.7, 76.1, 79.1, 79.3, 80.8, 82.9, 99.8 (C-1'), 101.5, 106.5 (C-1"), 113.5 (2C), 127.4-133.5 (27C), 160.0, 165.3 (2C), 165.6, 166.1.

MALDI TOFMS calculated for $C_{53}H_{49}N_9O_{16}Na$ ([M+Na]$^+$) m/e: 1090.3; measured m/e: 1090.3.

Preparation of Compound 17b:

Compound 17b

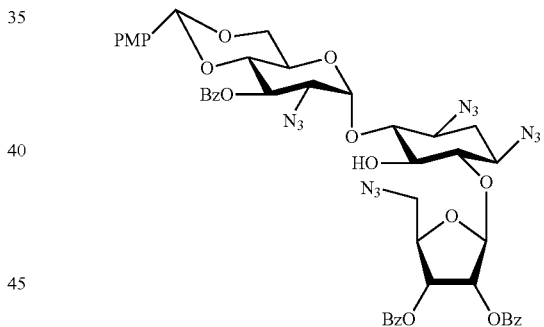

Anhydrous $CH_2Cl_2$ (5 ml) was added to powdered, flame-dried 4 Å molecular sieves (500 mg), followed by the addition of the acceptor Compound 13 (350 mg, 0.561 mmol) and the donor Compound 14b (334 mg, 0.682 mmol), both of which were prepared as presented hereinabove. The reaction mixture was stirred for 10 minutes at room temperature, and then NIS (290 mg, 0.129 mmol) was added to the reaction mixture and stirring continued at room temperature for 5 minutes. Thereafter the reaction mixture was cooled to −40° C. and a catalytic amount of TfOH (10 μl) was added thereto. Propagation of the reaction was monitored by TLC (EtOAc/Hexane, 2:3), which indicated completion after 2 hours. The reaction mixture was diluted with $CH_2Cl_2$, and filtered through celite. After thorough washing of the celite with EtOAc, the washes were combined and extracted with $Na_2S_2O_3$ (10%), saturated aqueous $NaHCO_3$, brine, dried over $MgSO_4$ and concentrated under reduced pressure. The crude product was purified by flash chromatography to yield Compound 17b as a mixture of anomers at a ratio of α/β 1:5 (420 mg, yield of 76%).

$^1$H NMR (500 MHz, $CDCl_3$) data of Compound 17b are summarized in Table 5 below.

TABLE 5

| Ring | H1 | H2 | H3 | H4 | H5 | H5' | H6 | H6' |
|------|-----|-----|-----|-----|-----|------|-----|-----|
| I | 5.39 d<br>J = 3.5 | 3.70-3.73 m | 5.59 t<br>J = 10.0 | 4.10-4.13 m | 3.88 t<br>J = 9.5 | | 3.90-3.92 m | 3.90-3.92 m |
| III | 5.80 s | 5.71 d<br>J = 5.0 | 5.62-5.65 m | 4.54-4.56 m | 3.63-3.65 m | 3.74-3.79 m | | |

| | H1 | H2eq | H2ax | H3 | H4 | H5 | H6 |
|---|-----|------|------|-----|-----|-----|-----|
| II | 3.33-3.40 m | 2.33 2.37 m | 1.49-1.57 m | 3.45-3.50 m | 3.33-3.40 m | 3.74-3.79 m | 3.62 t<br>J = 8.5 |

Additional $^1$H NMR (500 MHz, CDCl$_3$) data for Compound 17b included: δ=5.50 (s, 1H), 7.34 (t, 2H, J=7.5 Hz), 7.39 (t, 2H, J=7.5 Hz), 7.45 (t, 2H, J=7.5 Hz), 7.51-7.61 (m, 3H), 7.89 (d, 2H, J=7.5 Hz), 7.98 (d, 2H, J=7.5 Hz), 8.07 (d, 2H, J=7.5 Hz).

$^{13}$C NMR (125 MHz, CDCl$_3$): δ=31.9 (C-2), 53.1 (C-5"), 55.1, 58.7, 62.7, 63.4, 68.5 (C-6'), 70.4, 72.2, 75.6, 76.1, 79.1 (2C), 83.1, 99.9 (C-1'), 101.4, 105.9 (C-1"), 113.4 (2C), 127.3-133.5 (21C), 159.9, 165.2 (2C), 165.3.

MALDI TOFMS calculated for C$_{46}$H$_{44}$N$_{12}$O$_{14}$Na ([M+Na]$^+$) m/e: 1011.3; measured m/e: 1011.6.

Preparation of Compound 18a:

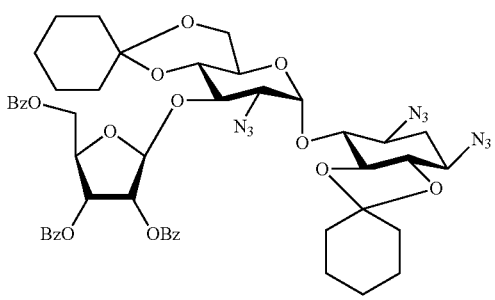

Compound 18a

Anhydrous CH$_2$Cl$_2$ (5 ml) was added to powdered, flame-dried 4 Å molecular sieves (500 mg), followed by the addition of the acceptor Compound 12 (200 mg, 0.356 mmol) and the donor Compound 15a (300 mg, 0.494 mmol), both of which were prepared as presented hereinabove. The reaction mixture was stirred for 10 minutes at room temperature, and then cooled to −40° C. Thereafter a catalytic amount of BF$_3$-Et$_2$O (10 µl) was added to the reaction mixture and stirring continued at −20° C. Propagation of the reaction was monitored by TLC (EtOAc/Hexane, 15:85), which indicated completion after 3 hours. The reaction mixture was diluted with CH$_2$Cl$_2$, and filtered through celite. After thorough washing of the celite with CH$_2$Cl$_2$, the washes were combined and extracted with saturated aqueous NaHCO$_3$, brine, dried over MgSO$_4$ and concentrated. The crude product was purified by flash chromatography to yield Compound 18a (340 mg, yield of 95%).

$^1$H NMR (500 MHz, CDCl$_3$) data of Compound 18a are summarized in Table 6 below.

TABLE 6

| Ring | H1 | H2 | H3 | H4 | H5 | H5' | H6 | H6' |
|------|-----|-----|-----|-----|-----|------|-----|-----|
| I | 5.12 d<br>J = 3.5 | 3.35-3.37 m | 3.91-3.96 m | 3.51-3.54 m | 3.91-3.96 m | | 3.75-3.83 m | 3.75-3.83 m |
| III | 5.55 s | 5.75 d<br>J = 4.5 | 5.87 t<br>J = 5.0 | 4.77-4.81 m | 4.57 dd<br>J = 5.0, 12.5 | 4.93 dd<br>J = 4.0, 12.5 | | |

| | H1 | H2eq | H2ax | H3 | H4 | H5 | H6 |
|---|-----|------|------|-----|-----|-----|-----|
| II | 3.23-3.28 m | 2.30 dt<br>J = 4.0, 13.5 | 1.47 ddd<br>J$_1$ = J$_2$ = J$_3$ = 12.5 | 3.38-3.52 m | 3.23-3.28 m | 3.38-3.52 m | 3.38-3.52 m |

Additional $^1$H NMR (500 MHz, CDCl$_3$) data for Compound 18a included: δ=1.25-1.30 (m, 5H), 1.62-1.89 (m, 15H), 7.34-7.61 (m, 9H, aromatic), 7.92 (d, 2H, J=7.5 Hz), 8.02 (d, 2H, J=7.5 Hz), 8.11 (d, 2H, J=7.5 Hz).

$^{13}$C NMR (125 MHz, CDCl$_3$): δ=24.7 (2C), 26.8 (4C), 31.9 (C-2), 41.8 (4C), 52.6, 58.6, 59.4, 61.9 (C-5"), 62.5, 63.6 (C-6'), 69.2, 71.4, 71.8, 75.1, 75.2, 75.7, 76.0, 81.2, 83.6, 85.0, 98.8 (C-1'), 107.2 (C-1"), 128.3-129.7 (15C), 133.4, 133.5 (2C), 165.0, 165.2, 166.1.

ESIMS calculated for C$_{50}$H$_{55}$N$_9$O$_{14}$Na ([M+Na]$^+$) m/e: 1044.4; measured m/e: 1044.4.

Preparation of Compound 18b:

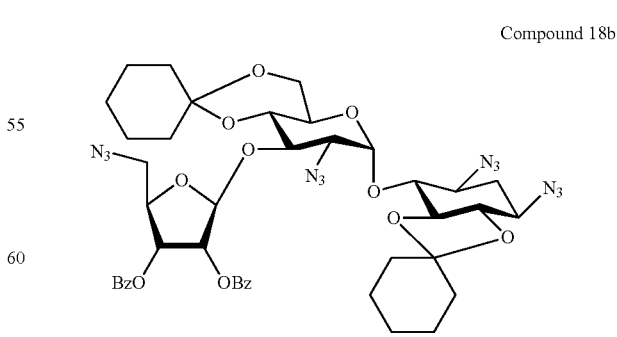

Compound 18b

Anhydrous CH$_2$Cl$_2$ (5 ml) was added to powdered, flame-dried 4 Å molecular sieves (500 mg), followed by the addition of the acceptor Compound 12 (340 mg, 0.605 mmol) and the donor Compound 15b (600 mg, 1.107 mmol), both of which were prepared as presented hereinabove. The reaction mixture was stirred for 10 minutes at room temperature, and then cooled to −20° C. Thereafter a catalytic amount of BF$_3$-Et$_2$O (10 μl) was added to the reaction mixture and stirring continued at −20° C. Propagation of the reaction was monitored by TLC (EtOAc/Hexane, 15:85), which indicated completion after 3 hours. The reaction mixture was diluted with CH$_2$Cl$_2$, and filtered through celite. After thorough washing of the celite with CH$_2$Cl$_2$, the washes were combined and extracted with saturated aqueous NaHCO$_3$, brine, dried over MgSO$_4$ and concentrated. The crude product was purified by flash chromatography to yield Compound 18b (520 mg, yield of 93%).

$^1$H NMR (500 MHz, CDCl$_3$) data of Compound 18b are summarized in Table 7 below.

Compound 12 (300 mg, 0.534 mmol) was dissolved in CH$_2$Cl$_2$ (3 ml) and added to dry pyridine (5 ml). The reaction mixture was stirred for 5 minutes at room temperature, cooled to −15° C. in an ice bath, and triflic anhydride (Tf$_2$O, 300 mg, 1.067 mmol) was added thereto drop wise over 5 minutes. The ice bath was removed after 15 minutes and the reaction mixture was heated to room temperature. Propagation of the reaction was monitored by TLC (EtOAc/Hexane 1:4), which indicated completion after 1.5 hours. The reaction was diluted with CH$_2$Cl$_2$, and extracted with saturated aqueous NaHCO$_3$, HCl (2%) and brine. The organic layer was dried over MgSO$_4$ and concentrated under reduced pressure. The crude product was purified by flash chromatography to yield Compound 19a (340 mg, yield of 92%).

$^1$H NMR (500 MHz, CDCl$_3$): δ=1.25-1.71 (m, 20H, cyclohexanones), 1.51 (ddd, 1H, $J_1$=$J_2$=$J_3$=12.5 Hz, H-2 axial), 2.39 (dt, 1H, h=5.0, $J_2$=14.0 H-2 equatorial), 3.36

TABLE 7

| Ring | H1 | H2 | H3 | H4 | H5 | H5' | H6 | H6' |
|---|---|---|---|---|---|---|---|---|
| I | 5.51 d<br>J = 3.5 | 3.36-3.39 m | 4.22 t<br>J = 10.5 | 3.99 ddd<br>J = 5.0,<br>10.5, 15.0 | 3.73-3.79 m | | 3.73-3.80 m | 3.53 dd<br>J = 5.0, 10.5 |
| III | 5.70 S | 5.64-5.69 m | 5.64-5.69 m | 4.52 ddd<br>J = 3.5,<br>10.5, 14.5 | 3.87 dd<br>J = 7.0, 13.0 | 3.53 dd<br>J = 3.5, 13.0 | | |

| | H1 | H2eq | H2ax | H3 | H4 | H5 | H6 |
|---|---|---|---|---|---|---|---|
| II | 3.52 ddd<br>J = 4.5,<br>10.0, 14.0 | 2.36 dt<br>J = 5.0, 13.5 | 1.61 ddd<br>$J_1$ = $J_2$ =<br>$J_3$ = 12.5 | 3.66 ddd<br>J = 4.5,<br>11.0, 15.0 | 3.40 t<br>J = 9.5 | 3.50-3.55 m | 3.76-3.80 m |

Additional $^1$H NMR (500 MHz, CDCl$_3$) data for Compound 18b included: δ=7.33 (t, 2H, J=7.5 Hz, Bz), 7.44 (t, 2H, J=7.5 Hz, Bz), 7.52 (t, 1H, J=7.5 Hz, Bz), 7.59 (t, 2H, J=7.5 Hz, Bz), 7.87 (d, 2H, J=7.5 Hz, Bz), 8.03 (d, 2H, J=7.5 Hz, Bz).

$^{13}$C NMR (125 MHz, CDCl$_3$): δ=(C from 22.4-37.8 from cyclohexanones) 22.4, 22.6, 23.7 (2C), 24.8, 25.5, 27.9, 33.9 (C-2), 36.0, 36.3, 37.8, 51.9 (C-5″), 57.2, 60.5, 61.6 (C-6′), 63.2, 64.4, 72.2, 72.3, 75.5, 79.2, 79.3, 80.8, 83.1, 84.1, 97.0 (C-1′), 100.3 (OCO cyclohexanone ketal), 105.0 (C-1″), 113.7 (OCO cyclohexanone ketal), 128.4-133.8 (12C), 165.2, 165.4.

MALDI TOFMS calculated for C$_{43}$H$_{50}$N$_{12}$O$_{12}$Na ([M+Na]$^+$) m/e: 949.4; measured m/e: 949.3.

Preparation of Compound 19a:

(dd, 1H, $J_1$=4.0 $J_2$=10.0 Hz, H-2′), 3.41 (t, J=9.5 Hz, 1H, H-4), 3.51-3.55 (m, 1H, H-3), 3.58 (t, 1H, $J_1$=9.5, $J_2$=10.0 Hz, H-5), 3.66-3.70 (m, 1H, H-1), 3.80 (t, 1H, J=9.5 Hz, H-6), 3.78-3.84 (m, 2H, H-5′, H-6′), 3.96 (dd, 1H, $J_1$=5.0 $J_2$=11.0 Hz, H-6′), 4.00-4.05 (m, 1H, H-4′), 5.07 (t, 1H, J=10.0 Hz, H-3′), 5.63 (d, 1H, J=3.5 Hz, H-1′).

$^{13}$C NMR (125 MHz, CDCl$_3$): δ=(the range 22.4-37.6 relates to cyclohexane rings carbon atoms if not otherwise indicated) 22.1, 22.2, 23.7 (2C), 24.8, 25.5, 27.7, 33.7 (C-2), 36.0, 36.3, 37.6, 57.2, 60.2, 61.0, 61.3 (C-6′), 64.4, 70.9, 77.7, 78.1, 78.3, 79.2, 83.2 (C-3′), 97.7 (C-1′), 100.7 (OCO cyclohexanone ketal), 114.0 (OCO cyclohexanone ketal), ESIMS calculated for C$_{25}$H$_{34}$F$_3$N$_9$O$_9$S Na ([M+Na]$^+$) m/e: 716.2; measured m/e: 716.2.

Preparation of Compound 19:

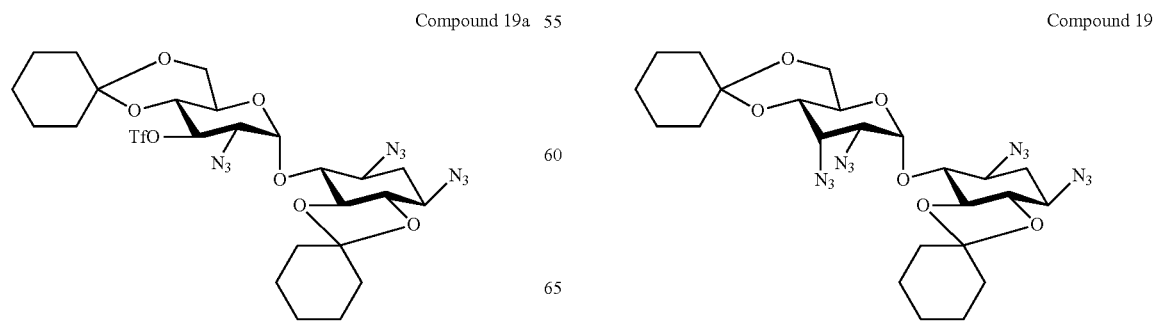

Compound 19a

Compound 19

Compound 19a (330 mg, 0.476 mmol), prepared as presented hereinabove, was dissolved in DMF (2 ml) and hexamethylphosphoramide (HMPA, 1 ml), followed by the addition of $NaN_3$ (310 mg, 4.77 mmol), and the reaction mixture was stirred at 80° C. Propagation of the reaction was monitored by TLC (EtOAc/Hexane, 15:85), which indicated completion after 2 hours. The reaction was diluted with $CH_2Cl_2$, extracted with brine, dried over $MgSO_4$ and concentrated under reduced pressure. The crude product was purified by flash chromatography to yield Compound 19 (200 mg, yield of 72%).

$^1$H NMR (500 MHz, $CDCl_3$) data of Compound 19 are summarized in Table 8 below.

TABLE 8

| Ring | H1 | H2 | H3 | H4 | H5 | H5' | H6 | H6' |
|---|---|---|---|---|---|---|---|---|
| I | 5.44 d<br>J = 4.0 | 3.17 t<br>J = 4.0 | 4.18 t<br>J = 3.5 | 4.30-4.36 m | 3.72-3.78 m | | 3.72-3.78 m | 3.97 dd<br>J = 6.0, 11.0 |
| | H1 | H2eq | H2ax | H3 | H4 | H5 | H6 | |
| II | 3.63-3.66 m | 2.36 dt<br>J = 5.0, 13.5 | 1.48 ddd<br>$J_1 = J_2 =$<br>$J_3 = 12.5$ | 3.53-3.57 m | 3.38 t<br>J = 9.5 | 3.59 t<br>J = 9.5 | 3.75 t<br>J = 9.5 | |

Additional $^1$H NMR (500 MHz, $CDCl_3$) data for Compound 19 included: δ=1.26-1.93 (m, 20H, cyclohexane rings).

$^{13}$C NMR (125 MHz, $CDCl_3$): δ=(the range 22.6-37.6 relates to cyclohexane rings carbon atoms if not otherwise indicated) 22.6 (2C), 23.7 (2C), 24.9, 25.5, 27.8, 34.2 (C-2), 35.9, 36.3, 37.6, 56.9, 57.3, 59.8, 60.4, 60.8, 61.4 (C-6'), 70.9, 77.1, 79.3 (2C), 96.5 (C-1'), 100.0 (OCO cyclohexanone ketal), 113.6 (OCO cyclohexanone ketal).

ESIMS calculated for $C_{24}H_{34}N_{12}O_6Na$ ([M+Na]$^+$) m/e: 609.3; measured m/e: 609.3.

Preparation of Compound 19c:

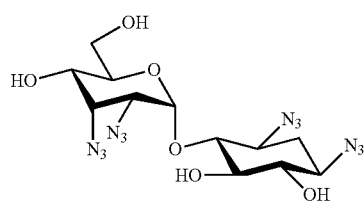

Compound 19c

Compound 19 (200 mg, 0.352 mmol), prepared as presented hereinabove, was dissolved in dioxane (3 ml) and added to acetic acid (8 ml) and water (1 ml), and the reaction mixture was stirred at 75° C. Propagation of the reaction was monitored by TLC (EtOAc/Hexane, 7:3), which indicated completion after 3 hours. The reaction mixture was diluted with EtOAc, washed with saturated aqueous $NaHCO_3$ and brine. The combined organic layer was dried over $MgSO_4$, evaporated under reduced pressure and purified by flash chromatography (silica, EtOAc/Hexane) to yield Compound 19c (90 mg, yield of 60%).

$^1$H NMR (500 MHz, MeOD): δ=1.41 (ddd, 1H, $J_1=J_2=J_3=12.5$ Hz, H-2 axial), 2.39 (dt, 1H, h=4.5, $J_2=13.0$ Hz, H-2 equatorial), 3.27 (t, 1H, J=9.0 Hz, H-4), 3.33 (t, 1H, J=4.0 Hz, H-2'), 3.35-3.50 (m, 3H, H-1, H-3 and H-6), 3.43 (d, 1H, J=3.5 Hz, H-4'), 3.54 (t, 1H, J=9.5 Hz, H-5'), 3.80 (t, 1H, J=9.5 Hz, H-6), 3.79-3.81 (m, 2H, H-6'), 4.14-4.16 (m, 1H, H-3'), 5.55 (d, 1H, J=4.0 Hz, H-1').

$^{13}$C NMR (125 MHz, $CDCl_3$): δ=31.8 (C-2), 57.2, 59.2, 59.7, 60.3 (C-6'), 63.3, 66.2, 67.3, 75.8, 75.9, 78.8, 96.5 (C-1').

MALDI TOFMS calculated for $C_{12}H_{19}N_{12}O_6$ ([M+H]$^+$) m/e: 427.3; measured m/e: 427.3.

Preparation of Compound 20:

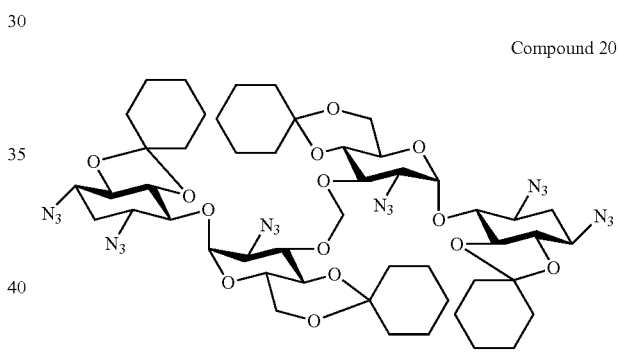

Compound 20

Dry mixture of DMF/HMPA (2:1, 3 ml) was added to powdered, flame-dried 4 Å molecular sieves (500 mg), followed by the addition of the dibromomethane (19 μl, 0.26 mmol) and the acceptor Compound 12 (290 mg, 0.516 mmol) which was prepared as presented hereinabove. The reaction mixture was stirred for 10 minutes at room temperature, cooled to −10° C., and then NaH (19 mg, 0.792 mmol) was added thereto. After 15 minutes of stirring the reaction mixture was heated to 40° C. Propagation of the reaction was monitored by TLC (EtOAc/Hexane, 15:85), which indicated the completion after 2 hours. The reaction was diluted with EtOAc, and filtered through celite. After thorough washing of the celite with EtOAc, the washes were combined and extracted with brine, dried over $MgSO_4$ and concentrated under reduced pressure. The crude was purified by flash chromatography to yield Compound 20 (240 mg, yield of 82%).

$^1$H NMR (500 MHz, $CDCl_3$) data of Compound 20 are summarized in Table 9 below.

TABLE 9

| Ring | H1 | H2 | H3 | H4 | H5 | H5' | H6 | H6' |
|---|---|---|---|---|---|---|---|---|
| I | 5.49 d J = 8.5 | 3.33 dd J = 3.0, 14.0 | 4.09 t J = 4.5 | 3.63-3.67 m | 3.88-3.93 m | | 3.75-3.80 m | 3.88-3.93 m |

| | H1 | H2eq | H2ax | H3 | H4 | H5 | H6 |
|---|---|---|---|---|---|---|---|
| II | 3.62-3.67 m | 2.33 dt J = 5.0, 13.5 | 1.47 ddd $J_1$ = 12 $J_2$ = $J_3$ = 13.0 | 3.43-3.46 m | 3.39 t J = 10 | 3.53 t J = 9.5 | 3.75-3.80 m |

Additional $^1$H NMR (500 MHz, CDCl$_3$) data for Compound 20 included: δ=1.23-1.70 (m, 40H, cyclohexane rings), 5.21 (s, 2H, H-1").

$^{13}$C NMR (125 MHz, CDCl$_3$): δ=(the range 22.4-37.6 relates to cyclohexane rings carbon atoms if not otherwise indicated) 22.4, 23.5 (2C), 24.7, 25.4, 27.5 (C-2), 33.7, 35.8, 36.1, 37.6, 57.0, 60.4, 61.5 (C-6'), 62.1, 63.9, 73.6, 74.1, 78.0, 78.2, 96.6 (C-1" half of other), 97.0 (C-1'), 99.6(OCO cyclohexanone ketal), 115.4 (OCO cyclohexanone ketal).

MALDI TOFMS calculated for $C_{49}H_{70}N_{18}O_{14}Na$ ([M+Na]$^+$) m/e: 1157.5; measured m/e: 1157.4.

Preparation of Compound 20c:

Compound 20c

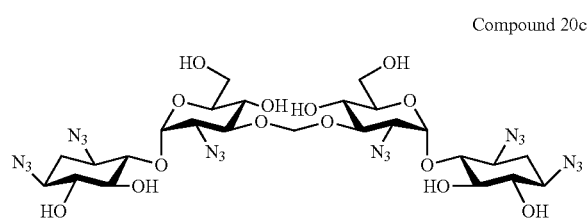

Compound 20 (240 mg), prepared as presented hereinabove), was dissolved in THF (5 ml) and added to a mixture of TFA (1 ml) and water (1.2 ml). The reaction mixture was stirred at 60° C. for 2 hours. Propagation of the reaction was monitored by TLC (EtOAc/Hexane, 9:1). The reaction mixture was purified by flash chromatography (silica, EtOAc/Hexane) to yield Compound 20c (155 mg, yield of 90%).

$^1$H NMR (500 MHz, MeOD): δ=☐☐1.40 (ddd, 1H, $J_1$=12.5, $J_2$=$J_3$=12 Hz, H-2 axial), 2.23 (dt, 1H, $J_1$=5 $J_2$=13.5 Hz, H-2 equatorial), 3.27-3.43 (m, 4H, H-1, H-3, H-4 and H-5), 3.38-3.48 (m, 1H, H-2'), 3.50 (t, 1H, $J_1$=8.5 Hz, H-6), 3.59 (t, 1H, $J_1$=7 Hz, H-5'), 3.76-3.83 (m, 2H, H-4' and H-6'), 3.88-3.95 (m, 1H, H-6'), 3.91 (t, 1H, J=9.5 Hz, H-3'), 5.16 (s, 1H, H-1"), 5.49 (d, 1H, J=3.5 Hz, H-1').

$^{13}$C NMR (125 MHz, MeOD): δ=31.3 (C-2), 61.0, 61.8, 62.8 (C-6'), 65.1, 70.9, 74.2, 77.7, 78.0, 82.1, 82.2, 99.9 (C-1" tether carbon), 99.9 (C-1').

MALDI TOFMS calculated for $C_{25}H_{38}N_{18}O_{14}Na$ ([M+Na]$^+$) m/e: 837.3; measured m/e: 837.2.

Preparation of Compound 2:

Compound 2

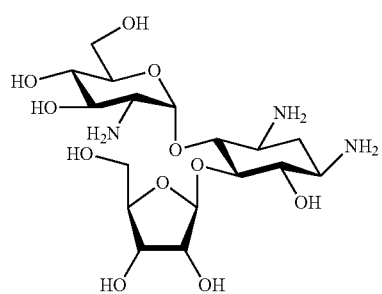

Compound 2 was prepared following the chart presented in FIG. 10, starting from Compound 10 which was converted into Compound 11 and coupled to Compound 15a to afford Compound 16a as described hereinabove.

Compound 16a (450 mg, 0.444 mmol), prepared as presented hereinabove, was treated with a solution of MeNH$_2$ (33% solution in 30 ml EtOH) and the propagation of the reaction was monitored by TLC (EtOAc/MeOH, 7:3), which indicated completion after 8 hours. The reaction mixture was evaporated to dryness under reduced pressure and the residue was dissolved in a mixture of THF (5 ml) and aqueous NaOH (0.1 M, 3.5 ml). This mixture was stirred at room temperature for 10 minutes and thereafter PMe$_3$ (1 M solution in THF, 2.66 ml THF, 2.66 mmol) was added thereto. Propagation of the reaction was monitored by TLC, using a mixture of CH$_2$Cl$_2$/MeOH/H$_2$O/MeNH$_2$ at a relative ratio of 10:15:6:15 diluted to 33% solution in ethanol as eluent, which indicated completion after 5 hours.

The reaction mixture was purified by flash chromatography on a short column of silica gel. The column was washed with the following solvents: THF (100 ml), CH$_2$Cl$_2$ (200 ml), EtOH (100 ml), and MeOH (150 ml). The product was eluted with the mixture of MeNH$_2$ (33% solution in EtOH) and MeOH at a ratio of 1:4. Fractions containing the product were combined and evaporated under reduced pressure, re-dissolved in small volume of water and evaporated again under reduced pressure. This procedure was repeated 2 to 3 times to afford the free amine form of Compound 2 (170 mg, yield of 84%). This product was dissolved in water, the pH was adjusted to 6.5 by H$_2$SO$_4$ (0.01 M) and lyophilized to afford the sulfate salt of Compound 2.

$^1$H NMR (500 MHz, D$_2$O, pH=3.5) data of Compound 2 are summarized in Table 10 below.

TABLE 10

| Ring | H1 | H2 | H3 | H4 | H5 | H5' | H6 | H6' |
|---|---|---|---|---|---|---|---|---|
| I | 5.66 d J = 4.0 | 3.26-3.29 m | 3.83 t J = 10.0 | 3.70-3.73 m | 3.35 t J = 9.0 | | 3.79-3.83 m | 3.66-3.71 m |

TABLE 10-continued

| | | | | | |
|---|---|---|---|---|---|
| III | 5.22 s | 4.08-4.09 m | 4.08-4.09 m | 3.90-3.92 m | 3.77-3.80 m | 3.60 dd J = 5.0, 13.0 |

| | H1 | H2eq | H2ax | H3 | H4 | H5 | H6 |
|---|---|---|---|---|---|---|---|
| II | 3.18-3.23 m | 2.30 dt J = 4.5, 12.5 | 1.65 ddd $J_1 = J_2 = J_3 = 12.5$ | 3.33-3.39 m | 3.56 t J = 9.0 | 3.75-3.81 m | 3.77-3.81 m |

$^{13}$C NMR (125 MHz, D$_2$O): δ=☐☐31.1 (C-2), 50.7, 51.8, 55.8, 62.1 (C-5"), 62.5 (C-6'), 70.7, 70.8, 71.1, 74.4, 75.3, 76.9, 80.4, 84.1, 86.3, 97.8 (C-1");

MALDI TOFMS calculated for C$_{17}$H$_{33}$N$_3$O$_{11}$Na ([M+Na]$^+$) m/e: 478.2; measured m/e: 478.2.

Preparation of Compound 3:

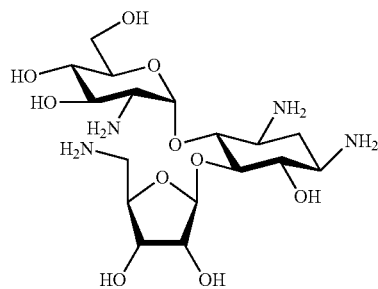

Compound 3

Compound 3 was prepared following the chart presented in FIG. 11, starting from Compound 10 and Compound 14b which were converted into Compound 11 and Compound 15b respectively and coupled to one another to afford Compound 16b as described hereinabove.

Compound 16b (320 mg, 0.342 mmol), prepared as presented hereinabove, was treated with a solution of MeNH$_2$ (33% solution in 30 ml EtOH) and the propagation of the reaction was monitored by TLC (EtOAc/MeOH, 7:3), which indicated completion after 8 hours. The reaction mixture was evaporated to dryness under reduced pressure and the residue was dissolved in a mixture of THF (3.7 ml) and aqueous NaOH (0.1 M, 2.5 ml). This mixture was stirred at room temperature for 10 minutes and thereafter PMe$_3$ (1 M solution in THF, 2.74 ml, 2.74 mmol) was added thereto. Propagation of the reaction was monitored by TLC, using a mixture of CH$_2$Cl$_2$/MeOH/H$_2$O/MeNH$_2$ at a relative ratio of 10:15:6:15 diluted to 33% solution in ethanol as eluent, which indicated completion after 5 hours.

The product was purified as described above for Compound 2 to yield Compound 3 as a free amine (142 mg, yield of 91%).

$^1$H NMR (500 MHz, D$_2$O, pH=3.5) data of Compound 3 are summarized in Table 11 below.

$^{13}$C NMR (125 MHz, D$_2$O): δ=☐☐29.5 (C-2), 43.4 (C-5"), 50.9, 51.7, 55.3, 61.9 (C-6'), 70.8 (2C), 72.8, 73.4, 75.9, 76.4, 77.8, 80.1, 84.2, 95.7 (C-1'), 110.4 (C-1").

MALDI TOFMS calculated for C$_{17}$H$_{33}$N$_4$O$_{10}$Na ([M+Na]$^+$) m/e 477.2; measured m/e 477.5.

Preparation of Compound 4:

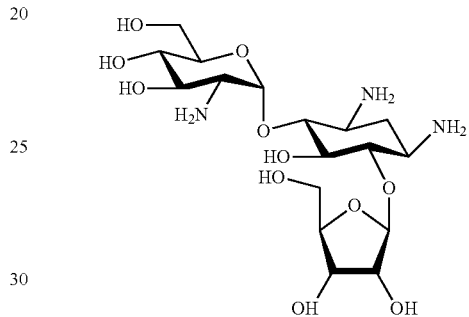

Compound 4

Compound 4 was prepared following the chart presented in FIG. 12, starting from Compound 10 which was converted into Compound 13 which was coupled to Compound 14a to afford Compound 17a as described hereinabove.

Compound 17a (460 mg, 0.43 mmol) was dissolved in THF (3 ml) and added with acetic acid (4.5 ml) and water (0.75 ml). The reaction mixture was stirred at 50° C. for 3 hours and the propagation was monitored by TLC (EtOAc/Hexane, 3:2). The reaction mixture was diluted with EtOAc and washed with saturated NaHCO$_3$ and brine. The combined organic layer was dried over MgSO$_4$ and the mixture was evaporated to dryness under reduced pressure.

The residue was dissolved in THF (4 ml) and was added with the solution of NaOH (0.1 M, 3 ml). The mixture was stirred at room temperature for 10 minutes, after which PMe$_3$ (1 M solution in THF, 2.85 ml, 2.85 mmol) was added. Propagation of the reaction was monitored by TLC, using a mixture of CH$_2$Cl$_2$/MeOH/H$_2$O/MeNH$_2$ at a relative ratio of 10:15:6:15 diluted to 33% solution in ethanol as eluent, which indicated completion after 5 hours. The reaction

TABLE 11

| Ring | H1 | H2 | H3 | H4 | H5 | H5' | H6 | H6' |
|---|---|---|---|---|---|---|---|---|
| I | 5.75 d J = 4.0 | 3.40-3.46 m | 3.94 m J = 9.5 | 3.71-3.73 m | 3.40-3.46 m | | 3.70-3.74 m | 3.82-3.85 m |
| III | 5.31 s | 4.17-4.19 m | 4.15 t J = 10.0 | 4.03-4.08 m | 3.17 dd J = 7.5, 13.5 | 3.28-3.32 m | | |

| | H1 | H2eq | H2ax | H3 | H4 | H5 | H6 |
|---|---|---|---|---|---|---|---|
| II | 3.28-3.32 m | 2.41 dt J = 4.0, 12.5 | 1.83 ddd $J_1 = J_2 = J_3 = 12.5$ | 3.52-3.55 m | 3.69 t J = 9.5 | 3.93 t J = 9.0 | 4.06 t J = 9.0 | mixture was purified by flash chromatography on a short column of silica gel. The column was washed with the following solvents: THF (100 ml), CH$_2$Cl$_2$ (200 ml), EtOH (100 ml), and MeOH (150 ml). The product was eluted with the mixture of MeNH$_2$ (33% solution in EtOH) and MeOH at a ratio of 1:4. The fractions containing the product were evaporated under reduced pressure, redissolved in water and evaporated again, and the procedure was repeated 2 to 3 times to afford Compound 4 in free amine form (147 mg, overall yield of 75%). The product was dissolved in water, the pH was adjusted to 6.65 with H$_2$SO$_4$ (0.01 M) and lyophilized to afford the sulfate salt of Compound 4 as a yellow foamy solid.

$^1$H NMR (500 MHz, D$_2$O, pD 3.0, adjusted by H$_2$SO$_4$ 0.01M) data of Compound 4 are summarized in Table 12 below.

TABLE 12

| Ring | H1 | H2 | H3 | H4 | H5 | H5' | H6 | H6' |
|---|---|---|---|---|---|---|---|---|
| I | 5.61 d J = 4.0 | 3.28 dd J = 4.0, 10.5 | 3.84 t J = 10..0 | 3.70-3.73 m | 3.36 t J = 9.5 | | 3.80-3.87 m | 3.64-3.71 m |
| III | 5.07 s | 4.11 d J = 5.0 | 4.23-4.26 m | 3.91-3.94 m | 3.65-3.69 m | 3.74-3.78 m | | |

| | H1 | H2eq | H2ax | H3 | H4 | H5 | H6 |
|---|---|---|---|---|---|---|---|
| II | 3.22-3.28 m | 2.43 dt J = 4.0, 12.0 | 1.77 ddd J$_1$ = J$_2$ = J$_3$ = 12.5 | 3.42-3.47 m | 3.58 t J = 9.5 | 3.80 t J = 9.5 | 3.84 t J = 9.5 |

$^{13}$C NMR (125 MHz, D$_2$O): δ=□□29.8 (C-2), 49.9, 50.5, 55.8, 60.7 (C-5"), 62.1 (C-6'), 70.3, 70.7, 71.2, 75.4, 76.0, 76.4, 81.1, 82.4, 84.1, 98.5 (C-1'), 110.5 (C-1").

MALDI TOFMS calculated for C$_{17}$H$_{33}$N$_4$O$_{10}$Na ([M+Na]$^+$) m/e: 478.2; measured m/e: 478.2.

Preparation of Compound 5d:

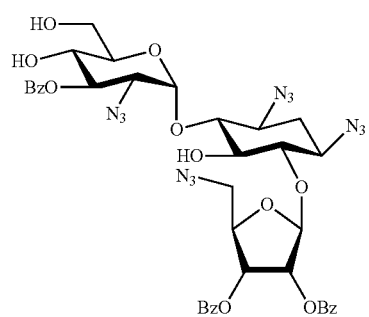

Compound 5d

Compound 17b (400 mg, 0.40 mmol) was dissolved in THF (3 ml) and add to a mixture of TFA (1.5 ml) and water (1 ml). The reaction mixture was stirred at 50° C. for 2 hours during which the propagation was monitored by TLC (EtOAc/Hexane, 1:1). The reaction mixture was directly applied on a silica-gel column and purified by flash chromatography (EtOAc/Hexane) to yield Compound 5d (180 mg, yield of 51.6%).

$^1$H NMR (500 MHz, CDCl$_3$): δ=□□1.49-1.57 (m, 1H, H-2 axial), 2.33-2.37 (m, 1H, H-2 equatorial), 3.33-3.40 (m, 2H, H-3, H-4), 3.45-3.50 (m, 1H, H-1), 3.62 (t, 1H, J=8.5 Hz, H-6), 3.63-3.65(m, 1H, H-5"), 3.70-3.73 (m, 1H, H-2'), 3.74-3.79 (m, 2H, H-5 and H-5"), 3.88 (t, 1H, J=9.5 Hz, H-5'), 3.90-3.92 (m, 2H, H-6'), 4.10-4.13 (m, 1H, H-4'), 4.53-4.56 (m, 1H, H-4"), 5.39 (d, 1H, J=3.5 Hz, H-1'), 5.59 (t, 1H, J=10 Hz, H-3'), 5.62-5.65 (m, 1H, H-3"), 5.71 (d, 1H, J=5 Hz, H-2"), 5.80 (s, 1H, H-1"), 7.34 (t, 2H, J=7.5 Hz), 7.39 (t, 2H, J=7.5 Hz), 7.45 (t, 2H, J=7.5 Hz), 7.51-7.61 (m, 3H), 7.89 (d, 2H, J=7.5 Hz), 7.98 (d, 2H, J=7.5 Hz), 8.07 (d, 2H, J=7.5 Hz).

$^{13}$C NMR (125 MHz, CDCl$_3$): δ=32.2 (C-2), 53.4 (C-5"), 58.5, 58.9, 61.6 (C-6'), 62.3, 69.5, 72.4, 72.6, 75.0, 75.8, 76.3, 79.2, 79.3, 83.2, 99.1 (C-1'), 106.2 (C-1"), 128.4-130.0 (15C), 133.6 (2C), 133.7, 165.5 (2C), 167.2.

MALDI TOFMS calculated for C$_{38}$H$_{38}$N$_{12}$O$_{13}$Na ([M+Na]$^+$) m/e: 893.3; measured m/e: 893.2.

Preparation of Compound 5:

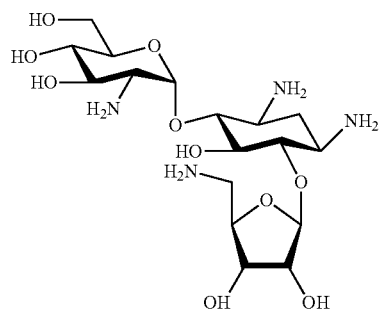

Compound 5

Compound 5 was prepared following the chart presented in FIG. 13, starting from Compound 10 that was converted into Compound 13, which was coupled to Compound 14b to afford Compound 17b, that was converted into Compound 5d as described hereinabove.

Compound 5d (140 mg, 0.16 mmol) was dissolved in THF (3 ml) and was added to a solution of NaOH (0.1M, 2 ml). The reaction mixture was stirred at room temperature for 10 minutes, and thereafter PMe$_3$ (1M solution in THF, 1.65 ml, 1.65 mmol) was added thereto. Propagation of the reaction was monitored by TLC, using a mixture of CH$_2$Cl$_2$/MeOH/H$_2$O/MeNH$_2$ at a relative ratio of 10:15:6:15 diluted to 33% solution in ethanol as eluent, which indicated completion after 5 hours. The reaction mixture was purified by flash chromatography on a short column of silica gel. The column was washed with the following solvents: THF (100 ml), CH$_2$Cl$_2$ (200 ml), EtOH (100 ml), and MeOH (150 ml). The product was eluted with a mixture of MeNH$_2$ (33% solution in EtOH, 30 ml) and MeOH at a ratio of 1:4. The fractions containing the product were evaporated under reduced pressure, redissolved in water and evaporated under reduced pressure. This procedure was repeated 2 to 3 times to afford Compound 5 in free amine form (32 mg, yield of 44%). The amine was dissolved in water, the pH was adjusted to 6.5 with H$_2$SO$_4$ (0.01 M) and lyophilized to give the sulfate salt of Compound 5 as a yellow foamy solid.

$^1$H NMR (500 MHz, D$_2$O, pH=3.0) data of Compound 5 are summarized in Table 13 below.

(dd, 1H, J$_1$=5 J$_2$=12.5 Hz, H-5"), 4.78-4.81 (m, 1H, H-4"), 4.93 (dd, 1H, J$_1$=4 J$_2$=12.5 Hz, H-5"), 5.11 (d, 1H, J=4 Hz, H-1'), 5.55 (s, 1H, H-1"), 5.76 (d, 1H, J=5 Hz, H-2"), 5.87 (t, 1H, J=5 Hz, H-3"), 7.35-7.61 (m, 9H), 7.92 (d, 2H, J=7.5 Hz), 8.02 (d, 2H, J=7.5 Hz), 8.12 (d, 2H, J=7.5 Hz).

$^{13}$C NMR (125 MHz, CDCl$_3$): δ=31.9 (C-2), 52.6, 58.6, 59.4 (C-5"), 62.5, 63.6 (C-6'), 69.2, 71.4, 71.8, 75.1, 75.2, 76.2, 80.1, 83.7, 85.0, 98.9 (C-1'), 107.2 (C-1"), 128.3-129.7 (15C), 133.4, 133.5 (2C), 165.0, 165.2, 166.1;

MALDI TOFMS calculated for C$_{38}$H$_{39}$N$_9$O$_{14}$Na ([M+Na]$^+$) m/e: 868.3; measured m/e: 868.4.

TABLE 13

| Ring | H1 | H2 | H3 | H4 | H5 | H5' | H6 | H6' |
|------|----|----|----|----|----|-----|----|-----|
| I | 5.57 d J = 4.0 | 3.25-3.36 m | 3.80-3.84 m | 3.80-3.84 m | 3.31-3.38 m | | 3.59-3.63 m | 3.67-3.72 m |
| III | 5.19 d J = 1.5 | 3.97-4.06 m | 3.97-4.06 m | 3.97-4.06 m | 3.05-3.10 m | 3.26-3.30 m | | |

| | H1 | H2eq | H2ax | H3 | H4 | H5 | H6 |
|---|----|------|------|----|----|----|----|
| II | 3.31-3.38 m | 2.41-2.44 m | 1.83 ddd J$_1$ = J$_2$ = J$_3$ = 12.5 | 3.42-3.48 m | 3.71-3.72 m | 3.71-3.73 m | 3.82-3.86 m |

$^{13}$C NMR (125 MHz, D$_2$O): δ=☐☐29.7 (C-2), 43.9 (C-5"), 49.8, 50.5, 55.7, 62.1 (C-6'), 70.7, 71.2, 72.8, 75.4, 75.8, 76.0, 79.9, 81.6, 81.8, 98.6 (C-1'), 110.7 (C-1");

TOF APMS calculated for C$_{17}$H$_{34}$N$_4$O$_{10}$ ([M+H]$^+$) m/e: 455.2; measured m/e: 455.2.

Preparation of Compound 6a:

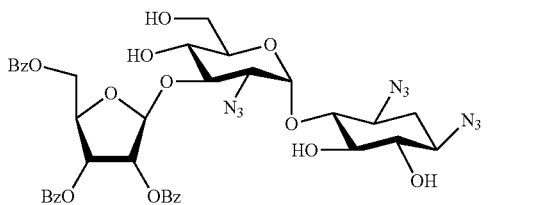

Compound 6a

Compound 18a (240 mg, 0.24 mmol) was dissolved in dioxane (6 ml) and added to a mixture of acetic acid (10 ml) and water (3 ml). The reaction mixture was stirred at 70° C. for 5 hours. Propagation of the reaction was monitored by TLC (EtOAc/Hexane, 7:3). The reaction mixture was diluted with EtOAc and washed with saturated NaHCO$_3$ and brine. The combined organic layer was dried over MgSO$_4$, evaporated under reduced pressure and purified by flash chromatography (silica, EtOAc/Hexane) to yield Compound 6a (215 mg, yield of 75%).

$^1$H NMR (500 MHz, CDCl$_3$): δ=☐1.47 (ddd, 1H, J$_1$=11.5 Hz, J$_3$=J$_2$=12.5 Hz, H-2 axial), 2.30 (dt, 1H, J$_1$=4 J$_2$=13 Hz, H-2 equatorial), 3.21-3.30 (m, 2H, H-3, H-4), 3.35-3.37 (m, 1H, H-2'), 3.40-3.50 (m, 3H, H-1, H-5, H-6), 3.51-3.54 (m, 1H, H-4'), 3.75 (dd, 1H, J$_1$=4 J$_2$=12 Hz, H-6'), 3.82 (dd, 1H, J$_1$=4 J$_2$=12 Hz, H-6'), 3.90-3.96 (m, 2H, H-3', H-5'), 4.57

Preparation of Compound 6:

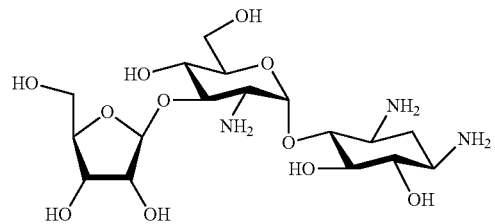

Compound 6

Compound 6 was prepared following the chart presented in FIG. 14, starting from Compound 10 that was converted into Compound 12, which was coupled to Compound 15a to afford Compound 18a, that was converted into Compound 6a as described hereinabove.

Compound 6a (200 mg, 0.236 mmol) was dissolved in THF (3 ml) and was added to a solution of NaOH (0.1M, 1.5 ml). The reaction mixture was stirred at room temperature for 10 minutes, and thereafter PMe$_3$ (1M solution in THF, 1.4 ml, 1.4 mmol) was added thereto. Propagation of the reaction was monitored by TLC, using a mixture of CH$_2$Cl$_2$/MeOH/H$_2$O/MeNH$_2$ at a relative ratio of 10:15:6:15 diluted to 33% solution in ethanol as eluent, which indicated completion after 5 hours. The reaction mixture was purified by flash chromatography on a short column of silica gel. The column was washed with the following solvents: THF (100 ml), CH$_2$Cl$_2$ (200 ml), EtOH (100 ml), and MeOH (150 ml). The product was eluted with a mixture of MeNH$_2$ (33% solution in EtOH, 30 ml) and MeOH at a ratio of 1:4. The fractions containing the product were evaporated under reduced pressure, redissolved in water and evaporated under reduced pressure. This procedure was repeated 2 to 3 times to afford Compound 6 in free amine form (90 mg, yield of 84%). The amine was dissolved in water, the pH was adjusted to 6.5 with H$_2$SO$_4$ (0.01 M) and lyophilized to give the sulfate salt of Compound 6 as a white foamy solid.

$^1$H NMR (500 MHz, D$_2$O, pH=3.5) data of Compound 6 are summarized in Table 14 below.

TABLE 14

| Ring | H1 | H2 | H3 | H4 | H5 | H5' | H6 | H6' |
|---|---|---|---|---|---|---|---|---|
| I | 5.61 d<br>J = 4.0 | 3.47-3.50 m | 3.95-3.97 m | 3.57-3.59 m | 3.68-3.75 m | | 3.74-3.76 m | 3.80-3.83 m |
| III | 5.10 s | 4.09 d<br>J = 4.5 | 4.16-4.19 m | 3.94-3.96 m | 3.60-3.62 m | 3.73-3.76 m | | |

| | H1 | H2eq | H2ax | H3 | H4 | H5 | H6 |
|---|---|---|---|---|---|---|---|
| II | 3.21-3.25 M | 2.39-2.44 m | 1.80 ddd<br>$J_1 = 13.0$<br>$J_2 = J_3 = 12.5$ | 3.45-3.52 m | 3.45-3.52 m | 3.57 t<br>J = 9.0 | 3.80 t<br>J = 10.0 |

$^{13}$C NMR (125 MHz, D$_2$O): δ=☐☐30.0 (C-2), 50.6, 51.4, 54.5, 62.0 (C-5"), 62.5 (C-6'), 69.2, 71.3, 74.0, 75.2, 76.5 (2C), 79.6, 81.8, 84.5, 98.5 (C-1'), 108.7 (C-1").

MALDI TOFMS calculated for C$_{17}$H$_{33}$N$_4$O$_{10}$Na ([M+Na]$^+$) m/e: 478.2; measured m/e: 478.4.

Preparation of Compound 7a:

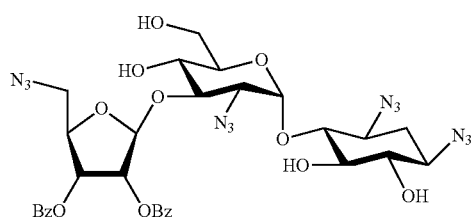

Compound 7a

Compound 18b (500 mg) was dissolved in THF (5 ml) and added to a mixture of TFA (1 ml) and water (1 ml). The reaction mixture was stirred at 50° C. for 2 hours. Propagation of the reaction was monitored by TLC (EtOAc/Hexane, 7:3). The reaction mixture was purified by flash chromatography (silica, EtOAc/Hexane) to yield Compound 7a (340 mg, yield of 82%).

$^1$H NMR (500 MHz, CDCl$_3$): δ=☐☐1.45-1.52 (m, 1H, H-2 axial), 2.26-2.33 (m, 1H, H-2 equatorial), 3.28-3.53 (m, 5H, H-1, H-5, H-6, H-3 and H-4), 3.62 (dd, 1H, $J_1$=3.5 $J_2$=10.0 Hz H-2'), 3.69-3.73 (m, 2H, H-5" and H-5'), 3.85 (dd, 1H, $J_1$=3.0 $J_{26}$=13.5 Hz, H-5"), 3.86-3.96 (m, 3H, H-4' and 2H-6'), 3.99 (t, 1H, $J_1$=9.5 $J_2$=9.0 Hz, H-3'), 4.52-4.55 (m, 1H, H-4"), 5.29 (d, 1H, J=4 Hz, H-1'), 5.55 (s, 1H, H-1"), 5.69 (d, 1H, J=5 Hz, H-2"), 5.70-5.73 (m, 1H, H-3"), 7.35 (t, 2H, J=7.5 Hz), 7.44 (t, 2H, J=7.5 Hz), 7.54 (t, 1H, J=7.5 Hz), 7.60 (t, 1H, J=7.5 Hz), 7.89 (d, 2H, J=8.0 Hz), 8.02 (d, 2H, J=8.0 Hz).

$^{13}$C NMR (125 MHz, CDCl$_3$): δ=32.1 (C-2), 52.3 (C-5"), 58.9, 59.7, 61.0 (C-6'), 62.0, 69.3, 71.5, 72.2, 75.4 (2C), 76.0, 80.3, 83.1, 84.1, 98.8 (C-1'), 106.9 (C-1"), 128.3-135.5 (12C), 165.2, 165.4.

MALDI TOFMS calculated for C$_{31}$H$_{34}$N$_{12}$O$_{12}$Na ([M+Na]$^+$) m/e: 789.2; measured m/e: 789.2.

Preparation of Compound 7:

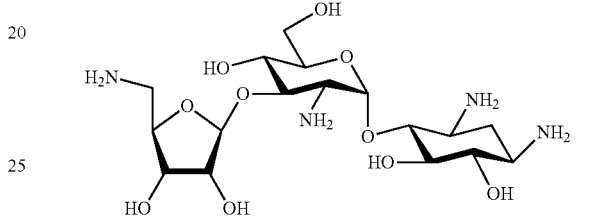

Compound 7

Compound 7 was prepared following the chart presented in FIG. 15, starting from Compound 10 and Compound 14b that were converted into Compound 12 and Compound 15b respectively, that were coupled to one another to afford Compound 18b, which was converted into Compound 7d as described hereinabove.

Compound 7a (300 mg, 0.391 mmol) was dissolved in THF (3 ml) and was added to a solution of NaOH (0.1M, 2 ml). The reaction mixture was stirred at room temperature for 10 minutes, and thereafter PMe$_3$ (1M solution in THF, 3.3 ml, 3.3 mmol) was added thereto. Propagation of the reaction was monitored by TLC, using a mixture of CH$_2$Cl$_2$/MeOH/H$_2$O/MeNH$_2$ at a relative ratio of 10:15:6:15 diluted to 33% solution in ethanol as eluent, which indicated completion after 5 hours. The reaction mixture was purified by flash chromatography on a short column of silica gel. The column was washed with the following solvents: THF (100 ml), CH$_2$Cl$_2$ (200 ml), EtOH (100 ml), and MeOH (150 ml). The product was eluted with a mixture of MeNH$_2$ (33% solution in EtOH, 40 ml) and MeOH at a ratio of 1:4. The fractions containing the product were evaporated under reduced pressure, redissolved in water and evaporated under reduced pressure. This procedure was repeated 2 to 3 times to afford Compound 7 in free amine form (134 mg, yield of 75%). The amine was dissolved in water, the pH was adjusted to 6.6 with H$_2$SO$_4$ (0.01 M) and lyophilized to give the sulfate salt of Compound 7 as a white foamy solid.

$^1$H NMR (500 MHz, D$_2$O, pH=3.5) data of Compound 7 are summarized in Table 15 below.

TABLE 15

| Ring | H1 | H2 | H3 | H4 | H5 | H5' | H6 | H6' |
|---|---|---|---|---|---|---|---|---|
| I | 5.74 d<br>J = 4.0 | 3.53 dd<br>J = 4.0, 11.0 | 4.14-4.19 m | 3.87-3.94 m | 3.56-3.59 m | | 3.77 dd<br>J = 5.0, 12.0 | 3.88-3.94 m |
| III | 5.25 s | 4.23-4.28 m | 4.23-4.28 m | 4.14-4.19 m | 3.16-3.21 m | 3.36-3.40 m | | |

TABLE 15-continued

| | H1 | H2eq | H2ax | H3 | H4 | H5 | H6 |
|---|---|---|---|---|---|---|---|
| II | 3.31-3.37 m | 2.52 dt $J = 4.0, 12.5$ | 1.89 ddd $J_1 = J_2 =$ $J_3 = 12.5$ | 3.56-3.62 m | 3.57-3.63 m | 3.70 t $J_1 = 9.5$ $J_2 = 9.0$ | 3.90-3.93 m |

$^{13}$C NMR (125 MHz, D$_2$O): δ=□□30.0 (C-2), 44.0 (C-5″), 50.6, 51.5, 54.8, 61.9 (C-6′), 70.3, 73.4, 74.1, 73.4, 74.1, 75.4, 76.3, 76.5, 79.4, 80.2, 81.5, 81.6, 98.3 (C-1′), 110.5 (C-1″);

MALDI TOFMS calculated for C$_{17}$H$_{33}$N$_4$O$_{10}$Na ([M+Na]$^+$) m/e: 477.2; measured m/e: 477.2.

Preparation of Compound 8:

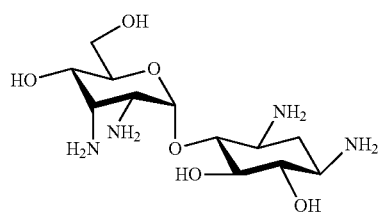

Compound 8

$^{13}$C (NMR 125 MHz, D$_2$O): δ=□□29.8 (C-2), 50.1, 50.9, 51.6, 56.0, 61.2 (C-6′), 64.9, 73.8, 74.0, 75.8, 82.5, 96.8 (C-1′).

MALDI TOFMS calculated for C$_{12}$H$_{26}$N$_4$O$_6$Na ([M+Na]$^+$) m/e: 345.2; measured m/e: 345.2.

Preparation of Compound 9:

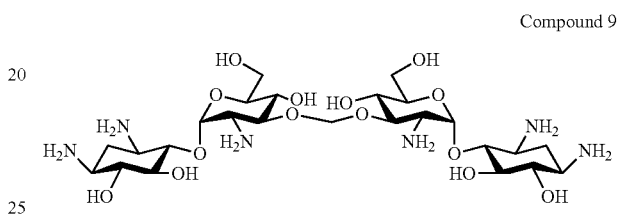

Compound 9

Compound 8 was prepared following the chart presented in FIG. 16, starting from Compound 10 which was converted into Compound 19c as described hereinabove.

Compound 19c (90 mg, 0.211 mmol) was dissolved in THF (3 ml) and was added to a solution of NaOH (0.1M, 2 ml). The reaction mixture was stirred at room temperature for 10 minutes, and thereafter PMe$_3$ (1M solution in THF, 1.69 ml, 1.69 mmol) was added thereto. Propagation of the reaction was monitored by TLC, using a mixture of CH$_2$Cl$_2$/MeOH/H$_2$O/MeNH$_2$ at a relative ratio of 10:15:6:15 diluted to 33% solution in ethanol as eluent, which indicated completion after 5 hours. The reaction mixture was purified by flash chromatography on a short column of silica gel. The column was washed with the following solvents: THF (100 ml), CH$_2$Cl$_2$ (200 ml), EtOH (100 ml), and MeOH (150 ml). The product was eluted with a mixture of MeNH$_2$ (33% solution in EtOH, 30 ml) and MeOH at a ratio of 1:4. The fractions containing the product were evaporated under reduced pressure, redissolved in water and evaporated under reduced pressure. This procedure was repeated 2 to 3 times to afford Compound 8 in free amine form (52.0 mg, yield of 76.5%). The product was dissolved in water, the pH was adjusted to 6.6 with H$_2$SO$_4$ (0.01 M) and lyophilized to afford the sulfate salt of Compound 8.

$^1$H NMR (500 MHz, D$_2$O, pH=3.5) data of 8 are summarized in Table 16 below.

Compound 9 was prepared following the chart presented in FIG. 17, starting from Compound 10 which was converted into Compound 20c as described hereinabove.

Compound 20c (155 mg, 0.208 mmol) was dissolved in THF (3 ml) and was added to a solution of NaOH (0.1M, 2 ml). The reaction mixture was stirred at room temperature for 10 minutes, and thereafter PMe$_3$ (1M solution in THF, 2.28 ml, 2.28 mmol) was added thereto. Propagation of the reaction was monitored by TLC, using a mixture of CH$_2$Cl$_2$/MeOH/H$_2$O/MeNH$_2$ at a relative ratio of 10:15:6:15 diluted to 33% solution in ethanol as eluent, which indicated completion after 5 hours. The reaction mixture was purified by flash chromatography on a short column of silica gel. The column was washed with the following solvents: THF (100 ml), CH$_2$Cl$_2$ (200 ml), EtOH (100 ml), and MeOH (150 ml). The product was eluted with a mixture of MeNH$_2$ (33% solution in EtOH, 30 ml) and MeOH at a ratio of 1:4. The fractions containing the product were evaporated under reduced pressure, redissolved in water and evaporated under reduced pressure. This procedure was repeated 2 to 3 times to afford Compound 9 in free amine form (102 mg, yield of 81.4%). The amine was dissolved in water, the pH was adjusted to 6.5 with H$_2$SO$_4$ (0.01 M) and lyophilized to give the sulfate salt of Compound 9 as a yellow foamy solid.

$^1$H NMR (500 MHz, D$_2$O, pH=3.75) data of Compound 9 are summarized in Table 17 below.

TABLE 16

| Ring | H1 | H2 | H3 | H4 | H5 | H5' | H6 | H6' |
|---|---|---|---|---|---|---|---|---|
| I | 5.37 d $J = 2.0$ | 3.46-3.51 m | 3.98-4.09 m | 3.98-4.09 m | 3.98-4.09 m | | 3.73 d $J = 5.0$ | 3.73 d $J = 5.0$ |

| | H1 | H2eq | H2ax | H3 | H4 | H5 | H6 |
|---|---|---|---|---|---|---|---|
| II | 3.20-3.26 m | 2.42 dt $J = 4.0, 12.5$ | 1.72 ddd $J_1 = J_2 =$ $J_3 = 12.5$ | 3.41-3.52 m | 3.47 t $J = 9.5$ | 3.57 t $J = 9.0$ | 3.80 t $J_1 = 9.5,$ $J_2 = 10.0$ |

TABLE 17

| Ring | H1 | H2 | H3 | H4 | H5 | H5' | H6 | H6' |
|------|-----|-----|-----|-----|-----|-----|-----|-----|
| I | 5.72 d  J = 3.5 | 3.45-3.48 m | 4.11 t  J = 10.0 | 3.79-3.85 m | 3.53-3.57 m | | 3.67-3.69 m | 3.80-3.85 m |

| Ring | H1 | H2eq | H2ax | H3 | H4 | H5 | H6 |
|------|-----|------|------|-----|-----|-----|-----|
| II | 3.24-3.26 m | 2.33 dt  J = 4.0, 13.0 | 1.81 ddd  $J_1 = J_2 = 13.0$  $J_3 = 12.5$ | 3.50-3.53 m | 3.50-3.53 m | 3.65 t  J = 9.5 | 3.84 t  J = 10.0 |

Additional $^1$H NMR (500 MHz, $D_2O$, pH=3.75) data for Compound 9 included: δ=5.12 (s, 1H).

$^{13}$C (NMR 125 MHz, $D_2O$): δ=30.0 (C-2"), 50.5, 51.5, 62.0 (C-6'), 70.6, 74.2, 75.1, 76.6, 79.1, 80.9, 98.1 (C-1'), 99.6 (C-1" tether carbon).

MALDI TOFMS calculated for $C_{25}H_{50}N_6O_{14}Na$ ([M+Na]$^+$) m/e: 681.3; measured m/e: 681.6.

Compound 63 and Compound 10-AHB were prepared from paromamine, via Compound 62 as illustrated in Scheme 9 below.

Scheme 9

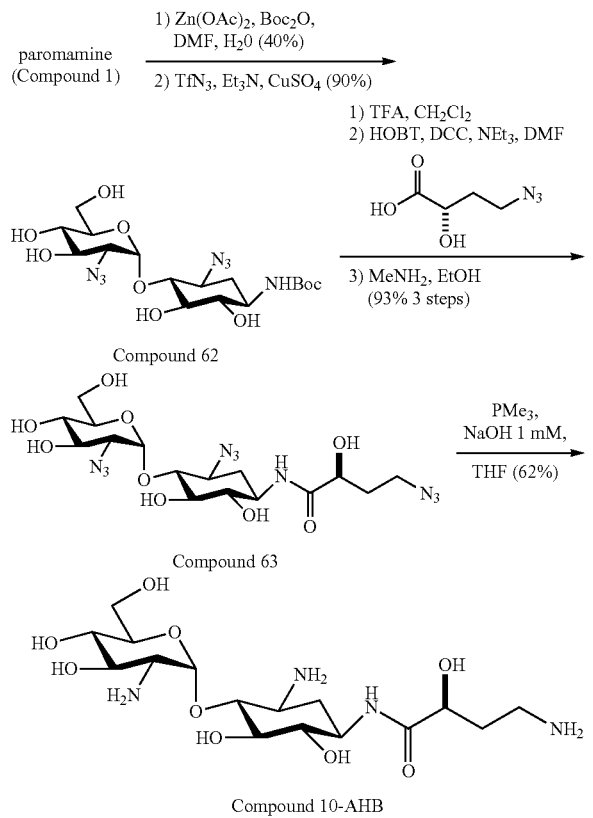

Preparation of Compound 62:

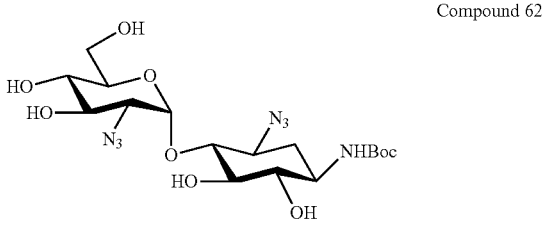

Compound 62

$Zn(OAc)_2$ (14.75 grams, 66 mmol) was added to a stirred solution of paromamine (Compound 1, 9.69 grams, 30 mmol)) in its free base form in $H_2O$ (30 ml) and DMF (150 ml), and the mixture was stirred for 12 hours at room temperature. A solution of di-tert-butyldicarbonate (9.81 grams, 45 mmol) in DMF (20 ml) was added to the reaction mixture over a time period of 30 minutes and the mixture was stirred for an additional 24 hours. The reaction progress was monitored by TLC ($CH_2Cl_2$/MeOH/$H_2O$/MeNH$_2$, 10:15:6:15, 33% solution in EtOH). The reaction mixture was diluted with MeOH (250 ml) and loaded onto 50×300 mm ion-exchange column (Amberlite, CG50, H$^+$ form). The column was washed extensively with 10 column volumes of MeOH/$H_2O$ (60:40) followed by elution with the mixture of MeOH/$H_2O$/NH$_4$OH (80:15:5) to yield the desired N-1-Boc derivative of paromamine at a yield of 40% (5.03 grams).

$^1$H NMR (500 MHz, $D_2O$): "Ring I": δ=2.70 (dd, 1H, $J_1$=3.5, $J_2$=7.0 Hz, H-2), 3.26 (dd, 1H, $J_1$=$J_2$=9.5 Hz, H-4), 3.43 (dd, 1H, $J_1$=$J_2$=9.5 Hz, H-3), 3.62 (dd, 1H, $J_1$=4.0, $J_2$=12.5 Hz, H-6'), 3.69 (dt, 1H, $J_1$=2.0, $J_2$=10.0 Hz, H-5), 3.72 (dd, 1H, $J_1$=4.0, $J_2$=12.5 Hz, H-6), 5.14 (d, 1H, J=4.0 Hz, H-1); "Ring II": δ=1.18 (ddd, 1H, $J_1$=$J_2$=$J_3$=12.5 Hz, H-2ax), 2.51 (dt, 1H, $J_1$=4.5, $J_2$=12.5 Hz, H-2eq), 2.73-2.78 (m, 1H, H-3), 3.15 (dd, 1H, $J_1$=$J_2$=9.5 Hz, H-4), 3.16 (dd, 1H, $J_1$=$J_2$=10.0 Hz, H-6), 3.29-3.37(m, 1H, H-1), 3.58 (dd, 1H, $J_1$=$J_2$=10.0 Hz, H-5); the additional peaks in the spectrum were identified as follows: δ=1.30 (s, 9H, Boc).

$^{13}$C NMR (125 MHz, $D_2O$) "Ring I": δ=56.9 (C-2), 62.4 (C-6), 71.6 (C-4), 74.7 (C-5), 77.7 (C-3), 102.6 (C-1); "Ring II": δ=36.3 (C-2), 50.9 (C-3), 52.0 (C-1), 75.3 (C-5), 76.4 (C-6), 88.6 (C-4); the additional peaks in the spectrum were identified as follows: δ=29.4 (Boc, 3C), 159.6 (Boc, CO).

MALDI TOFMS calculated for $C_{17}H_{33}N_3O_9Na$ ([M+Na]+m/e 446.2; measured m/e 446.5).

Thereafter, the two amino groups in product of the previous procedure (44.3 grams, 0.1 mol) were converted to the corresponding azides by following a published procedure [85], using Tf$_2$O (110 ml, 0.66 mol) and NaN$_3$ (100 grams, 1.53 mol). The reaction progress was monitored by TLC using EtOAc 95% and MeOH 5%, which indicated completion after 8 hours.

The crude product was purified by flash chromatography using silica gel and an eluent gradient of EtOAc 100% to EtOAc/MeOH (95:5) to yield the corresponding diazido Compound 62 at a yield of 90% (42.5 grams).

$^1$H NMR (500 MHz, MeOD): "Ring I": δ=2.88-2.93 (m, 1H, H-2), 3.23 (dd, 1H, $J_1$=$J_2$=9.0 Hz, H-4), 3.49 (d, 2H, $J_1$=3.5 Hz, H-6, H-6'), 3.59-3.63 (m, 2H, H-3, H-5), 5.54 (d, 1H, J=3.5 Hz, H-1); "Ring II": δ=1.08-1.16 (m, 1H, H-2ax), 1.96 (dt, 1H, $J_1$=4.0, $J_2$=12.5 Hz, H-2eq), 2.88-2.93 (m, 1H, H-6), 3.09-3.16 (m, 1H, H-1), 3.12-3.18 (m, 1H, H-3), 3.18 (dd, 1H, $J_1$=$J_2$=9.5 Hz, H-4), 3.23 (dd, 1H, $J_1$=$J_2$=9.0 Hz, H-5); the additional peaks in the spectrum were identified as follows: δ=☐☐1.13 (s, 9H, Boc).

¹³C NMR (125 MHz, MeOD) "Ring I": δ=63.8 (C-6), 66.5 (C-2), 73.1 (C-4), 74.5 (C-3), 75.6 (C-5), 101.2 (C-1); "Ring II": δ=36.2 (C-2), 53.5 (C-1), 62.9 (C-3), 77.6 (C-6), 79.1 (C-5), 83.1 (C-4); the additional peaks in the spectrum were identified as follows: δ=☐☐31.1 (Boc, 3C), 160.0 (Boc, CO).

MALDI TOFMS calculated for $C_{17}H_{29}N_7O_9K$ ([M+K]⁺) m/e 514.2; measured m/e 514.4).

(S)-2-hyroxy-4-azidobutyric acid, or (S)-4-azido-2-hyroxybutanoic acid, was prepared by the azidation of neomycin following a published procedure [85], using (S)-2-hyroxy-4-aminobutyric acid (80 grams, 0.67 mol), Tf₂O (200 ml, 1.20 mol), and NaN₃ (200 grams, 3.00 mol). The reaction progress was monitored by TLC using EtOAc/MeOH (95:5), which indicated completion after 8 hours. The reaction mixture was concentrated, diluted with EtOAc (2.0 L) and extracted with aqueous HCl (2%) and brine. The combined organic layer was dried over MgSO₄ and concentrated to yield (S)-2-hyroxy-4-azidobutyric acid at a yield of 87% (85 grams).

¹H NMR (300 MHz, MeOD) δ=1.67-1.77 (m, 1H), 1.85-1.93 (m, 1H), 3.29 (t, J=7.0 Hz, 2H), 4.05-4.09 (m, 1H).

¹³C NMR (125 MHz, CDCl₃) δ=36.5, 50.8, 70.8, 179.8.

CIMS calculated for $C_4H_7N_3O_3{}^-NH_4{}^+$ ([M+K]+m/e 163.1; measured m/e 163.1).

Preparation of Compound 63:

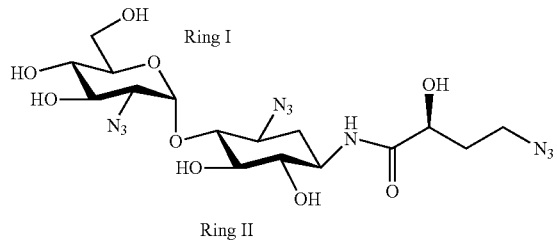

Compound 63

Compound 62 (3.00 grams, 6.31 mmol) was dissolved in a mixture of trifluoroacetic acid (12 ml) and dichloromethane (30 ml). The reaction progress was monitored by TLC using CH₂Cl₂/MeOH (80:20), which indicated completion after 1 hour. The reaction mixture was concentrated to dryness under reduced pressure, and the resulting crude was dissolved in a mixture of Et₃N (10 ml) and DMF (10 ml) and cooled to −20° C. In a separate flask, (S)-2-hyroxy-4-azidobutyric acid (3.94 grams, 31.55 mmol) was dissolved in anhydrous DMF (30 ml), cooled to 0° C., and to the cold solution DCC (7.10 grams, 34.46 mmol) and HOBt (4.72 grams, 34.96 mmol) were added. The resulted mixture was stirred at 0° C. for about one hour. Thereafter, this mixture was carefully added by syringe to the cooled solution of the amine at −20° C. The reaction was stirred at −20° C. for 1 hour and thereafter allowed to warm to room temperature for additional 1 hour. Thereafter, the mixture was treated with a solution of MeNH₂ (33% solution in EtOH, 30 ml) and the reaction progress was monitored by TLC using CH₂Cl₂/MeOH (70:30). After completion of the reaction (about 8 hours) the mixture was concentrated and purified by flash chromatography (MeOH/CH₂Cl₂) to yield Compound 63 at a yield of 93% (3.00 grams).

¹H NMR (500 MHz, MeOD): "Ring I": δ=3.12 (dd, 1H, $J_1$=4.0, $J_2$=10.0 Hz, H-2), 3.45 (dd, 1H, $J_1$=9.5, $J_2$=10.5 Hz, H-4), 3.76-3.83 (m, 2H, H-6, H-6'), 3.92 (dd, 1H, $J_1$=9.0, $J_2$=10.5 Hz, H-3), 3.97-4.00 (m, 1H, H-5), 5.65 (d, 1H, J=3.5 Hz, H-1); "Ring II": δ=1.55 (ddd, 1H, $J_1$=$J_2$=$J_3$=12.5 Hz, H-2ax), 2.18 (dt, 1H, $J_1$=4.0, $J_2$=13.0 Hz, H-2eq), 3.36 (dd, 1H, $J_1$=$J_2$=9.0 Hz, H-6), 3.42-3.48 (m, 1H, H-3), 3.50 (dd, 1H, $J_1$=$J_2$=9.0 Hz, H-4), 3.54 (dd, 1H, $J_1$=$J_2$=9.0 Hz, H-5), 3.77-3.83 (m, 1H, H-1); the additional peaks in the spectrum were identified as follows: δ=☐☐1.82-1.88 (m, 1H, H-9), 2.01-2.07 (m, 1H, H-9), 3.46 (t, 2H, $J_1$=6.5 $J_2$=7.5, H-10), 4.16 (dd, 1H, $J_1$=4.0, $J_2$=8.5, H-8).

¹³C NMR (125 MHz, MeOD) "Ring I": δ=61.0 (C-6), 63.6 (C-2), 70.6 (C-4), 71.3 (C-3), 72.8 (C-5), 98.3 (C-1); "Ring II": δ=32.3 (C-2), 49.1 (C-1), 60.2 (C-3), 74.6 (C-6), 77.4 (C-5), 79.7 (C-4); the additional peaks in the spectrum were identified as follows: ☐δ=33.6 (C9), 47.4 (C10), 69.0 (C8), 175.7 (C7).

MALDI TOFMS calculated for $C_{16}H_{26}N_{10}O_9K$ ([M+K]⁺) m/e 541.2; measured m/e 541.1).

Preparation of Compound 10-AHB:

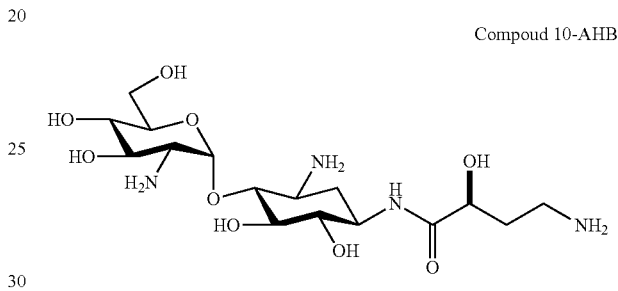

Compoud 10-AHB

Compound 63 (63 mg, 0.125 mmol) was dissolved in a mixture of THF (1.0 ml) and aqueous NaOH (1 mM, 1.5 ml), and was stirred at room temperature for 10 minutes. Thereafter PMe₃ (1 M solution in THF, 1.10 ml, 1.10 mmol) was added, and the reaction progress was monitored by TLC using CH₂Cl₂/MeOH/H₂O/MeNH₂ (33% solution in EtOH, 10:15:6:15), which indicated completion after 1 hour. The reaction mixture was purified by flash chromatography on a short column of silica gel. The column was washed THF (100 ml), CH₂Cl₂ (100 ml), EtOH (50 ml), and MeOH (100 ml). The product was eluted with the mixture of 20% MeNH₂ solution (33% solution in EtOH) in 80% MeOH. Fractions containing the product were combined and evaporated under reduced pressure. The residue was dissolved in a small volume of water and evaporated again (2-3 repeats) to afford the free amine form of Compound 10-AHB.

The analytically pure compound was obtained by further chromatography on the Amberlite CG50 (H±form) column. The column was first washed by MeOH/H₂O 3:2, and then the product was eluted using MeOH/H₂O/NH₄OH (80:10:10) at a yield of 62% (33 mg).

¹H NMR (500 MHz, D₂O, pH=6.5): "Ring I": δ=3.25 (dd, 1H, $J_1$=4.0, $J_2$=11.0 Hz, H-2), 3.45 (dd, 1H, $J_1$=10.0, $J_2$=10.0 Hz, H-4), 3.64-3.66 (m, 1H, H-6), 3.76-3.82 (m, 1H, H-6'), 3.78 (dd, 1H, $J_1$=9.0, $J_2$=10.5 Hz, H-3), 3.80-3.85 (m, 1H, H-5), 5.50 (d, 1H, J=3.5 Hz, H-1); "Ring II": δ=1.60 (ddd, 1H, $J_1$=$J_2$=$J_3$=12.5 Hz, H-2ax), 2.18 (dt, 1H, $J_1$=4.0, $J_2$=12.5 Hz, H-2eq), 3.30-3.35 (m, 1H, H-3), 3.44 (dd, 1H, $J_1$=$J_2$=9.5 Hz, H-6), 3.54 (dd, 1H, $J_1$=$J_2$=9.0 Hz, H-5), 3.67 (dd, 1H, $J_1$=$J_2$=9.0 Hz, H-4), 3.76-3.82 (m, 1H, H-1); the additional peaks in the spectrum were identified as follows: δ=1.88-1.92 (m, 1H, H-9), 2.02-2.08 (m, 1H, H-9), 2.99-3.07 (m, 2H, H-10), 4.21 (dd, 1H, $J_1$=4.0, $J_2$=8.0, H-8).

¹³C NMR (125 MHz, D₂O) "Ring I": δ=56.0 (C-2), 62.2 (C-6), 71.3 (C-4), 71.5 (C-5), 75.2 (C-3), 99.2 (C-1); "Ring II": δ=32.6 (C-2), 50.4 (C-1), 51.1 (C-3), 75.3 (C-6), 77.2

(C-5), 83.6 (C-4); the additional peaks in the spectrum were identified as follows: δ=32.5 (C9), 38.3 (C10), 71.3 (C8), 177.3 (C7).

MALDI TOFMS calculated for $C_{16}H_{32}N_4O_9K$ ([M+K]$^+$) m/e 463.2; measured m/e 463.1.

Compound 64, Compound 65 and Compound 37 (also referred to herein as NB54) were prepared as illustrated in Scheme 10 below.

anhydride (5.2 equivalents, 3.00 ml) was added. The reaction temperature was kept at −12° C. and the reaction progress was monitored by TLC using EtOAc/Hexane (70:30), which indicated completion after 8 hours. The reaction mixture was diluted with EtOAc and extracted with HCl (2%), saturated aqueous $NaHCO_3$, and brine. The combined organic layer was dried over $MgSO_4$ and concentrated. The crude product was purified by flash chromatography using

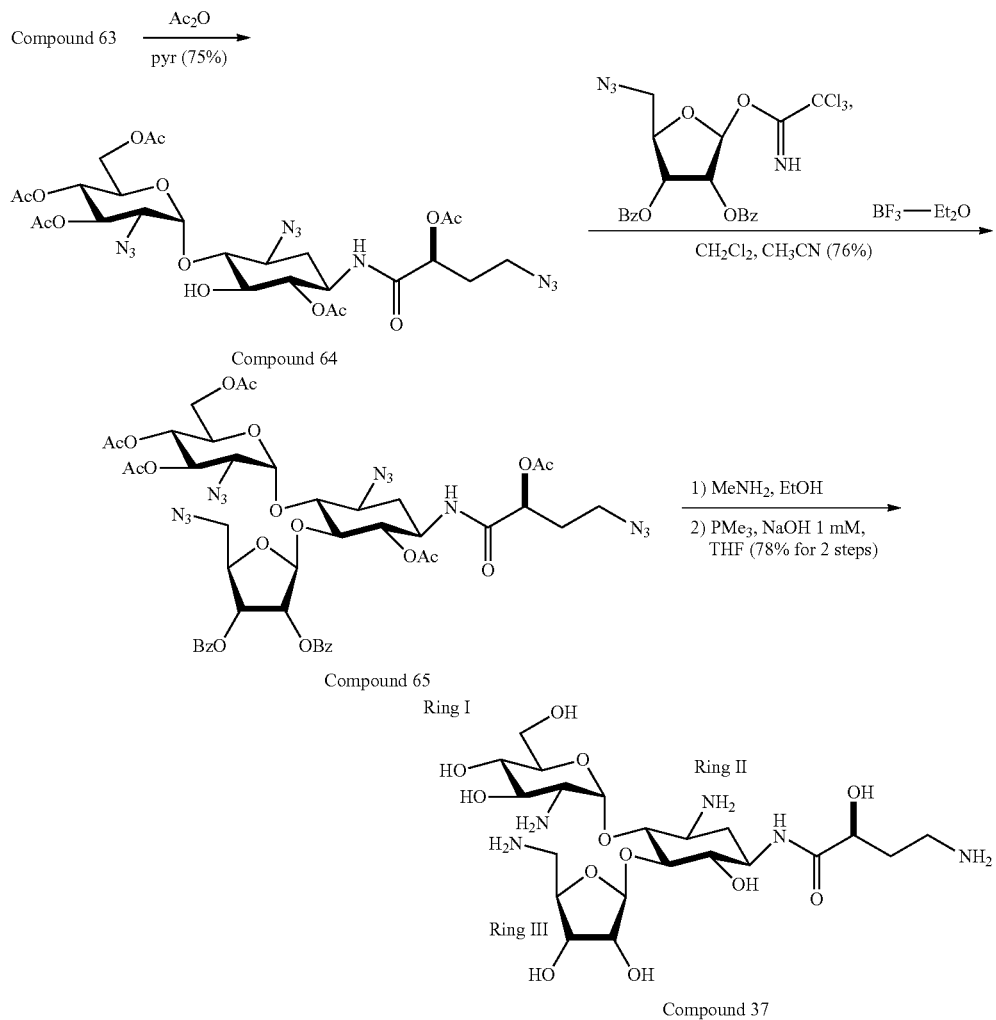

Scheme 10

Preparation of Compound 64:

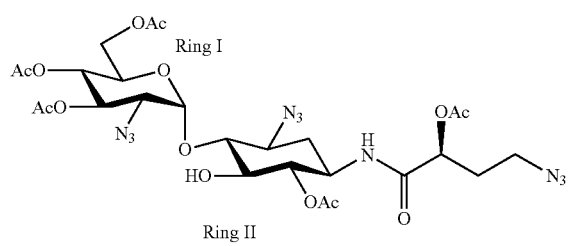

Compound 64

Compound 63 (3.00 grams, 5.85 mmol) was dissolved in dry pyridine (10 ml), cooled at −12° C. and then acetic silica gel and EtOAc/Hexaneas eluent to afford Compound 64 at a yield of 75% (3.15 grams).

$^1$H NMR (500 MHz, $CDCl_3$): "Ring I": δ=3.70 (dd, 1H, $J_1$=3.0, $J_2$=11.0 Hz, H-2), 4.10 (dd, 1H, $J_1$=2.0, $J_2$=12.5 Hz, H-6), 4.31 (dd, 1H, $J_1$=4.5, $J_2$=12.5 Hz, H-6'), 4.36-4.39 (m, 1H, H-5), 5.05 (dd, 1H, $J_1$=10.0, $J_2$=10.0 Hz, H-4), 5.28 (d, 1H, J=3.5 Hz, H-1) 5.50(dd, 1H, $J_1$=10.0, $J_2$=10.0 Hz, H-3); "Ring II": δ=1.48 (ddd, 1H, $J_1$=$J_2$=$J_3$=12.5 Hz, H-2ax), 2.50 (dt, 1H, $J_1$=4.0, $J_2$=13.0 Hz, H-2eq), 3.34-3.39 (m, 1H, H-4), 3.38-3.43 (m, 1H, H-3), 3.74-3.78 (m, 1H, H-5), 3.99-4.04 (m, 1H, H-1), 4.82 (dd, 1H, $J_1$=$J_2$=10.0 Hz, H-6), 6.63 (d, 1H, J=7.5 Hz, NH); the additional peaks in the spectrum were identified as follows: δ=2.05-2.09 (m, 2H, H-9), 2.05 (s, 3H, Ac), 2.08 (s, 3H, Ac), 2.09 (s, 3H, Ac), 2.15 (s, 3H, Ac), 2.19 (s, 3H, Ac), 3.35-3.38 (m, 2H, H-10), 5.14 (dd, 1H, $J_1$=5.5, $J_2$=6.5, H-8).

$^{13}$C NMR (125 MHz, CDCl$_3$) "Ring I": δ=61.8 (C-6), 61.8 (C-2), 68.1 (C-4), 68.4 (C-5), 71.4 (C-3), 99.1 (C-1); "Ring II": δ=32.5 (C-2), 48.2 (C-1), 58.2 (C-3), 73.8 (C-5), 74.0 (C-6), 84.3 (C-4); the additional peaks in the spectrum were identified as follows: □δ=□20.6-20.9 (Ac, 5C), 30.5 (C-9), 47.1 (C-10), 70.8 (C8), 169.1 (C-8, CO), 169.8 (Ac, CO), 169.8 (C-7, CO), 170.0 (Ac, CO), 170.6 (Ac, CO), 172.4 (Ac, CO).

MALDI TOFMS calculated for C$_{26}$H$_{36}$N$_{10}$O$_{14}$K ([M+K]$^+$) m/e 751.1; measured m/e 752.2).

Preparation of Compound 65:

Compound 65

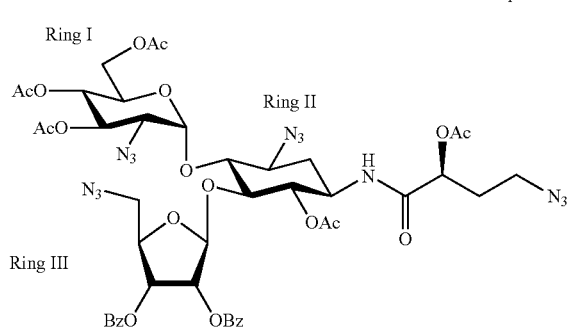

Anhydrous CH$_2$Cl$_2$ (10 ml) was added to powdered, flame-dried 4 Å molecular sieves (3.00 grams), followed by the addition of the acceptor Compound 64 (1.75 grams, 2.46 mmol) and the donor 5-deoxy-5-azido-2,3-di-O-benzoyl-1-O-tricloroacetymido-D-ribofuranose (3.30 grams, 6.27 mmol) dissolved in CH$_3$CN (10 ml). The mixture was stirred for 10 minutes at room temperature and was then cooled down to –20° C. A catalytic amount of BF$_3$-Et$_2$O (100 μl) was added to the reaction mixture, and the mixture was stirred at –15° C. The reaction progress was monitored by TLC using EtOAc/Hexane (60:40), which indicated completion after 30 minutes. The reaction was diluted with CH$_2$Cl$_2$ and filtered through celite. After thorough washing of celite with CH$_2$Cl$_2$, the washes were combined and extracted with saturated aqueous NaHCO$_3$, brine, dried over MgSO$_4$ and concentrated. The crude product was purified by flash chromatography to afford Compound 65 at a yield of 76% (2.01 grams) and Compound 64 at a yield of 20% (350 mg).

$^1$H NMR (500 MHz, CDCl$_3$): "Ring I": δ=3.53 (dd, 1H, J$_1$=4.0, J$_2$=11.0 Hz, H-2), 4.15 (dd, 1H, J$_1$=2.0, J$_2$=12.5 Hz, H-6), 4.26 (dd, 1H, J$_1$=4.0, J$_2$=12.5 Hz, H-6'), 4.50-4.55 (m, 1H, H-5), 5.07 (dd, 1H, J$_1$=9.5, J$_2$=10.0 Hz, H-4), 5.43 (dd, 1H, J$_1$=9.5, J$_2$=10.0 Hz, H-3), 5.83 (d, 1H, J=4.0 Hz, H-1); "Ring II": δ=1.47 (ddd, 1H, J$_1$=J$_2$=J$_3$=12.5 Hz, H-2ax), 2.50 (dt, 1H, J$_1$=4.0, J$_2$=13.0 Hz, H-2eq), 3.56-3.58 (m, 1H, H-3), 3.72 (dd, 1H, J$_1$=8.5, J$_2$=9.5 Hz, H-4), 3.99 (dd, 1H, J$_1$=8.5, J$_2$=9.5 Hz, H-5), 4.01-4.08 (m, 1H, H-1), 4.91 (dd, 1H, J$_1$=9.5, J$_2$=10.5 Hz, H-6), 6.64 (d, 1H, J=8.5 Hz, NH); "Ring II" I: δ=3.57 (dd, 1H, J$_1$=6.0, J$_2$=13.0 Hz, H-5'), 3.64 (dd, 1H, J$_1$=3.0, J$_2$=13.0 Hz, H-5), 4.50-4.55 (m, 1H, H-4), 5.49 (dd, 1H, J$_1$=5.0, J$_2$=7.0 Hz, H-3), 5.62 (dd, 1H, J$_1$=1.0, J$_2$=5.0 Hz, H-2), 5.68 (d, 1H, J=1.0 Hz, H-1); the additional peaks in the spectrum were identified as follows: δ=□□2.00-2.15 (m, 2H, H-9), 2.04 (s, 3H, Ac), 2.09 (s, 6H, 2Ac), 2.20 (s, 3H, Ac), 2.23 (s, 3H, Ac), 3.35 (t, 2H, J=7.0, H-10), 5.16 (dd, 1H, J$_1$=5.0, J$_2$=7.0 Hz, H-8), 7.33 (t, 2H, J=8.0, Bz), 7.43 (t, 2H, J=8.0, Bz), 7.51-7.54 (m, 1H, Bz), 7.56-7.60 (m, 1H, Bz), 7.85 (d, 2H, J=1, 7.5, Bz), 7.94 (dd, 2H, J=1, 7.5, Bz).

$^{13}$C NMR (125 MHz, CDCl$_3$) "Ring I": δ=61.6 (C-2), 61.8 (C-6), 68.1 (C-5), 68.2 (C-4), 70.7 (C-3), 96.8 (C-1); "Ring II": δ=32.1 (C-2), 48.4 (C-1), 58.5 (C-3), 73.5 (C-6), 77.9 (C-4), 80.0 (C-5); "Ring II" I: δ=52.7 (C-2), 71.5 (C-3), 74.7 (C-2), 80.1 (C-4), 107.4 (C-1); the additional peaks in the spectrum were identified as follows: □δ=□20.6-20.9 (Ac, 5C), 30.5 (C-9), 47.1 (C-10), 70.9 (C8), 128.4 (Bz, 2C), 128.5 (Bz, 2C), 129.6 (Bz, 2C), 129.7 (Bz, 2C), 133.6 (Bz, 1C), 133.7 (Bz, 1C), 165.2 (Bz, CO), 165.2 (Bz, CO), 168.9 (C-8, CO), 169.7 (Ac, CO), 169.7 (C-7, CO), 169.9 (Ac, CO), 170.6 (Ac, CO), 172.3 (Ac, CO).

MALDI TOFMS calculated for C$_{45}$H$_{51}$N$_{13}$O$_{19}$K ([M+K]$^+$) m/e 1116.3; measured m/e 1116.3.

Preparation of Compound 37:

Compound 37

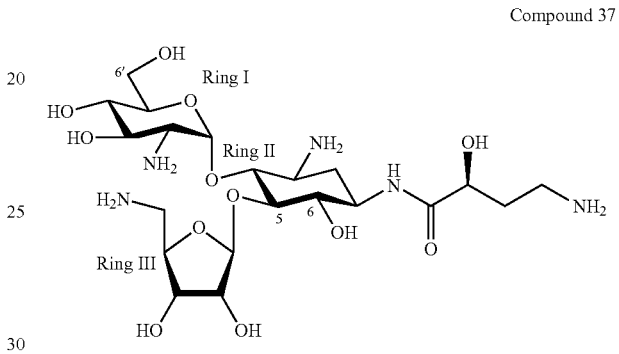

Compound 65 (1.55 grams, 1.44 mmol) was treated with a solution of MeNH$_2$ (33% solution in EtOH, 50 ml) and the reaction progress was monitored by TLC using EtOAc/MeOH (85:15), which indicated completion after 8 hours. The reaction mixture was evaporated to dryness and the residue was dissolved in a mixture of THF (5 ml) and aqueous NaOH (1 mM, 5.0 ml). This mixture was stirred at room temperature for 10 minutes, after which PMe$_3$ (1 M solution in THF, 11.52 ml, 11.52 mmol) was added. The reaction progress was monitored by TLC using CH$_2$Cl$_2$/MeOH/H$_2$O/MeNH$_2$ (33% solution in EtOH) (10:15:6:15), which indicated completion after 1 hour.

The reaction mixture was purified by flash chromatography on a short column of silica gel. The column was washed with the following solvents: THF (800 ml), CH$_2$Cl$_2$ (800 ml), EtOH (200 ml), and MeOH (400 ml). The product was then eluted with the mixture of 20% MeNH$_2$ solution (33% solution in EtOH) in 80% MeOH. Fractions containing the product were combined and evaporated under reduced pressure. The residue was re-dissolved in a small volume of water and evaporated again (2-3 repeats) to afford the free amine form of Compound 37 (also referred to as NB54).

The analytically pure product was obtained by eluting the above product through a short column of Amberlite CG50 (NH$_4$$^+$ form). The column was first washed with MeOH/H$_2$O (3:2), then the product was eluted with a mixture of MeOH/H$_2$O/NH$_4$OH (80:10:10) to afford Compound 37 at a yield of 78% (628 mg).

The product was dissolved in water, the pH was adjusted to 6.5 by H$_2$SO$_4$ (0.1 N) and lyophilized to afford the sulfate addition salt of Compound 37, which was used in all biological studies.

$^1$H NMR (500 MHz, D$_2$O, pH=3.5): "Ring I": δ=3.52 (dd, 1H, J$_1$=4.0, J$_2$=11.0 Hz, H-2), 3.53-3.57 (m, 1H, H-4), 3.81-3.85 (m, 1H, H-5), 3.81-3.85 (m, 1H, H-6), 3.93-3.98 (m, 1H, H-6'), 4.04 (dd, 1H, J$_1$=9.0, J$_2$=10.0 Hz, H-3), 5.87

(d, 1H, J=4.0 Hz, H-1); "Ring II": δ=1.80 (ddd, 1H, $J_1=J_2=J_3$=12.5 Hz, H-2ax), 2.24 (dt, 1H, $J_1$=4.0, $J_2$=12.5 Hz, H-2eq), 3.54-3.58 (m, 1H, H-3), 3.73 (dd, 1H, $J_1=J_2$=9.5 Hz, H-6), 3.92-3.98 (m, 1H, H-1), 3.99 (dd, 1H, $J_1=J_2$=9.0 Hz, H-5), 4.11 (dd, 1H, $J_1=J_2$=9.5 Hz, H-4); "Ring III": δ=3.29 (dd, 1H, $J_1$=7.0, $J_2$=13.5 Hz, H-5), 3.42 (dd, 1H, $J_1$=4.0, $J_2$=13.5 Hz, H-5'), 4.12-4.15 (m, 1H, H-4), 4.23-4.25 (m, 1H, H-3), 4.26-4.29 (m, 1H, H-2), 5.40 (s, 1H, H-1); the additional peaks in the spectrum were identified as follows: δ=□□1.98-2.06 (m, 1H, H-9), 2.15-2.22 (m, 1H, H-9), 3.14-3.23 (m, 2H, H-10), 4.34 (dd, 1H, $J_1$=4.0, $J_2$=8.5, H-8).

$^{13}$C NMR (125 MHz, $D_2O$) "Ring I": δ=55.4 (C-2), 61.9 (C-6), 70.8 (C-3), 70.8 (C-4), 75.8 (C-5), 95.7 (C-1); "Ring II": δ=31.4 (C-2), 50.4 (C-3), 51.4 (C-1), 74.6 (C-6), 78.1 (C-4), 85.1 (C-5); "Ring III": δ=43.4 (C-5), 72.7 (C-3), 76.5 (C-3), 79.9 (C-4), 110.5 (C-1); the additional peaks in the spectrum were identified as follows: □δ=□32.6 (C9), 38.4 (C10), 71.3 (C8), 177.4 (C7).

MALDI TOFMS calculated for $C_{21}H_{41}N_5O_{12}K$ ($[M+K]^+$) m/e 594.3; measured m/e 594.3.

Example 2

Biological Activity Assays

The ability of the compounds presented herein, i.e., Compounds 2-9, to read-through stop codon mutations was examined both in-vitro and ex-vivo in mammalian cultured cells.

All chemicals and reagents were obtained from common commercial sources unless otherwise stated. The commercial antibiotics, paromomycin and gentamicin were obtained from Sigma.

In Vitro Translation Reactions and Quantification of Suppression and Translation:

The mutation suppression activity assays were performed on "UGA C" mutation, which was shown to be most susceptible for aminoglycoside-mediated suppression. Initially, Compounds 1-9 were tested for their ability to suppress this nonsense mutation in vitro, using a reporter construct carrying the R3X nonsense mutation (a premature UGA C stop codon) of the PCDH15 gene. Mutations in the PCDH15 gene which encodes protocardherin 15, cause type f Usher syndrome (USH1), which is characterized by profound prelingual hearing loss, vestibular areflexia, and prepubertal onset of retinitis pigmentosa (RP) [87]. Four different PCDH15 USH1-causing nonsense mutations, R3X, $R_{245}X$, $R_{643}X$, and $R_{929}X$, have been reported in humans. Interestingly, while the above nonsense mutations of PCDH15 cause USH1, certain missense mutations in the same gene cause only nonsyndromic, deafness, which is not associated with RP. Such observations suggest that partial or low level activity of the protein encoded by this gene may be sufficient for normal retinal function, making any of the compounds presented herein a suitable candidate for read-through therapy.

Suppression of nonsense mutations by Compounds 1-9 was tested in vitro using a reporter plasmid harboring the R3X mutation of the PCDH15 gene [88]. To create this plasmid, the oligonucleotides 5'-GATCCATGTTTTGACA-GTTTTATCTCTGGACA-3' (SEQ ID NO: 1) and 5'-AGCT-TGTCCAGAGATAAAACTGTCAAAACATG-3' (SEQ ID NO: 2) were annealed to each other and inserted into the BamHI and HindIII sites of plasmid pDB650 [6].

The resulting reporter plasmid pDB650-R3X contained a TGA C nonsense mutation between a 25-kDa polypeptide encoding open reading frame (ORF) and a 10-kDa polypeptide encoding ORF. Hence, an efficient translation termination at the stop codon resulted in the production of a 25-kDa polypeptide, while suppression of the nonsense mutation by the compounds tested herein allowed the synthesis of a longer 35-kDa protein.

The plasmid was transcribed and translated in a rabbit reticulocyte lysate coupled transcription/translation system (Promega) in the presence of [$^{35}$S]-methionine, and the reaction products were separated by SDS-PAGE and quantified using PhosphorImager analysis. The mutation suppression level was calculated as the relative proportion of the 35-kDa product out of total protein (the sum of 35-kDa and 25-kDa), and the translation level was calculated as the relative proportion of the total protein at each tested compound concentration out of the total protein without the presence of the tested compounds.

The mutation suppression activities of paromomycin and gentamicin were measured and used as reference to the activity of the compounds presented herein. The tested concentrations of paromomycin were 0, 5, 10, 20, 30 and 40 μg/ml, tested concentrations of gentamicin were 0, 5, 10, 20, and 30 μg/ml, and the tested concentrations of Compounds 1-9 were in the range of 0-160 μg/ml. The concentrations at which maximal suppression levels were observed are given in Table 18 below.

Using similar methods for testing and analyses, compounds which exhibit an N1-AHB group as presented hereinabove are tested for mutation suppression activity.

Table 18 presents maximal in-vitro mutation suppression and translation levels of the R3X mutation, along with the MIC values measured for Compounds 1-9. The results in Table 18 are reported as averages of at least three independent experiments.

TABLE 18

| Compound | Conc. [μg ml$^{-1}$] | Supp. level (%) | Trans. level (%) | MIC [μg ml$^{-1}$] E. coli | MIC [μg ml$^{-1}$] B. Subtilis |
|---|---|---|---|---|---|
| Paromomycin | 40 | 49 ± 6 | 40 ± 13 | 12 | 8 |
| Gentamicin | 30 | 49 ± 4 | 40 ± 9 | 4 | <0.5 |
| Paromamine (Compound 1) | 80 | 6.2 ± 0.2 | 74 ± 15 | 512 | 128 |
| Compound 2 | 80 | 1.3 ± 0.1 | 100 ± 10 | 256 | 64 |
| Compound 3 | 80 | 21 ± 3 | 72 ± 6 | >512 | 48 |
| Compound 4 | 80 | 1.5 ± 0.1 | 74 ± 7 | 256 | 96 |
| Compound 5 | 80 | 4.4 ± 2 | 75 ± 9 | >512 | 192 |
| Compound 6 | 160 | <1 | 82 ± 8 | >512 | >512 |
| Compound 7 | 80 | 2.9 ± 2 | 98 ± 10 | 192 | 48 |
| Compound 8 | 80 | 2.0 ± 2 | 71 ± 7 | 192 | 48 |
| Compound 9 | 80 | <1 | 22 ± 2 | 96 | 48 |

As can be seen in Table 18, removal of either one ring which is present in paromomycin, namely ring IV as in the case of Compound 2, or two rings which are present in paromomycin, namely rings III and IV as in the case of Compound 1, dramatically decreases its in vitro read-through activity from 49% suppression to 1.6% (Compound 2) and 6.2% (Compound 1). These data alone indicate that ring IV of paromomycin is critical for its proper recognition of the mammalian A-site and for its subsequent read-through activity. The substantially higher suppression level of Compound 1 (6.2%) compared to that of the Compound 2 (1.6%) implies that Compound 1 (paromamine) represents the minimal structural motif of paromomycin that is preferentially recognized by the mammalian ribosome and has significant suppression activity.

As can further be concluded from Table 18, connection of the plain ribose ring to the paromamine scaffold either at the C6 position, as in Compound 4, or at the C3' position as in Compound 6, along with the addition of one extra amine as in Compound 8, or paromamine dimerization as in Compound 9, gave lower suppression levels than that of paromamine itself.

The most important results, however, were observed when instead of plain ribose the 5-amino ribose (ribosamine) was connected to the paromamine moiety at different positions. As can be also seen in Table 18, the observed mutation suppression levels of Compounds 3, 5, and 7 were higher than the corresponding compounds containing plain ribose ring at the same position, namely Compounds 2, 4, and 6 respectively. In addition, in the series of Compounds 3, 5, and 7, a particular influence of the position of the ribosamine on the paromamine scaffold was observed to be C5 (Compound 3)>>C6 (Compound 5)>C3' (Compound 7), suggesting that the preservation of the pseudo-trisaccharide core structure of the parent paromomycin (rings I-III) in Compound 3 is important for efficient read-through activity.

The mutation suppression data of Compounds 1-9 show that, although in the series of Compounds 2-7, an increased number of amino groups in each pair leads to improved read-through activity, the data obtained with Compound 8 and Compound 9 indicate that merely increasing the number of amino groups on the paromamine scaffold does not always lead to an increase in read-through activity, even though the binding affinity of these analogs to both prokaryotic and eukaryotic rRNA is likely to be increased [36, 89]. Nevertheless, the observed 13-fold higher suppression level of Compound 3 compared to that of the corresponding ribose Compound 2, and over 3-fold higher activity compared to that of Compound 1, suggest that the presence of C5"-NH$_2$ group in Compound 3 is responsible for its elevated read-through activity.

FIGS. 3a-d present the results of the in vitro mutation suppression and translation assays measured for the exemplary Compound 3, and paromomycin, by expression of a plasmid-based reporter construct containing a TGA C nonsense stop mutation between a 25-kDa polypeptide encoding open reading frame (ORF) and a 10-kDa polypeptide encoding ORF, in the presence of the tested compounds and [$^{35}$S]-methionine, showing the reaction products separated by SDS-PAGE and quantified using a phosphor-imager for Compound 3 (FIG. 3a) and paromomycin (FIG. 3c), and showing comparative plots where the mutation suppression values (shown in black dots) and the translation values (shown in white dots), calculated as the relative proportion of the total protein at each concentration of the tested compounds out of the total protein expressed in the absence thereof, as measured in triplicates for Compound 3 (FIG. 3b) and for paromomycin (FIG. 3d).

As can be seen in Table 18 and FIGS. 3a-3d, besides its very significant read-through activity, Compound 3 also retained about two-fold higher translation level (about 80%, see also Table 18) than either paromomycin (about 40%) or gentamicin (about 40%), at the concentrations in which each tested compound reached maximal suppression rate. Such a reduction in translation inhibition by Compound 3 could be interpreted as a reduced toxicity of Compound 3 relative to that of the parent paromomycin or gentamicin compounds. Thus, although at the above concentrations the paromomycin-induced suppression rate is higher than that of Compound 3, the amount of total protein produced in the case of Compound 3 is larger.

Ex Vivo Mutation Suppression Induced by Aminoglycoside Antibiotics:

While further reducing the present invention to practice, it was reasoned that the protein production enhancement exhibited by Compound 3, even at the observed suppression rate, could in principle increase the efficacy of drug-induced nonsense suppression in mammalian cell systems, by increasing the total amount of functional proteins produced from nonsense codon-containing genes. Recent studies on enhanced production of functional proteins from nonsense codon-containing genes by promoter-activating agents support this presumption [33]. To test this possibility, Compound 3 along with paromomycin and gentamicin, were evaluated for the UGA C stop codon read-through activity in cultured cells using a dual luciferase reporter system.

Suppression of nonsense mutations by Compounds 1-9 was tested ex vivo using a dual luciferase reporter plasmid [90]. The p2LUC plasmid harboring the UGAC mutation was transfected to COS-7 cells with Lipofectamine 2000 (Invitrogen) and addition of tested compounds was performed after 15 hours. Luciferase activity was determined after 24 hours of incubation, using the Dual Luciferase Reporter Assay System (Promega) and stop codon readthrough was calculated as described previously.

Using similar methods for testing and analyses, compounds which exhibit an N1-AHB group as presented hereinabove are tested for ex-vivo mutation suppression activity.

FIG. 4 presents the ex-vivo suppression of a nonsense mutation exhibited by the exemplary Compound 3, paromomycin and gentamicin, using the p2Luc plasmid containing a TGA C nonsense mutation in a polylinker between the renilla luciferase and firefly luciferase genes expressed in COS-7 cells, showing the calculated suppression levels as averages of three independent experiments or more for each tested compound at different concentrations.

As can be seen in FIG. 4, the activity of Compound 3 is superior to that of paromomycin and gentamicin at all the tested concentrations. In the compounds tested, the induced read-through activity increased with the increased concentration of the tested compound, but this increase was more significant in the case of Compound 3 than the other two clinically used drugs. As can further be seen in FIG. 4, gentamicin, which is currently the only clinically relevant aminoglycoside shown to have the ability to suppress nonsense mutations in patients, was less efficient than either paromomycin or Compound 3. Such an increased read-through effectiveness of Compound 3 relative to those of paromomycin and gentamicin is most likely caused due to its lower toxicity with respect to the cultured cells.

Antibacterial Activity:

In order to compare the observed aminoglycoside-induced stop codon read-through activity in mammalian cells to antibacterial activity thereof, Compounds 1-9 were further investigated as antibacterial agents against both Gram-negative (*E. coli*) and Gram-positive (*Bacillus subtilis*) bacteria, and the minimal inhibitory concentration (MIC) values were determined by using a microdilution assay with paromomycin and gentamicin as controls, and the results are presented in Table 18 hereinabove.

The bacterial strains used were *Escherichia coli* ATCC 25922, and *Bacillus Subtilis* ATCC 6633. The MIC values were determined using the double-microdilution method according to the National Committee for Clinical Laboratory Standards (NCCLS) [91] with two different starting concentrations of the tested compounds, 384 µg/ml and 512 µg/ml.

All the experiments were performed in triplicates and analogous results were obtained in two to four different experiments.

Using similar methods for testing and analyses, compounds which exhibit an N1-AHB group as presented hereinabove are tested for antimicrobial activity.

As can be deduced from the MIC values presented in Table 18, the antibacterial activity of all the compounds presented herein is markedly lower than that of the parent compound paromomycin by a factor which ranges from 8 to 43 in *E. coli* and from 6 to 64 in *B. subtilis*, whereas gentamicin and paromomycin exhibited excellent antibacterial activity against both bacterial strains.

Most importantly, the considerably lower antibacterial activity of Compound 3 compared to that of paromomycin indicates that the selectivity of Compounds 3 to the eukaryotic cells is much higher than that of the parent paromomycin. Thus, the observed inability of Compounds 3 to show significant antibacterial activity should be interpreted as a positive result in the sense of the general applicability of the strategy outlined herein for the design of new variants of aminoglycosides that can act selectively on the mammalian ribosome and cause efficient stop codon suppression without upsetting the GI biota equilibrium or increasing the emergence of resistance to antibiotics.

Cytotoxicity in Mammalian System:

To further confirm the reduced toxicity of Compound 3 with reference to commercially available and clinically-used aminoglycosides, a series of cell toxicity assays was performed using three kidney-derived cell lines, i.e., HEK-293 (human embryonic kidney), COS-7 (monkey kidney), and MDCK (canine kidney), as described hereinbelow.

HEK-293, COS-7 or MDCK were grown in 96-well plates (5000 cells/well) in DMEM medium containing 10% FBS, 1% penicillin/streptomycin and 1% glutamine (Biological Industries) at 37° C. and 5% $CO_2$ over night. After 1 day the medium was changed to medium without streptomycin and different concentrations of the tested compounds were added. After 48 hours a cell proliferation assay (XTT based colorimetric assay, Biological Industries) was performed, using the 5 hours incubation protocol, according to the manufacturer's instructions. Optical density (OD) was read using an Elisa plate reader. Cell viability was calculated as the ratio between the number of living cells in cultures grown in the presence of the tested compounds, versus the corresponding cell cultures which were grown without the tested compounds. The concentration of half-maximal lethal dose for cells ($LC_{50}$) was obtained from fitting concentration-response curves to the data of at least two independent experiments, using Grafit 5 software [R. J. Leatherbarrow, Erithacus Software Ltd., Horley, U. K. 2001] (see, Table 19 below).

Using similar methods for testing and analyses, compounds which exhibit an N1-AHB group as presented hereinabove are tested for cytotoxicity.

TABLE 19

| Compound | $LC_{50}$ values for cell line (mg/ml) | | |
|---|---|---|---|
| | HEK293 | COS-7 | MDCK |
| gentamicin | 0.70 ± 0.08 | 0.49 ± 0.06 | 0.51 ± 0.07 |
| paromomycin | 0.77 ± 0.14 | 0.90 ± 0.10 | 1.00 ± 0.06 |
| Compound 3 | 4.82 ± 0.92 | 7.03 ± 1.85 | 7.53 ± 1.21 |

As can be seen in Table 19, the $LC_{50}$ values obtained for Compound 3 were 6-fold to 15-fold higher than the $LC_{50}$ values obtained for the clinically-used aminoglycosides gentamicin and paromomycin as tested in all three cell lines.

In summary, the paromamine derivatives, Compounds 2-9, synthesized and tested by the present inventors, provide a systematic study of synthetic aminoglycosides for suppression of premature stop codons in both in vitro and ex vivo mammalian translation systems. Paromamine (Compound 1) was identified as the minimal structural motif of the clinically important drug paromomycin and was used as a scaffold for the construction of diverse structures as potential stop codon read-through inducers. These compounds showed significantly higher stop codon read-through activity and lower toxicity compared to that of the parent paromomycin in cultured cells. In COS-7 cells the activity of these compounds was also higher than that of gentamicin, the only aminoglycoside to date that was shown to have the ability to suppress nonsense mutations in patients. Antibacterial tests against both Gram-negative and Gram-positive bacterial strains indicate that these compounds are highly selective in their action in eukaryotic cells.

Based on the experimental results presented hereinabove, it can be seen that the mutation read-through inducing activity of the compounds according to the present embodiments is improved notably as measured ex vivo in mammalian cells and compared to the read-through activity of commercially availably and clinically used aminoglycosides. Moreover, the reduced toxicity of the compounds presented herein combined with their nonsense mutations suppression activity renders the use thereof highly advantageous as compared to commercially availably and clinically used aminoglycosides, since it is expected to be accompanied by fewer and more minor side effects. These observations clearly demonstrate that the compounds presented herein can be regarded as a potential new therapeutic agent for the treatment of genetic disorders caused by truncation mutations.

Taken together, these results suggest that the compounds presented herein could represent an alternative to gentamicin and paromomycin for mutation suppression therapy, thus providing a new direction for the development of novel aminoglycoside-based small molecules that target mammalian cells selectively by means of optimizing the efficiency of aminoglycoside-induced suppression of premature stop mutations.

Example 3

Activity of Exemplary Compound 37

An exemplary compound of the compounds presented herein, Compound 37, was selected for further comparative studies regarding its capacity to read-through, and thus suppress the expression of stop codon mutations both in-vitro and ex-vivo in mammalian cultured cells. The assays were conducted in comparison to another potent compound according to the present embodiments, Compound 3, and to other known aminoglycosides.

All chemicals and reagents were obtained from common commercial sources unless otherwise stated.

Comparative In Vitro Suppression of PCDH15 Nonsense Mutations, Underling Type 1 Usher Syndrome, by Various Aminoglycosides:

Compound 37 was tested for its ability to suppress a nonsense mutation in-vitro, using a reporter construct carrying either R3X nonsense mutation (a premature UGA C stop codon) or R245X nonsense mutation (a premature UGA A stop codon) of the PCDH15 gene, using gentamicin, paromomycin and Compound 3 as standards and following the experimental procedures presented hereinabove.

Each compound was assayed at several different concentrations and the concentrations at which maximal suppression levels were observed are given in Table 20.

Table 20 below presents the maximum in vitro suppression levels achieved for R3X and R245X mutations. The results were obtained at aminoglycoside concentration for which maximal suppression level was achieved. The determination of the suppression and translation levels were performed as previously reported [6]. Each compound was assayed at several different concentrations and the concentrations at which maximal suppression levels were observed are given. The results are averages of at least three independent experiments.

TABLE 20

| Aminoglycoside | R3X | | R245X | |
|---|---|---|---|---|
| | Concentration ($\mu M$)$^a$ | suppression level (%)$^b$ | Concentration ($\mu M$)$^a$ | suppression level (%)$^b$ |
| gentamicin | 46 | 50 ± 3 | 61 | 11 ± 1.5 |
| paromomycin | 56 | 49 ± 6 | 42 | 9 ± 3 |
| Compound 3 | 142 | 21 ± 9 | 178 | 6.0 ± 0.3 |
| Compound 37 | 153 | 71 ± 9 | 153 | 40.5 ± 7.5 |

As can be seen in Table 20, Compound 37, in which the AHB moiety is attached at N-1 position, shows the highest suppression levels than that of its parent Compound 3, as well as than those of paromomycin and gentamicin. The maximal suppression level of Compound 37 (71%) for R3X nonsense mutation is over three-fold higher than that of Compound 3 (21%). Furthermore, it has been previously shown that both the basal and aminoglycoside-induced suppression of UGA A stop codon is much less efficient than that of the UGA C stop codon [6]. Although the sequence contest around the stop codon has also significance on the suppression efficiency [23, 92] and as such it was expected that the suppression levels of R3X and R245X would be different, it was expected that since R245X consists of the UGA A stop sequence its suppression by aminoglycosides could be less efficient than that of R3X that consists of a UGA C stop sequence. Indeed, the maximal suppression levels of all aminoglycosides tested, the suppression of R245X nonsense mutation are significantly lower that of the R3X nonsense mutation.

As can further be seen in Table 20, while the difference in suppression of R3X versus R245X in gentamicin, paromomycin and Compound 3, are in the order of 4.5-, 5.4- and 3.5-fold, respectively, only 1.8-fold difference is observed for Compound 37. Moreover, Compound 37 with a maximal suppression level of 40.5% of the R245X nonsense mutation, is 3.6-, 4.5- and 6.5-fold better than gentamicin, paromomycin and Compound 3, respectively, and turns out to be the best aminoglycoside derivative for the suppression of this mutation. It is note that although the maximal suppression level of Compound 37 was obtained at 100 $\mu M$, a concentration which is much higher than the concentrations required for the maximal activities of both gentamicin and paromomycin, the preference of Compound 37 over gentamicin, paromomycin and Compound 3, was also observed at the same concentrations of Compound 37 and these compounds.

Comparative In Vitro Suppression of PCDH15, CFTR, Dystrophin and IDUA Nonsense Mutations by Various Aminoglycosides, Using Dual Luciferase Reporter System:

The impact of Compound 37 on other genetic diseases was tested on models of the following genetic diseases.

Cystic Fibrosis (CF)—Cystic Fibrosis Transmembrane Conductance Regulator (CFTR) is a chloride channel which controls the regulation of chloride and sodium transport in secretory epithelial cells [93]. Mutations in the CFTR gene have been found to cause CF, a recessive hereditary disorder. Different mutations cause defects in CFTR production and function by different molecular mechanisms: production of defective proteins, faulty protein processing or regulation, malfunctioning proteins or mutations affecting the levels or the processing of mRNA. Nonsense mutations account for approximately 10% of the total mutant alleles in CF patients. Among them the G542X mutation constitutes roughly 2.5% of all nonsense mutations. However, in certain populations the incidence of nonsense mutations is much higher, namely in Ashkenazi Jews the W1282X is the most common mutation and together with other nonsense mutations accounts for 64% of all CF alleles [93, 94].

Duchenne Muscular Dystrophy (DMD)—DMD is a severe X-linked neuromuscular disorder with an incidence of 1/3,500 male births, which results from mutations in the gene that encodes the dystrophin protein [95, 96]. The most distinctive feature of DMD is a progressive proximal muscular dystrophy with characteristic pseudohypertrophy of the calves. The onset usually occurs before the age of three years, and the victim is chair-ridden by the age of twelve and dead by the age of twenty. Approximately two-thirds of the mutations in both forms are deletions of one or many exons in the dystrophin gene. The vast majority of DMD point mutations result in premature translation termination, namely are nonsense mutations; these account for approximately 5-13% of the muscular dystrophies. It seems likely that most cases of DMD arise as a result of a reduction in the level of dystrophin transcripts [97].

Usher Syndrome (USH)—USH is estimated to be the most frequent cause of deaf-blindness in the United States. It is characterized by congenital profound sensorineural hearing loss, vestibular areflexia, and retinitis pigmentosa, with onset near puberty [98]. The frequency of USH was estimated to be from 1/16,000 to 1/50,000 in various populations [99]. It was determined that the carrier frequencies of the nonsense mutation R245X are 0.79% and 2.48% among Ashkenazi Jews from New York and Israel, respectively, thus being the major cause of USH Type IF in Ashkenazi Jewish population [100].

Hurler Syndrome—Hurler Syndrome or Mucopolysaccharidosis type IH (MPSIH) is a hereditary recessive disorder associated with deficiency of the alpha-L-iduronidase enzyme, which is involved in the degradation of glycosaminoglycans (GAGs), or mucopolysaccharides. The accumulation of partially degraded GAGs causes interference with cell, tissue, and organ function. The clinical features of Hurler syndrome include coarse facies, corneal clouding, mental retardation, hernias, dysostosis multiplex and hepatosplenomegaly. Children with Hurler syndrome appear normal at birth and develop the characteristic appearance over the first years of life [101]. In a group of patients of European descent with MPS I it was established that the 2 most common mutations are the nonsense mutations W402X and Q70X, which together account for approximately 70% of mutant alleles [102].

To evaluate the read-through efficiency induced by aminoglycosides, the most abundant nonsense mutations as underline causes of the above diseases were selected. These included $R_{3381}X$ for DMD, R3X and R245X for USH1, G542X and W1282X for CF, Q70X and W402X for Hurler Syndrome.

DNA fragments derived from the subsequent genes, including the tested stop mutation or the corresponding wild-type codon, and four upstream and downstream flanking codons (except for p.R3X constructs, in which there are only two upstream PCDH15-flanking codons) were cloned into p2Luc plasmid between renilla and firefly luciferase genes as described previously [90]. The formed plasmids, as well as the original p2Luc plasmid containing a TGA C nonsense mutation, were transcribed and translated in vitro and the stop codon suppression efficiency was calculated as described previously [90].

The main advantage of this in vitro system, over the in vitro assay used above (see footnote of Table 20) is that in addition to rapid and precise estimation of the read-through activity, it is also functional assay wherein the assay deciphers the enzymatic activity of the translated luciferase proteins. In the previously used in vitro reporter system, the readthrough activity was estimated by protein length only, while the activity of the produced full-length protein was not tested at all. Thus, the main advantage of this dual-luciferase reporter system is the fact that misincorporation of amino acids that would affect the enzymatic activities of the luciferase proteins is also taken under consideration. Using the dual luciferase reporter system, in vitro suppression levels induced by Compound 37, Compound 3, and paromomycin, for each of the eight nonsense mutation carrying constructs were tested, and the results are presented in FIG. 5 and Table 21 below.

For the rat-PGM-β-Gal in vitro readthrough system, the pDB series of reporter plasmids harbor the following elements under SP6 promoter control: an open reading frame (ORF) derived from the 5' end of the rat PGM gene, which encodes a 25-kDa polypeptide; another small ORF, encoding the 10-kDa alpha complementation region of β-galactosidase, and terminated by tandem, in-frame stop codons (UAA UAG); located between the two ORFs is a DNA fragment derived from PCDH15 cDNA, including the tested stop mutation or the corresponding wild-type codon, and six upstream and downstream flanking codons (except for p.R3X constructs, in which there are only two upstream PCDH15-flanking codons). The fragments were created by annealing the following couples of complementary oligonucleotides:

p.R3X:
(SEQ ID NO: 3)
5'-GATCCATGTTTC/TGACAGTTTTATCTCTGGACA-3';
and (SEQ ID NO: 4)
5'-AGCTTGTCCAGAGATAAAACTGTCG/AAAACATG-3';

p.R245X:
(SEQ ID NO: 5)
5'-GATCCCAAAATCTGAATGAGAGGC/TGAACAACCACCACCACCCT
CGCA-3';
and (SEQ ID NO: 6)
5'-AGCTTGCGAGGGTGGTGGTGGTTGTTCG/ACCTCTCATTCAGATT
TTGG-3.

Usher Syndrome (PCDH15):
p.R3X:
(SEQ ID NO: 7)
5'-TCGACATGTTTT/CGACCAGTTTTATCTCTGGACAGAGCT-3';
and (SEQ ID NO: 8)
5'-CTGTCCAGAGATAAAACTGT/GCAAAACATGGATCG-3' p.R245X:
(SEQ ID NO: 9)
5'-TCGACAAAATCTGAATGAGAGGT/CGAACAACCACCACCACCCTC
GAGCT-3';
and (SEQ ID NO: 10)
5'-CGAGGGTGGTGGTGGTTGTTCG/ACCTCTCATTCAGATTTTG-3'.

Cystic Fibrosis (CFTR):
p.G542X:
(SEQ ID NO: 11)
5'-TCGACCAATATAGTTCTTT/GGAGAAGGTGGAATCGAGCT-3';
and (SEQ ID NO: 12)
5'-CGATTCCACCTTCTCA/GAAGAACTATATTGG-3';

p.W1282X:
(SEQ ID NO: 13)
5'-TCGACAACTTTGCAACAGTGA/GAGGAAAGCCTTTGAGCT-3';
and (SEQ ID NO: 14)
5'-CAAAGGCTTTCCTT/CCACTGTTGCAAAGTTG-3'.

Duchenne Muscular Dystrophy (Dystrophin):
p.R3381X:
(SEQ ID NO: 15)
5'-TCGACAAAAAACAAATTTTGA/CACCAAAAGGTATGAGCT-3';
and (SEQ ID NO: 16)
5'-CATACCTTTTGGTT/GCAAAATTTGTTTTTTG-3'.

Hurler Syndrome (IDUA):
p.Q70X:
(SEQ ID NO: 17)
5'-TCGACCCTCAGCTGGGACT/CAGCAGCTCAACCTCGAGCT-3';
and (SEQ ID NO: 18)
5'-CGAGGTTGAGCTGCTA/GGTCCCAGCTGAGG-3';

p.W402X:
(SEQ ID NO: 19)
5'-TCGACTGAGGAGCAGCTCTGA/GGCCGAAGTGTCGGAGCT-3';
and (SEQ ID NO: 20)
5'-CCGACACTTCGGCT/CCAGAGCTGCTCCTCAG-3'.

The fragments were inserted into the BamHI and HindIII restriction sites of the pDB read-through construct [6]. Reporter plasmids harboring each of the four nonsense mutations and the corresponding wt alleles were in vitro transcribed and translated using the TNT SP6 Coupled Reticulocyte lysate System (Promega) in the presence of [$^{35}$S]-methionine and increasing concentrations of aminoglycosides as described previously [6]. Reaction products were separated by electroporation on a 12.5% SDS-polyacrylamide gel, which was dried and subjected to PhosphorImager analysis. The degree of suppression was calculated as the relative proportion of the 35-kDa product out of total reaction products (35-kDa and 25-kDa polypeptides). The results are averages of at least three independent experiments.

For the dual luciferase in vitro transcription/translation assay, DNA fragments derived from PCDH15, CFTR, Dystrophin and IDUA cDNAs, including the tested stop mutation or the corresponding wild-type codon, and four upstream and downstream flanking codons (except for p.R3X constructs, in which there are only two upstream PCDH15-flanking codons) were created by annealing the couples of complementary oligonucleotides presented above.

Fragments were inserted into the SalI and SacI restriction sites of the p2Luc plasmid between renilla and firefly luciferase genes [90]. The afforded plasmids, as well as the original p2Luc plasmid containing a TGA C nonsense mutation, were transcribed and translated using the TNT Reticulocyte Lysate Quick Coupled Transcription/Translation System (Promega™). Each transcription/translation reaction (10 μl, total volume) contained 8 μl TNT T7 Quick Master Mix, 0.2 μl methionine (1 mM), 0.8 μl DNA template (2 μg/μl), 1 μl of either water (blank) or 1 μl solution of increasing concentrations of the tested aminoglycosides in water. Luciferase activity was determined following 90 minutes incubation at 30° C. using the Dual Luciferase Reporter Assay System (Promega™). The total luminescence produced by each one of the proteins was measured separately using the FLx800 multidetection plate reader (Bio-Tek) and the stop codon suppression efficiency was calculated as described previously [90]. The results are averages of at least three independent experiments.

For the, suppression of nonsense mutations by novel compounds was tested ex vivo using a dual luciferase reporter plasmid ex vivo readthrough assay [90]. To generate the p2luc plasmid harboring the R3X nonsense mutation of the PCDH15 gene, the following oligonucleotides: 5'-GATCCACAGAAGATGTTTTGACAGTTT-TATCTCTGGACAGAGCT-3' (SEQ ID NO: 21) and 5'-CT-GTCCAGAGATAAAACTGTCAAAACATCTTCTGTG-3' (SEQ ID NO: 22) were annealed to each other and inserted into to polylinker sequence of the p2luc vector. The reporter plasmid p2luc-R3X was transfected to cos-7 cells with Lipofectamine 2000 (Invitrogen) and addition of tested compounds was performed 5 hours post transfection. Luciferase activity was determined after 24 hours of incubation, using the Dual Luciferase Reporter Assay System (Promega) and stop codon readthrough was calculated as described previously [90].

FIGS. 5A-5H present the results of the in vitro stop codon suppression levels assays, induced by gentamicin (marked by black squares), paromomycin (marked by while squares), Compound 37 (marked by black circles) and Compound 3 (marked by white circles) in various nonsense mutation context constructs, p2luc (FIG. 5A), R3381X (Duchenne Muscular Dystrophy) (FIG. 5B), R3X (FIG. 5C), R245X (Usher Syndrome) (FIG. 5D), G542X (FIG. 5E), W1282X (Cystic Fibrosis) (FIG. 5F), Q70X (FIG. 5G) and W402X (Hurler Syndrome) (FIG. 5H), and the suppression level was calculated as the relation between the firefly and the renilla luciferases luminescence of the mutant and of the wild type vectors.

Table 21 presents the maximum in vitro suppression levels (by percent) of nonsense mutations from a panel of genetic diseases, which were derived from the data presented in FIGS. 5A-5H. The compounds were tested in concentrations at which maximum suppression level was achieved.

TABLE 21

| Tested compound | Conc. (μM) | Maximum in vitro suppression (%) | | | | | | | |
|---|---|---|---|---|---|---|---|---|---|
| | | UGAC | R3X | R245X | G542X | W1282X | R3381X | Q70X | W402X |
| 1 | 490 | 1.1 ± 0.1 | 0.6 ± 0.1 | ND | ND | ND | ND | ND | ND |
| NB56 | 878 | 7.1 ± 0.8 | 7.4 ± 0.7 | 1.4 ± 0.2 | 0.30 ± 0.09 | 0.57 ± 0.15 | 1.7 ± 0.3 | 3.5 ± 1.2 | 11.3 ± 1.5 |
| gentamicin | 46 | 17.7 ± 2.9 | 14.0 ± 1.0 | 0.90 ± 0.28 | 2.8 ± 0.7 | 1.4 ± 0.5 | 3.5 ± 0.7 | 1.5 ± 0.4 | 7.2 + 0.5 |
| paromomycin | 42 | 7.8 ± 2.2 | 9.4 ± 0.5 | 0.71 ± 0.32 | 0.74 ± 0.08 | 1.2 ± 0.2 | 2.4 ± 0.3 | 2.2 ± 0.5 | 3.3 ± 0.1 |
| Compound 3 | 107 | 4.8 ± 0.8 | 2.9 ± 0.9 | 0.98 ± 0.30 | 0.63 ± 0.29 | 1.6 ± 0.4 | 1.8 ± 0.2 | 2.0 ± 0.4 | 3.2 ± 0.4 |
| Compound 37 | 46 | 18.4 ± 1.6 | 29.2 ± 3.1 | 4.9 ± 0.5 | 5.1 ± 0.6 | 3.3 ± 0.4 | 7.8 ± 0.8 | 10.6 ± 1.1 | 21.9 ± 4.4 |

As can be seen in Table 23, the measured half-maximal inhibitory concentration ($IC_{50}$) values show that all of the tested aminoglycosides inhibit translation both in prokaryotes and eukaryotes, although, for all the compounds, there is significant preference for inhibiting translation in prokaryotes versus eukaryotes.

As can further be seen in Table 23, there is a noteworthy exception to this trend in the case of Compound 37 and Compound 3. While both gentamicin and paromomycin inhibit prokaryotic translation by about tree order of magnitude preference than in eukaryotes, this difference in Compound 37 and Compound 3 drops to about two-order of magnitude. Furthermore, the efficacy by which both Compound 37 and Compound 3 inhibit prokaryotic ribosome is significantly lower than that of gentamicin and paromomycin. These data are in accord with the observed antibacterial data of this set of compounds, presented in Table 23.

Thus, while both gentamicin and paromomycin showed significant antibacterial activities against *Escherichia coli* (R477-100) with the minimal inhibitory concentrations (MIC) of 6 and 22 μM, respectively, both Compound 37 and Compound 3 exhibited lack of significant antibacterial activity (MIC values of 384 and 790 μM, respectively). Similar correlation between prokaryotic antitranslational activity and MIC values in *E. coli* has been reported previously [103].

In contrast to prokaryotic translation, both Compound 37 and Compound 3 inhibit eukaryotic translation with higher efficacy than gentamicin and paromomycin. Compound 37 ($IC_{50}$=24 μM) is about 3-fold more efficient than gentamicin ($IC_{50}$=60 μM) and paromomycin ($IC_{50}$=58 μM); Compound 3 ($IC_{50}$=31 μM) is about 2-fold more efficient than these two drugs (see, Table 23). These collective results indicate that Compound 37 and Compound 3 are more specific for eukaryotic ribosomes than gentamicin and paromomycin. Furthermore, the specificity of Compound 37 to cytoplasmic ribosome is slightly greater than that of Compound 3. Thus, the increased specificity observed together with the greater affinity of Compound 37 versus Compound 3 to the cytoplasmic A site should be the basis for the observed improved suppression efficiency of the Compound 37 over that of Compound 3.

Conclusions:

Compound 37, an exemplary compound according to the present embodiments, shows significantly improved stop codon readthrough activity and toxicity. DNA fragments derived from the mutant PCDH15, CFTR, Dystrophin and IDUA genes carrying nonsense stop mutations and represent underlying causes for the genetic diseases USH1, CF, DMD and Hurler syndrome, respectively, were used to evaluate stop codon suppression ability of Compound 37 relative to that of gentamicin and paromomycin in vitro. In all mutations tested Compound 37 exhibited superior suppression activity to that of gentamicin and paromomycin. The efficiency of Compound 37 over that of all other known aminoglycosides was greater for the suppression of different stop codons (UGA and UAG), different flanking sequences surrounding the stop codons, and different identities of the fourth base immediately followed to the stop codon (C, A, and G). In cultured cell lines (COS-7 cells) Compound 37 exhibited maximum suppression level of 5.25% of the R3X nonsense mutation, which was 3.2-, 2.8- and 1.9-fold greater than that of paromomycin and gentamicin, respectively. Furthermore, Compound 37 has significantly reduced cell toxicity and acute toxicity in mice in comparison to paromomycin and gentamicin. The accumulative data indicates that Compound 37 may be more efficiently used for suppression therapeutic purposes.

Example 4

Chemical-Enzymatic Attachment of an N-1-AHB Moiety to Aminoglycoside Derivatives Since the regioselective attachment of the AHB moiety on the aminoglycoside structure frequently requires long protection schemes [5] and the efficiency of a particular strategy is generally dependent on the structure of the parent aminoglycoside, the present inventors have used a shorter enzymatic approach as an alternative method. In this context, the present inventors reported [104] that the biosynthesis of Butirosin B from Ribostamycin involves two sequential enzymatic steps, as illustrated in Scheme 11 below.

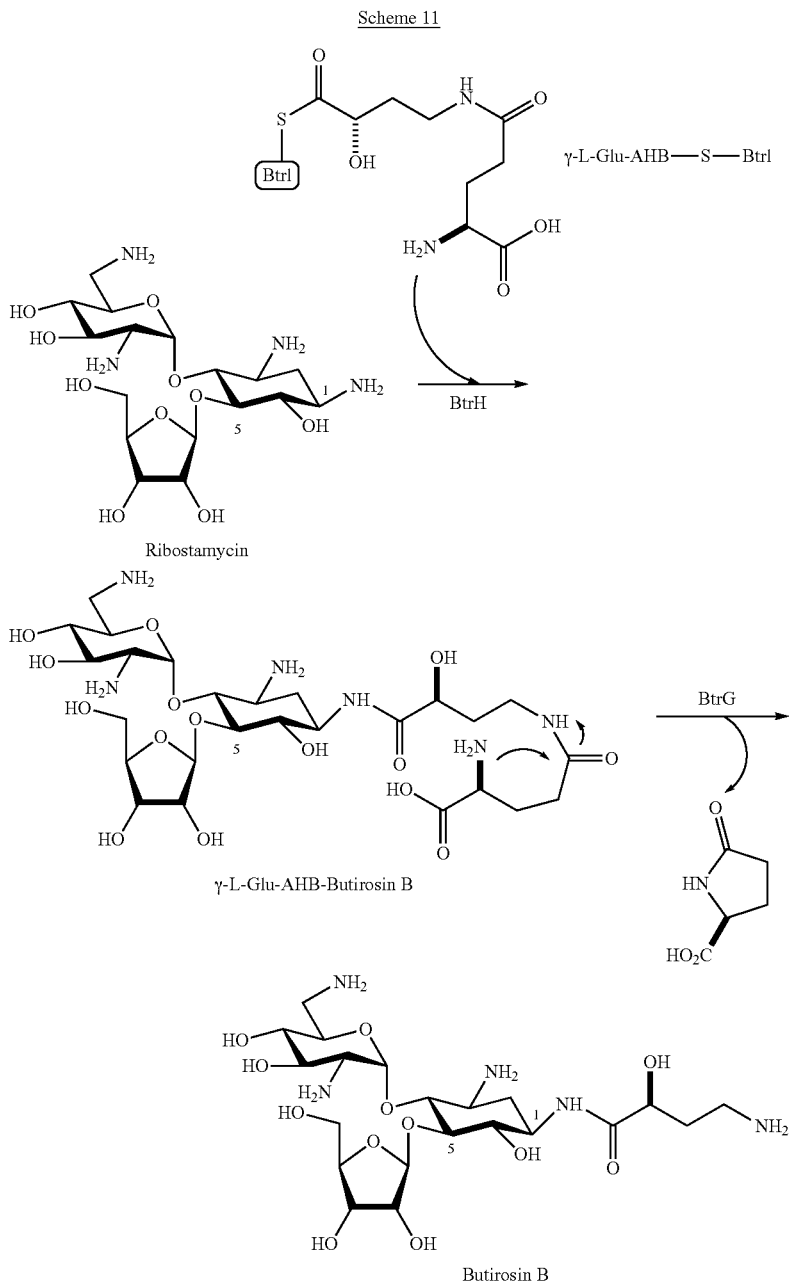

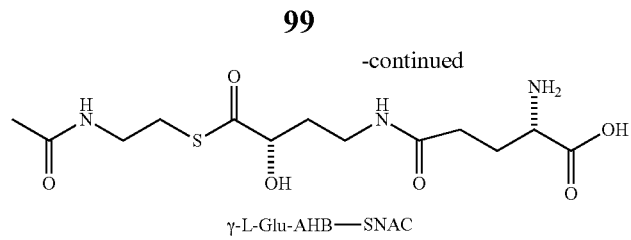

γ-L-Glu-AHB—SNAC

As can be seen in Scheme 11, the AHB moiety is first transferred from the acyl carrier protein BtrI to the precursor aminoglycoside ribostamycin as a γ-glutamylated dipeptide by the acyltransferase enzyme BtrH to yield γ-L-Glu-butirosin B; the protective γ-glutamyl group is then cleaved by the BtrG enzyme via an intramolecular transamidation mechanism. The application of this method to the combined chemical-enzymatic production of a variety of the novel N-1-AHB-bearing aminoglycoside derivative compounds according to the present embodiments was particularly suitable because the recombinant BtrH and BtrG enzymes are easily accessible as N-terminally His6-tagged proteins [104], and that the native acyl donor γ-L-Glu-AHB-S-BtrI (see, Scheme 11), which is rather difficult to produce in large quantities, can be very efficiently replaced by the synthetic N-acetylcysteamine thioester γ-L-Glu-AHB-SNAC (see, Scheme 11) [105]. In addition, preliminary tests of this system's tolerance for alternative aminoglycoside acceptors indicated that, in addition to ribostamycin, related native aminoglycosides such as neomycin and paromomycin could also be efficiently converted to the corresponding N-1-AHB derivatives [105].

Accordingly, an efficient chemoenzymatic method for the preparation of a vide variety of 2-DOS-containing aminoglycosides with the valuable AHB pharmacophore according to the present embodiments, has been developed, using the BtrH/BtrG catalytic system with the synthetic acyl donor γ-L-Glu-AHB-SNAC. Since the compound presented herein are polycationic and thus are water soluble substances, the addition of the AHB side chain is done in the final steps of the synthesis, and as such, the presented method significantly shortens and simplifies the chemical strategies that necessitate long protection schemes for this purpose. The observed broad substrate tolerance of the BtrH enzyme for the synthetic substances tested so far, along with the easy accessibility of the recombinant BtrH and BtrG enzymes also make this method attractive for high throughput synthesis of a library of 2-DOS-containing aminoglycosides to discover valuable hits with potent biomedical relevance.

Introduction of an AHB Moiety—a General Procedure:

Following is a general procedure for the attachment of an AHB moiety to a reactive amino group in an aminoglycoside derivative compound according to the present embodiments, as illustrated in Scheme 12 below.

Scheme 12

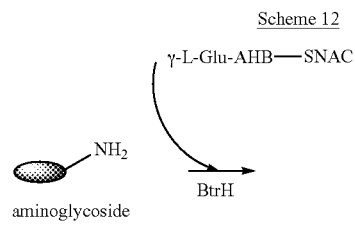

γ-L-Glu-AHB-aminoglycoside aminoglycoside-AHB

To the reaction mixture (total volume of 50 μL) containing HEPES buffer (50 mM, pH 7.9), synthetic acyl donor γ-L-Glu-AHB-SNAC (5 mM) and a precursor of a compound for AHB attachment (1.2 mM), according to the present embodiment, is added the purified BtrH enzyme (125 μg) and the mixture is incubated at 20° C. for 6 hours. The protein is removed by addition of 20 μl chloroform followed by vortexing and centrifugation (13,000 rpm, 5 minutes). The clear aqueous layer is taken for the next enzymatic step without further purification.

A small aliquot (about 1 μl) of this solution is taken for LC-ESI-MS/MS analysis to determine the percentage of conversion of the aminoglycoside substrate to the desired product.

To the aqueous layer from the previous step is added the purified BtrG enzyme (18 μg) and the mixture is incubated at 20° C. for 24 hours. The protein is removed as above and the aqueous layer is taken for LC-ESI-MS/MS analysis using an Agilent HP1100 HPLC system coupled to a Thermo-Finnigan LCQ ion-trap mass spectrometer equipped with an electrospray ionization (ESI) source.

After enzymatic reactions the samples are separated on a 2.0×250 mm Luna 5 μ C18(2) column (Phenomenex) by the following gradient at a flow rate of 0.3 ml/min and column temperature of 40° C.: 0-20 minutes 10%-50% B, 20-21 minutes 50%-10% B, 21-25 minutes 10% B (buffer A: 0.1% pentafluoropropionic acid (PFPA) in $H_2O$; buffer B: 0.1% PFPA in MeCN). Mass spectra were acquired from 250 to 1000 Da. MS/MS is carried out on target ions with 20% relative collision energy (helium as collision gas).

Preparative scale reactions are performed as above in a total volume of 10-15 ml, and with the addition of 1.5 mg BtrH and 1.0 mg BtrG. The incubation time for both enzymatic steps is also extended to 24 hours. The aqueous layer, after removal of BtrG, is loaded onto Dowex 50W ($NH_4^+$ form) 15×80 mm ion-exchange column. The column is washed with water (50 mL) followed by elution with 1% $NH_4OH$ in water. Fractions containing product, detected by TLC using $CH_2Cl_2/MeOH/H_2O/MeNH_2$ (33% solution in EtOH, 10:15:6:15), are combined and evaporated to dryness. The residue is dissolved in water, the pH is adjusted to 3.5 by $H_2SO_4$ (0.05 M) and lyophilized to afford the sulfate salt which is used for all the spectral analyses.

Chemical-Enzymatic Preparation of Compound 37:

Compound 37 (also referred to herein as NB54) was prepared from Compound 3 (also referred to herein as NB30) with full preservation of N-1 regioselectivity by BtrH with according to the General Procedure provided hereinabove, as illustrated in Scheme 13 and compared to the chemically synthesized sample which was prepared as described hereinabove.

The recombinant BtrH and BtrG enzymes were isolated as homogeneous N-terminally $His_6$-tagged proteins according to the previously reported procedures [104]. The synthetic acyl donor γ-L-Glu-AHB-SNAC was synthesized as previously described [105]. Compound 3 was synthesized as described hereinabove.

FIGS. 8A-8D present a comparison of $^1H$ NMR spectra (FIGS. 8A and 8B) and $^{13}C$ NMR spectra (FIGS. 8C and D) of Compound 37 prepared by the chemo-enzymatic procedure presented herein (FIGS. 8A and 8C) and by the chemical procedure presented herein (FIGS. 8B and 8D), whereas the "*" denotes unidentified impurities.

FIGS. 9A-9C present a comparison of 2D-COSY spectra of Compound 37 prepared by chemical (FIG. 9A) and

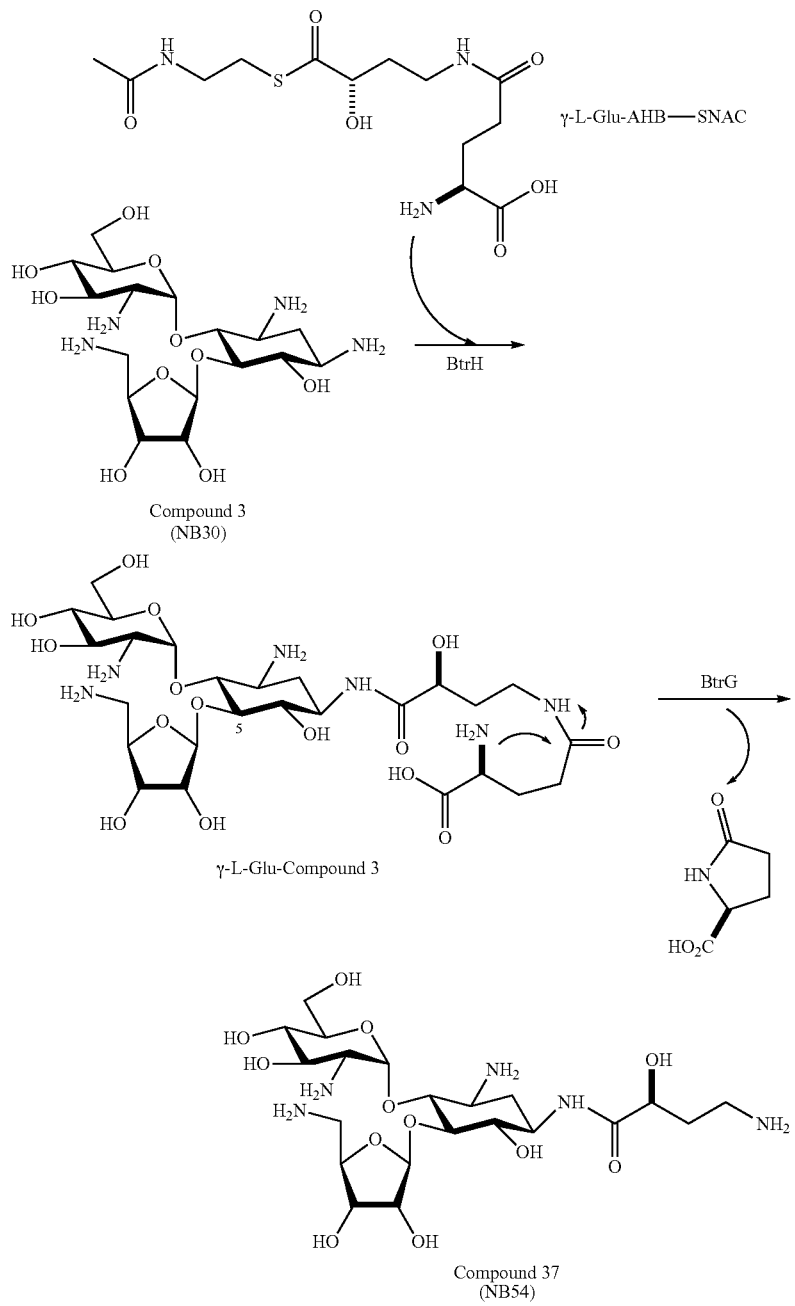

Scheme 13 chemoenzymatic (FIG. 9B) procedures presented herein, with that of the Compound 3 (FIG. 9C), whereas the dashed lines show correlations between 2-Hax and 2-Heq protons with 1-H and 3-H protons of the 2-DOS ring, highlighting strong downfield shift of the 1-H proton in Compound 37 versus 1-H proton in the parent compound Compound 3.

Figure 8:
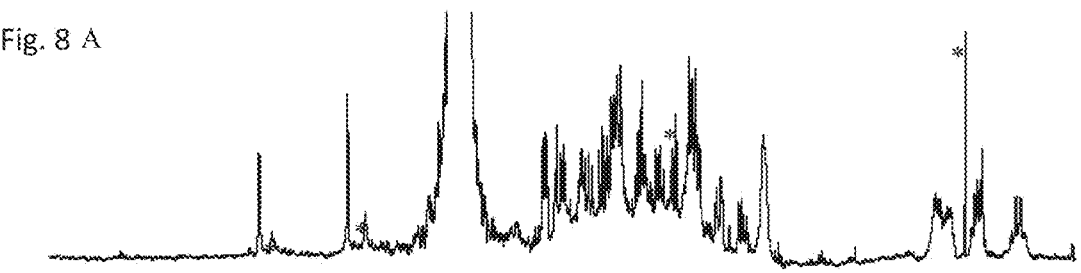
Figure 8:
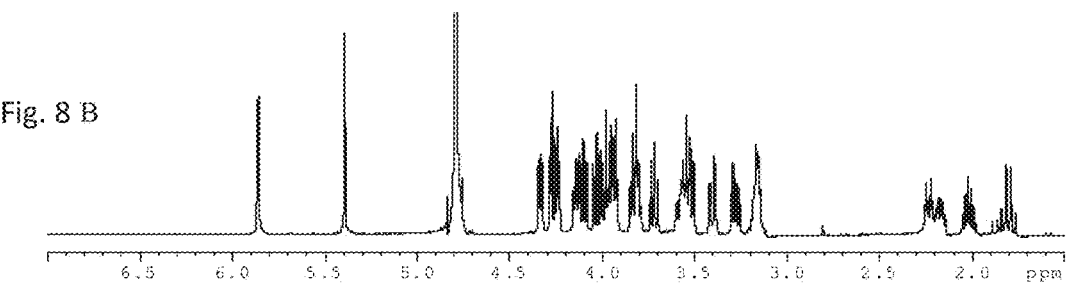
Figure 8:
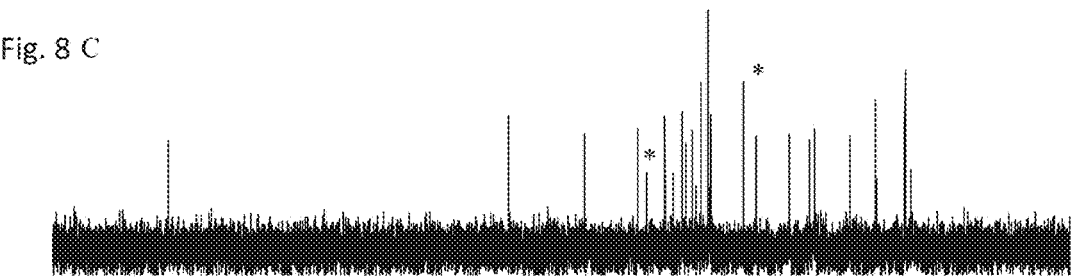
Figure 8:
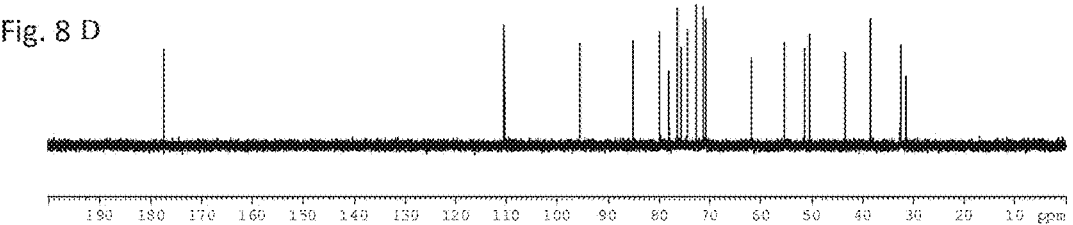

As can be seen in FIGS. 8 and 9, all the 1D and 2D NMR data of the enzymatic product, under the same pH and counterion conditions, are identical to that of the synthetic compound. Furthermore, preliminary tests of Compound 37 for in vitro readthrough activity of the TGA stop codon, demonstrated that it exhibits significantly higher stop codon read-through activity than its parent Compound 3 and the natural drug paromomycin.

In conclusion, it has been demonstrated herein that an efficient chemoenzymatic process for the preparation of a vide variety of 2-DOS-containing aminoglycosides with the valuable AHB pharmacophore by using the BtrH/BtrG catalytic system with the synthetic acyl donor γ-L-Glu-AHB-SNAC, can afford the compounds according to the present embodiments.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES CITED BY NUMERALS

Other References are Cited within the Text

1. OMIM. *Online Mendelian Inheritance in Man* [cited; Available from: http://www(dot)ncbi(dot)nlm(dot)nih (dot)gov/omim/.
2. Atkinson, J. and R. Martin, *Mutations to nonsense codons in human genetic disease: implications for gene therapy by nonsense suppressor tRNAs*. Nucleic Acids Res., 1994. 22(8): p. 1327-34.
3. Burke, J. F. and A. E. Mogg, *Suppression of a nonsense mutation in mammalian cells in vivo by the aminoglycoside antibiotics G-418 and paromomycin*. Nucleic Acids Res., 1985. 13(17): p. 6265-72.
4. Kaufman, R. J., *Correction of genetic disease by making sense from nonsense*. J. Clin. Invest., 1999. 104(4): p. 367-8.
5. Kerem, E., *Pharmacologic therapy for stop mutations: how much CFTR activity is enough?* Curr. Opin. Pulm. Med., 2004. 10(6): p. 547-52.
6. Manuvakhova, M., K. Keeling, and D. M. Bedwell, *Aminoglycoside antibiotics mediate context-dependent suppression of termination codons in a mammalian translation system*. Rna, 2000. 6(7): p. 1044-55.
7. Davis, B. D., *Mechanism of bactericidal action of aminoglycosides*. Microbiol. Rev., 1987. 51(3): p. 341-50.
8. Jana, S. and J. K. Deb, *Molecular understanding of aminoglycoside action and resistance*. Appl. Microbiol. Biotechnol., 2006. 70(2): p. 140-50.
9. Fujisawa, K., T. Hoshiya, and H. Kawaguchi, *Aminoglycoside antibiotics. VII. Acute toxicity of aminoglycoside antibiotics*. J. Antibiot. (Tokyo), 1974. 27(9): p. 677-81.
10. Magnet, S. and J. S. Blanchard, *Molecular insights into aminoglycoside action and resistance*. Chem. Rev., 2005. 105(2): p. 477-98.
11. Ogle, J. M., et al., *Recognition of cognate transfer RNA by the 30S ribosomal subunit*. Science, 2001. 292(5518): p. 897-902.
12. Vicens, Q. and E. Westhof, *Molecular recognition of aminoglycoside antibiotics by ribosomal RNA and resistance enzymes: an analysis of x-ray crystal structures*. Biopolymers, 2003. 70(1): p. 42-57.
13. Schluenzen, F., et al., *Structure of functionally activated small ribosomal subunit at 3.3 angstroms resolution*. Cell, 2000. 102(5): p. 615-23.
14. Wimberly, B. T., et al., *Structure of the 30S ribosomal subunit*. Nature, 2000. 407(6802): p. 327-39.
15. Ogle, J. M., et al., *Selection of tRNA by the ribosome requires a transition from an open to a closed form*. Cell, 2002. 111(5): p. 721-32.
16. Carter, A. P., et al., *Functional insights from the structure of the 30S ribosomal subunit and its interactions with antibiotics*. Nature, 2000. 407(6802): p. 340-8.
17. Selmer, M., et al., *Structure of the 70S ribosome complexed with mRNA and tRNA*. Science, 2006. 313(5795): p. 1935-42.
18. Francois, B., et al., *Crystal structures of complexes between aminoglycosides and decoding A site oligonucleotides: role of the number of rings and positive charges in the specific binding leading to miscoding*. Nucleic Acids Res., 2005. 33(17): p. 5677-90.
19. Vicens, Q. and E. Westhof, *Crystal structure of paromomycin docked into the eubacterial ribosomal decoding A site*. Structure (Camb), 2001. 9(8): p. 647-58.
20. Vicens, Q. and E. Westhof, *Crystal structure of geneticin bound to a bacterial 16S ribosomal RNA A site oligonucleotide*. J. Mol. Biol., 2003. 326(4): p. 1175-88.
21. Vicens, Q. and E. Westhof, *Crystal structure of a complex between the aminoglycoside tobramycin and an oligonucleotide containing the ribosomal decoding a site*. Chem. Biol., 2002. 9(6): p. 747-55.
22. Fourmy, D., S. Yoshizawa, and J. D. Puglisi, *Paromomycin binding induces a local conformational change in the A-site of 16 S rRNA*. J. Mol. Biol., 1998. 277(2): p. 333-45.
23. Howard, M. T., et al., *Sequence specificity of aminoglycoside-induced stop condon readthrough: potential implications for treatment of Duchenne muscular dystrophy*. Ann. Neurol., 2000. 48(2): p. 164-9.
24. Bedwell, D. M., et al., *Suppression of a CFTR premature stop mutation in a bronchial epithelial cell line*. Nat. Med., 1997. 3(11): p. 1280-4.
25. Howard, M., R. A. Frizzell, and D. M. Bedwell, *Aminoglycoside antibiotics restore CFTR function by overcoming premature stop mutations*. Nat. Med., 1996. 2(4): p. 467-9.

26. Du, M., et al., *Aminoglycoside suppression of a premature stop mutation in a Cftr-/- mouse carrying a human CFTR-G542X transgene.* J. Mol. Med., 2002. 80(9): p. 595-604.
27. Wilschanski, M., et al., *Gentamicin-induced correction of CFTR function in patients with cystic fibrosis and CFTR stop mutations.* N. Engl. J. Med., 2003. 349(15): p. 1433-41.
28. Barton-Davis, E. R., et al., *Aminoglycoside antibiotics restore dystrophin function to skeletal muscles of mdx mice.* J. Clin. Invest., 1999. 104(4): p. 375-81.
29. Keeling, K. M., et al., *Gentamicin-mediated suppression of Hurler syndrome stop mutations restores a low level of alpha-L-iduronidase activity and reduces lysosomal glycosaminoglycan accumulation.* Hum. Mol. Genet., 2001. 10(3): p. 291-9.
30. Sangkuhl, K., et al., *Aminoglycoside-mediated rescue of a disease-causing nonsense mutation in the V2 vasopressin receptor gene in vitro and in vivo.* Hum. Mol. Genet., 2004. 13(9): p. 893-903.
31. Helip-Wooley, A., et al., *Expression of CTNS alleles: subcellular localization and aminoglycoside correction in vitro.* Mol. Genet. Metab., 2002. 75(2): p. 128-33.
32. Grayson, C., et al., *In vitro analysis of aminoglycoside therapy for the Arg120stop nonsense mutation in RP2 patients.* J. Med. Genet., 2002. 39(1): p. 62-7.
33. Xi, B., F. Guan, and D. S. Lawrence, *Enhanced production of functional proteins from defective genes.* J. Am. Chem. Soc., 2004. 126(18): p. 5660-1.
34. Forge, A. and J. Schacht, *Aminoglycoside antibiotics.* Audiol. Neurootol., 2000. 5(1): p. 3-22.
35. Nagai, J. and M. Takano, *Molecular aspects of renal handling of aminoglycosides and strategies for preventing the nephrotoxicity.* Drug Metab. Pharmacokinet., 2004. 19(3): p. 159-70.
36. Kaul, M., C. M. Barbieri, and D. S. Pilch, *Defining the basis for the specificity of aminoglycoside-rRNA recognition: a comparative study of drug binding to the A sites of Escherichia coli and human rRNA.* J. Mol. Biol., 2005. 346(1): p. 119-34.
37. Vicens, Q. and E. Westhof, *RNA as a drug target: the case of aminoglycosides.* Chembiochem, 2003. 4(10): p. 1018-23.
38. Keeling, K. M. and D. M. Bedwell, *Pharmacological suppression of premature stop mutations that cause genetic diseases.* Curr. Pharmacogenomics, 2005. 3(4): p. 259-269.
39. Sener, G., et al., *Melatonin protects against gentamicin-induced nephrotoxicity in rats.* J. Pineal. Res., 2002. 32(4): p. 231-6.
40. Kawamoto, K., et al., *Antioxidant gene therapy can protect hearing and hair cells from ototoxicity.* Mol. Ther., 2004. 9(2): p. 173-81.
41. Gilbert, D. N., et al., *Polyaspartic acid prevents experimental aminoglycoside nephrotoxicity.* J. Infect. Dis., 1989. 159(5): p. 945-53.
42. Beauchamp, D., et al., *Protection against gentamicin-induced early renal alterations (phospholipidosis and increased DNA synthesis) by coadministration of poly-L-aspartic acid.* J. Pharmacol. Exp. Ther., 1990. 255(2): p. 858-66.
43. Thibault, N., et al., *Protection against gentamicin nephrotoxicity by daptomycin in nephrectomized rats.* Life Sci., 1995. 56(22): p. 1877-87.
44. Thibault, N., et al., *Attenuation by daptomycin of gentamicin-induced experimental nephrotoxicity.* Antimicrob. Agents Chemother., 1994. 38(5): p. 1027-35.
45. Watanabe, A., et al., *Targeted prevention of renal accumulation and toxicity of gentamicin by aminoglycoside binding receptor antagonists.* J. Control Release, 2004. 95(3): p. 423-33.
46. Bartal, C., et al., *Pharmacokinetic dosing of aminoglycosides: a controlled trial.* Am. J. Med., 2003. 114(3): p. 194-8.
47. Beauchamp, D. and G. Labrecque, *Aminoglycoside nephrotoxicity: do time and frequency of administration matter?* Curr. Opin. Crit. Care, 2001. 7(6): p. 401-8.
48. Karpati, G. and H. Lochmuller, *When running a stop sign may be a good thing.* Ann. Neurol., 2001. 49(6): p. 693-4.
49. Chernikov, V. G., et al., *Comparison of cytotoxicity of aminoglycoside antibiotics using a panel cellular biotest system.* Bull. Exp. Biol. Med., 2003. 135(1): p. 103-5.
50. Keeling, K. M. and D. M. Bedwell, *Clinically relevant aminoglycosides can suppress disease-associated premature stop mutations in the IDUA and P53 cDNAs in a mammalian translation system.* J. Mol. Med., 2002. 80(6): p. 367-76.
51. Howard, M. T., et al., *Readthrough of dystrophin stop codon mutations induced by aminoglycosides.* Ann. Neurol., 2004. 55(3): p. 422-6.
52. Mattis, V. B., et al., *Novel aminoglycosides increase SMN levels in spinal muscular atrophy fibroblasts.* Hum. Genet., 2006. 120(4): p. 589-601.
53. Arcamone, F. C., Giuseppe; Cuccia, Pietro B.; Di Colo, Giacomo, *Synthesis of b-D-ribofuranosyl derivatives of paromamine.* Annali di Chimica (Rome, Italy) 1974. 64(7-8): p. 485-96.
54. Haddad, J., et al., *Design of novel antibiotics that bind to the ribosomal acyltransfer site.* J. Am. Chem. Soc., 2002. 124(13): p. 3229-37.
55. Hanessian, S. O., Tomoya; Takamoto, Tetsuyoshi, *Aminoglycoside antibiotics: synthesis of pseudotrisaccharides derived from neamine and paromamine.* Canadian Journal of Chemistry, 1978. 56(11): p. 1500-8.
56. Kirby, J. P., D. B. Borders, and G. E. Van Lear, *Structure of LL-BM408 an aminocyclitol antibiotic.* J Antibiot (Tokyo), 1977. 30(2): p. 175-7.
57. Marrero-Ponce, Y., et al., *Atom, atom-type, and total nonstochastic and stochastic quadratic fingerprints: a promising approach for modeling of antibacterial activity.* Bioorg Med Chem, 2005. 13(8): p. 2881-99.
58. Minowa, N., et al., *Synthesis and antibacterial activity of novel neamine derivatives.* Bioorg. Med. Chem. Lett., 2006. In Press.
59. Ogawa, T. T., T; Hanessian, S, *Amionglycoside antibiotics. Synthesis of 6-0-(b-D-ribofuranosyl)paromamine.* Tetrahedron Letters, 1974. 46: p. 4013-16.
60. Russell, R. J., et al., *The complex of a designer antibiotic with a model aminoacyl site of the 30S ribosomal subunit revealed by X-ray crystallography.* J. Am. Chem. Soc., 2003. 125(12): p. 3410-1.
61. Takeda, K., et al., *Biosynthesis of butirosins. I. Biosynthetic pathways of butirosins and related antibiotics.* J Antibiot (Tokyo), 1979. 32(1): p. 18-28.
62. Aurino, S. and V. Nigro, *Readthrough strategies for stop codons in Duchenne muscular dystrophy.* Acta Myol., 2006. 25(1): p. 5-12.
63. Kerem, E., et al., *Effectiveness of PTC124 treatment of cystic fibrosis caused by nonsense mutations: a prospective phase II trial.* Lancet, 2008. 372(9640): p. 719-27.
64. Du, M., et al., *PTC124 is an orally bioavailable compound that promotes suppression of the human CFTR-G542X nonsense allele in a CF mouse model.* Proc Natl Acad Sci USA, 2008. 105(6): p. 2064-9.

65. Wilton, S., PTC124, nonsense mutations and Duchenne muscular dystrophy. Neuromuscul Disord, 2007. 17(9-10): p. 719-20.
66. Welch, E. M., et al., PTC124 targets genetic disorders caused by nonsense mutations. Nature, 2007. 447(7140): p. 87-91.
67. Hirawat, S., et al., Safety, tolerability, and pharmacokinetics of PTC124, a nonaminoglycoside nonsense mutation suppressor, following single-and multiple-dose administration to healthy male and female adult volunteers. J Clin Pharmacol, 2007. 47(4): p. 430-44.
68. Sandoval, R. M., et al., A non-nephrotoxic gentamicin congener that retains antimicrobial efficacy. J. Am. Soc. Nephrol., 2006. 17(10): p. 2697-705.
69. Pfister, P., et al., The molecular basis for A-site mutations conferring aminoglycoside resistance: relationship between ribosomal susceptibility and X-ray crystal structures. Chembiochem, 2003. 4(10): p. 1078-88.
70. Recht, M. I., S. Douthwaite, and J. D. Puglisi, Basis for prokaryotic specificity of action of aminoglycoside antibiotics. Embo J., 1999. 18(11): p. 3133-8.
71. Aberra, F. N., et al., Antibiotic use and the risk of flare of inflammatory bowel disease. Clin Gastroenterol Hepatol, 2005. 3(5): p. 459-65.
72. Dejace, P. and J. Klastersky, Emergence of resistance as a consequence of antimicrobial prophylaxis in immunocompromised patients. Scand J Infect Dis Suppl, 1986. 49: p. 165-71.
73. Hughes, J. M. and F. C. Tenover, Approaches to limiting emergence of antimicrobial resistance in bacteria in human populations. Clin Infect Dis, 1997. 24 Suppl 1: p. S131-5.
74. Kollef, M. H., Bench-to-bedside review: antimicrobial utilization strategies aimed at preventing the emergence of bacterial resistance in the intensive care unit. Crit Care, 2005. 9(5): p. 459-64.
75. Stratton, C. W., Dead bugs don't mutate: susceptibility issues in the emergence of bacterial resistance. Emerg Infect Dis, 2003. 9(1): p. 10-6.
76. Veeneman, G. H., S. H. Van Leeuwen, and J. H. Van Boom, Iodonium ion-promoted reactions at the anomeric center. II. An efficient thioglycoside-mediated approach toward the formation of 1,2-trans-linked glycosides and glycosidic esters. Tetrahedron Lett., 1990. 31(9): p. 1331-4.
77. Schmidt, R. R., Angew. Chem. Int. Ed. Engl., 1986. 25: p. 212.
78. Ding, Y., et al., Efficient synthesis of neomycin B related amino glycosides. Tetrahedron Lett., 2000. 41(21): p. 4049-4052.
79. Du, M., et al., Clinical doses of amikacin provide more effective suppression of the human CFTR-G542X stop mutation than gentamicin in a transgenic CF mouse model. J. Mol. Med., 2006. 84(7): p. 573-82.
80. Nudelman, I., et al., Redesign of aminoglycosides for treatment of human genetic diseases caused by premature stop mutations. Bioorg. Med. Chem. Lett., 2006. 16: p. 6310-6315.
81. Nagabhushan, T. L., et al., Interaction of Vicinal and Nonvicinal Amino-Hydroxy Group Pairs in Aminoglycoside-Aminocyclitol Antibiotics with Transition-Metal Cations—Selective N-Protection. J. Am. Chem. Soc., 1978. 100(16): p. 5253-5254.
82. Moon, M. S., et al., Synthesis of the selectively protected garamine derivatives as aminoglycoside intermediates. Bull. Korean Chem. Soc., 2003. 24(2): p. 163-164.
83. Kirst, H. A., B. A. Truedell, and J. E. Toth, Control of Site-Specific Substitution of Aminoglycosides by Transition-Metal Cations. Tet. Lett., 1981. 22(4): p. 295-298.
84. Nam, G., et al., An efficient and selective 1-N-monoethylation of sisomicin: Process development of netilmicin. Org. Proc. Res. Dev., 2002. 6(1): p. 78-81.
85. Alper, P. B., et al., Probing the specificity of aminoglycoside-ribosomal RNA interactions with designed synthetic analogs. J. Am. Chem. Soc., 1998. 120: p. 1965-1978.
86. Fridman, M., et al., Dual effect of synthetic aminoglycosides: antibacterial activity against Bacillus anthracis and inhibition of anthrax lethal factor. Angew. Chem. Int. Ed. Engl., 2005. 44(3): p. 447-452.
87. Petit, C., Usher syndrome: from genetics to pathogenesis. Annu. Rev. Genomics Hum. Genet., 2001. 2: p. 271-97.
88. Ahmed, Z. M., et al., Mutations of the protocadherin gene PCDH15 cause Usher syndrome type 1F. Am. J. Hum. Genet., 2001. 69(1): p. 25-34.
89. Kaul, M., C. M. Barbieri, and D. S. Pilch, Fluorescence-based approach for detecting and characterizing antibiotic-induced conformational changes in ribosomal RNA: comparing aminoglycoside binding to prokaryotic and eukaryotic ribosomal RNA sequences. J. Am. Chem. Soc., 2004. 126(11): p. 3447-53.
90. Grentzmann, G., et al., A dual-luciferase reporter system for studying recoding signals. Rna, 1998. 4(4): p. 479-86.
91. National Committee for Clinical Laboratory Standards, Performance standards for antimicrobial susceptibility testing. Fifth information supplement: Approved Standard M100-S5. 1994, Villanova, Pa.: NCCLS.
92. Mccaughan, K. K., et al., Translational Termination Efficiency in Mammals Is Influenced by the Base Following the Stop Codon. Proceedings of the National Academy of Sciences of the United States of America, 1995. 92(12): p. 5431-5435.
93. Kerem, E., Pharmacological induction of CFTR function in patients with cystic fibrosis: mutation-specific therapy. Pediatr. Pulmonol., 2005. 40(3): p. 183-96.
94. Cystic Fibrosis Mutation Database.
95. Prior, T. W., Perspectives and molecular diagnosis of Duchenne and Becker muscular dystrophies. Clin Lab Med, 1995. 15(4): p. 927-41.
96. Prior, T. W., et al., Spectrum of small mutations in the dystrophin coding region. Am J Hum Genet, 1995. 57(1): p. 22-33.
97. Roberts, R. G., R. J. Gardner, and M. Bobrow, Searching for the 1 in 2,400,000: a review of dystrophin gene point mutations. Hum Mutat, 1994. 4(1): p. 1-11.
98. Smith, R. J., et al., Clinical diagnosis of the Usher syndromes. Usher Syndrome Consortium. Am J Med Genet, 1994. 50(1): p. 32-8.
99. Rebibo-Sabbah, A., et al., In vitro and ex vivo suppression by aminoglycosides of PCDH15 nonsense mutations underlying type 1 Usher syndrome. Hum Genet, 2007. 122(3-4): p. 373-381.
100. Ben-Yosef, T., et al., A mutation of PCDH15 among Ashkenazi Jews with the type 1 Usher syndrome. N. Engl. J. Med., 2003. 348(17): p. 1664-70.
101. Wraith, J. E., J. G. Rogers, and D. M. Danks, The mucopolysaccharidoses. Aust Paediatr J, 1987. 23(6): p. 329-34.
102. Bunge, S., et al., Prenatal diagnosis and carrier detection in mucopolysaccharidosis type II by mutation analysis. A 47,XXY male heterozygous for a missense point mutation. Prenat Diagn, 1994. 14(9): p. 777-80.
103. Greenberg, W. A., et al., Design and synthesis of new aminoglycoside antibiotics containing neamine as an optimal core structure: correlation of antibiotic activity with in vitro inhibition of translation. J. Am. Chem. Soc., 1999. 121: p. 6527-6541.

104. Llewellyn, N. M., Y. Li, and J. B. Spencer, *Biosynthesis of butirosin: transfer and deprotection of the unique amino acid side chain*. Chem Biol, 2007. 14(4): p. 379-86.

105. Llewellyn, N. M. and J. B. Spencer, *Chemoenzymatic acylation of aminoglycoside antibiotics*. Chem Commun (Camb), 2008(32): p. 3786-8.

What is claimed is:

1. A method of inducing readthrough of a premature stop codon mutation in a subject in need thereof, said premature stop codon mutation being associated with a genetic disorder, the method comprising administering to the subject a therapeutically effective amount of a compound having a general Formula I:

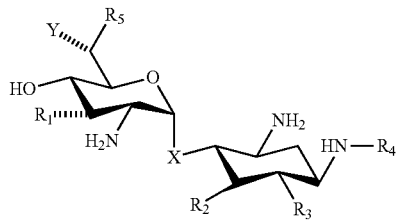

Formula I or a pharmaceutically acceptable salt thereof,
wherein:
each of $R_1$, $R_2$ and $R_3$ is independently a monosaccharide moiety, halide, hydroxyl, amine or an oligosaccharide moiety, at least one of $R_1$, $R_2$ and $R_3$ being a monosaccharide moiety having the general Formula II:

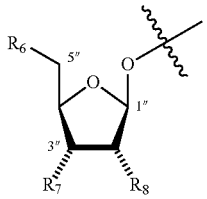

Formula II wherein each of $R_6$, $R_7$ and $R_8$ is independently selected from the group consisting of hydroxyl and amine, or $R_1$ being an oligosaccharide moiety,
whereas when $R_2$ is said monosaccharide moiety having said Formula II, $R_6$ is amine;
X is oxygen or sulfur;
$R_4$ is (S)-4-amino-2-hydroxybutyryl (AHB);
$R_5$ is hydroxyl;
Y is hydrogen or alkyl; and
each of the dashed lines indicates independently an R configuration or an S configuration,
the method further comprising administering to the subject another agent useful in the treatment of said genetic disorder.

2. The method of claim 1, wherein said compound is:

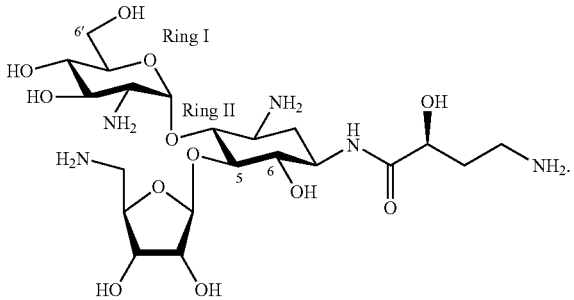

Compound 37

3. The method of claim 1, wherein X is oxygen.
4. The method of claim 1, wherein Y is hydrogen.
5. The method of claim 1, wherein at least one of $R_1$, $R_2$ and $R_3$ is a disaccharide moiety.
6. The method of claim 1, wherein Y is alkyl.

7. The method of claim 1, wherein said genetic disorder is selected from the group consisting of cystic fibrosis (CF), Duchenne muscular dystrophy (DMD), ataxia-telangiectasia, Hurler syndrome, hemophilia A, hemophilia B, Usher syndrome, Tay-Sachs Becker muscular dystrophy (BMD), Congenital muscular dystrophy (CMD), Factor VII deficiency, Familial atrial fibrillation, Hailey-Hailey disease, McArdle disease, Mucopolysaccharidosis, Nephropathic cystinosis, Polycystic kidney disease, Rett syndrome, Spinal muscular atrophy (SMA), X-linked nephrogenic diabetes insipidus (XNDI) and X-linked retinitis pigmentosa.

8. A method of inducing readthrough of a premature stop codon mutation in a subject in need thereof, said premature stop codon mutation being associated with a genetic disorder, the method comprising administering to the subject a therapeutically effective amount of a compound having a general Formula I:

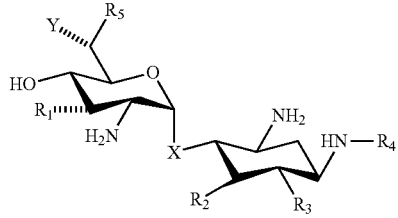

Formula I or a pharmaceutically acceptable salt thereof, wherein:

each of $R_1$, $R_2$ and $R_3$ is independently a monosaccharide moiety, hydroxyl, amine or an oligosaccharide moiety, and at least one of $R_1$, $R_2$ and $R_3$ being a monosaccharide moiety having the general Formula II:

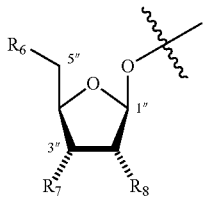

Formula II wherein each of $R_6$, $R_7$ and $R_8$ is independently selected from the group consisting of hydroxyl and amine, or $R_1$ being an oligosaccharide;

X is oxygen or sulfur;

$R_4$ is hydrogen;

$R_5$ is hydroxyl;

Y is hydrogen; and each of the dashed line indicates independently an R configuration or an S configuration, with the proviso that said compound is not selected from the group consisting of

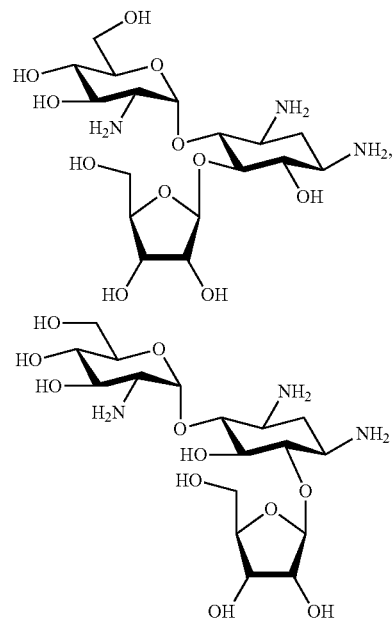

and paromomycin, the method further comprising administering to the subject another agent useful in the treatment of said genetic disorder.

9. The method of claim 8, wherein X is oxygen.

10. The method of claim 8, wherein said compound is:

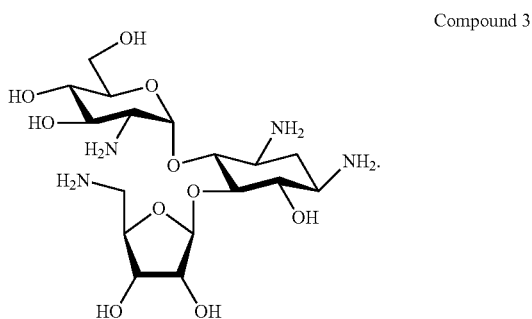

Compound 3

11. The method of claim 7, wherein said genetic disorder is selected from the group consisting of cystic fibrosis (CF), Duchenne muscular dystrophy (DMD), ataxia-telangiectasia, Hurler syndrome, hemophilia A, hemophilia B, Usher syndrome, Tay-Sachs Becker muscular dystrophy (BMD), Congenital muscular dystrophy (CMD), Factor VII deficiency, Familial atrial fibrillation, Hailey-Hailey disease, McArdle disease, Mucopolysaccharidosis, Nephropathic cystinosis, Polycystic kidney disease, Rett syndrome, Spinal muscular atrophy (SMA), X-linked nephrogenic diabetes insipidus (XNDI) and X-linked retinitis pigmentosa.

12. A method of inducing readthrough of a premature stop codon mutation in a subject in need thereof, said premature stop codon mutation being associated with a genetic disorder, the method comprising administering to the subject a therapeutically effective amount of a compound having a general Formula I:

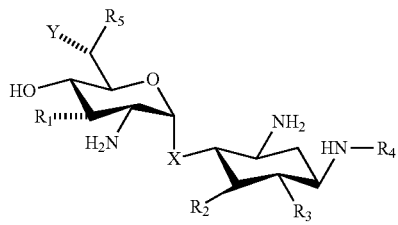

Formula I or a pharmaceutically acceptable salt thereof,
wherein:
each of $R_1$, $R_2$ and $R_3$ is independently a monosaccharide moiety, halide, hydroxyl, amine or an oligosaccharide moiety,
X is oxygen or sulfur;
$R_4$ is hydrogen or (S)-4-amino-2-hydroxybutyryl (AHB);
$R_5$ is hydroxyl or amine;
Y is alkyl; and
each of the dashed line indicates independently an R configuration or an S configuration,
and wherein:
at least one of $R_1$, $R_2$ and $R_3$ is selected from a monosaccharide moiety and an oligosaccharide moiety; and/or
$R_4$ is (S)-4-amino-2-hydroxybutyryl (AHB),
with the proviso that said compound is not G-418,
the method further comprising administering to the subject another agent useful in the treatment of said genetic disorder.

13. The method of claim 12, wherein X is oxygen.
14. The method of claim 12, wherein $R_5$ is hydroxyl.
15. The method of claim 12, wherein at least one of $R_1$, $R_2$ and $R_3$ is a monosaccharide moiety.
16. The method of claim 15, wherein $R_4$ is AHB.
17. The method of claim 12, wherein said compound is:

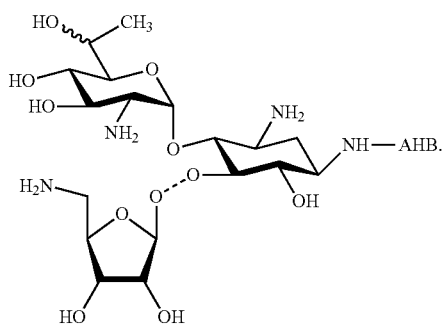

Compound 43

18. The method of claim 12, wherein said genetic disorder is selected from the group consisting of cystic fibrosis (CF), Duchenne muscular dystrophy (DMD), ataxia-telangiectasia, Hurler syndrome, hemophilia A, hemophilia B, Usher syndrome, Tay-Sachs Becker muscular dystrophy (BMD), Congenital muscular dystrophy (CMD), Factor VII deficiency, Familial atrial fibrillation, Hailey-Hailey disease, McArdle disease, Mucopolysaccharidosis, Nephropathic cystinosis, Polycystic kidney disease, Rett syndrome, Spinal muscular atrophy (SMA), X-linked nephrogenic diabetes insipidus (XNDI) and X-linked retinitis pigmentosa.

19. A method of inducing readthrough of a premature stop codon mutation in a subject in need thereof, said premature stop codon mutation being associated with a genetic disorder, the method comprising administering to the subject a therapeutically effective amount of a compound having a general Formula I:

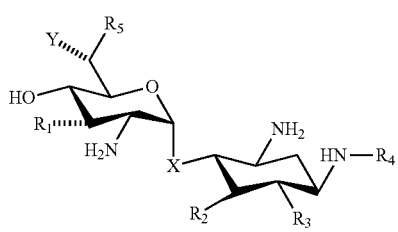

Formula I or a pharmaceutically acceptable salt thereof,
wherein:
each of $R_1$, $R_2$ and $R_3$ is independently a monosaccharide moiety, halide, hydroxyl, amine or an oligosaccharide moiety,
X is oxygen or sulfur;
$R_4$ is (S)-4-amino-2-hydroxybutyryl (AHB);
$R_5$ is hydroxyl or amine;
Y is alkyl; and
each of the dashed line indicates independently an R configuration or an S configuration,
the method further comprising administering to the subject another agent useful in the treatment of said genetic disorder.

20. The method of claim 19, wherein X is oxygen.
21. The method of claim 19, wherein $R_5$ is hydroxyl.
22. The method of claim 19, wherein at least one of $R_1$, $R_2$ and $R_3$ is a monosaccharide moiety.
23. The method of claim 19, wherein said genetic disorder is selected from the group consisting of cystic fibrosis (CF), Duchenne muscular dystrophy (DMD), ataxia-telangiectasia, Hurler syndrome, hemophilia A, hemophilia B, Usher syndrome, Tay-Sachs Becker muscular dystrophy (BMD), Congenital muscular dystrophy (CMD), Factor VII deficiency, Familial atrial fibrillation, Hailey-Hailey disease, McArdle disease, Mucopolysaccharidosis, Nephropathic cystinosis, Polycystic kidney disease, Rett syndrome, Spinal muscular atrophy (SMA), X-linked nephrogenic diabetes insipidus (XNDI) and X-linked retinitis pigmentosa.

\* \* \* \* \*

SEQUENCE LISTING

<160> NUMBER OF SEQ ID NOS: 22

<210> SEQ ID NO 1
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 1
gatccatgtt ttgacagttt tatctctgga ca                            32

<210> SEQ ID NO 2
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 2
agcttgtcca gagataaaac tgtcaaaaca tg                            32

<210> SEQ ID NO 3
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 3
gatccatgtt tygacagttt tatctctgga ca                            32

<210> SEQ ID NO 4
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 4
agcttgtcca gagataaaac tgtcraaaca tg                            32

<210> SEQ ID NO 5
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 5
gatcccaaaa tctgaatgag aggygaacaa ccaccaccac cctcgca            47

<210> SEQ ID NO 6
<211> LENGTH: 47
<212> TYPE: DNA
<213> ORGANISM: Artificial sequence
<220> FEATURE:
<223> OTHER INFORMATION: Single strand DNA oligonucleotide

<400> SEQUENCE: 6
agcttgcgag ggtggtggtg gttgttcrcc tctcattcag attttgg             47

```
<210> SEQ ID NO 7
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 7
tcgacatgtt tygaccagtt ttatctctgg acagagct                    38

<210> SEQ ID NO 8
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 8
ctgtccagag ataaaactgk caaaacatgg atcg                        34

<210> SEQ ID NO 9
<211> LENGTH: 48
<212> TYPE: DNA
<213> ORGANISM: Artificial sequence
<220> FEATURE:
<223> OTHER INFORMATION: Single strand DNA oligonucleotide

<400> SEQUENCE: 9
tcgacaaaat ctgaatgaga ggygaacaac caccaccacc ctcgagct         48

<210> SEQ ID NO 10
<211> LENGTH: 40
<212> TYPE: DNA
<213> ORGANISM: Artificial sequence
<220> FEATURE:
<223> OTHER INFORMATION: Single strand DNA oligonucleotide

<400> SEQUENCE: 10
cgagggtggt ggtggttgtt crcctctcat tcagattttg                  40

<210> SEQ ID NO 11
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 11
tcgaccaata tagttcttkg agaaggtgga atcgagct                    38

<210> SEQ ID NO 12
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 12
cgattccacc ttctcraaga actatattgg                             30

<210> SEQ ID NO 13
<211> LENGTH: 38
<212> TYPE: DNA
<213> ORGANISM: Artificial sequence
<220> FEATURE:
<223> OTHER INFORMATION: Single strand DNA oligonucleotide
```

<400> SEQUENCE: 13
tcgacaactt tgcaacagtg raggaaagcc tttgagct                                38

<210> SEQ ID NO 14
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 14
caaaggcttt cctycactgt tgcaaagttg                                          30

<210> SEQ ID NO 15
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 15
tcgacaaaaa acaaattttg maccaaaagg tatgagct                                 38

<210> SEQ ID NO 16
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 16 cataccttt ggtkcaaaat ttgttttttg                                           30

<210> SEQ ID NO 17
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 17
tcgaccctca gctgggacya gcagctcaac ctcgagct                                 38

<210> SEQ ID NO 18
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 18
cgaggttgag ctgctrgtcc cagctgagg                                           29

<210> SEQ ID NO 19
<211> LENGTH: 38
<212> TYPE: DNA
<213> ORGANISM: Artificial sequence
<220> FEATURE:
<223> OTHER INFORMATION: Single strand DNA oligonucleotide

<400> SEQUENCE: 19
tcgactgagg agcagctctg rgccgaagtg tcggagct                                 38

```
<210> SEQ ID NO 20
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 20
ccgacacttc ggcycagagc tgctcctcag                                    30

<210> SEQ ID NO 21
<211> LENGTH: 44
<212> TYPE: DNA
<213> ORGANISM: Artificial sequence
<220> FEATURE:
<223> OTHER INFORMATION: Single strand DNA oligonucleotide

<400> SEQUENCE: 21
gatccacaga agatgttttg acagttttat ctctggacag agct                    44

<210> SEQ ID NO 22
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 22
ctgtccagag ataaaactgt caaaacatct tctgtg                             36
```